US007432097B2

(12) United States Patent
Short et al.

(10) Patent No.: US 7,432,097 B2
(45) Date of Patent: *Oct. 7, 2008

(54) PHYTASES, NUCLEIC ACIDS ENCODING THEM AND METHODS OF MAKING AND USING THEM

(75) Inventors: Jay M. Short, Rancho Santa Fe, CA (US); Keith A. Kretz, San Marcos, CA (US); Kevin A. Gray, San Diego, CA (US); Nelson Robert Barton, San Diego, CA (US); James B. Garrett, San Diego, CA (US); Eileen O'Donoghue, San Diego, CA (US); William Baum, La Jolla, CA (US); Dan E. Robertson, San Diego, CA (US); Paul Zorner, Encinitas, CA (US)

(73) Assignee: Verenium Corporation, San Diego, CA (US)

( * ) Notice: Subject to any disclaimer, the term of this patent is extended or adjusted under 35 U.S.C. 154(b) by 293 days.

This patent is subject to a terminal disclaimer.

(21) Appl. No.: 10/933,115

(22) Filed: Sep. 1, 2004

(65) Prior Publication Data

US 2005/0281792 A1     Dec. 22, 2005

Related U.S. Application Data

(60) Continuation-in-part of application No. 09/866,379, filed on May 24, 2001, now Pat. No. 6,855,365, which is a continuation-in-part of application No. 09/580,515, filed on May 25, 2000, now Pat. No. 6,720,014, which is a continuation-in-part of application No. 09/318,528, filed on May 25, 1999, now Pat. No. 6,183,740, which is a continuation-in-part of application No. 09/291,931, filed on Apr. 13, 1999, now Pat. No. 6,190,897, which is a continuation of application No. 09/259,214, filed on Mar. 1, 1999, now Pat. No. 6,110,719, which is a division of application No. 08/910,798, filed on Aug. 13, 1997, now Pat. No. 5,876,997.

(51) Int. Cl.
| | |
|---|---|
| C12N 11/00 | (2006.01) |
| C12N 9/16 | (2006.01) |
| A61K 38/46 | (2006.01) |
| C07K 14/00 | (2006.01) |
| C12N 15/00 | (2006.01) |
| C12N 1/21 | (2006.01) |
| C12N 5/10 | (2006.01) |
| C12P 21/00 | (2006.01) |
| C12Q 1/44 | (2006.01) |
| C07H 21/00 | (2006.01) |

(52) U.S. Cl. ............... 435/196; 435/174; 435/320.1; 435/252.3; 435/325; 435/69.1; 435/19; 424/94.6; 530/350; 536/23.2

(58) Field of Classification Search ............... 435/196, 435/320.1, 252.3, 325, 69.1, 19; 424/94.6; 530/350; 536/23.2, 23.1
See application file for complete search history.

(56) References Cited

U.S. PATENT DOCUMENTS

| | | | |
|---|---|---|---|
| 5,284,933 | A | 2/1994 | Dobeli et al. |
| 5,366,736 | A | 11/1994 | Edwards, Jr. |
| 5,436,156 | A | 7/1995 | Van Gorcom et al. |
| 5,492,813 | A | 2/1996 | Eisenbeis et al. |
| 5,593,963 | A | 1/1997 | Van Ooijen et al. |
| 5,750,135 | A | 5/1998 | Schleicher et al. |
| 5,830,696 | A | 11/1998 | Short |
| 5,830,732 | A | 11/1998 | Mochizuki et al. |
| 5,866,118 | A | 2/1999 | Berka et al. |
| 5,939,303 | A | 8/1999 | Cheng et al. |
| 6,039,942 | A | 3/2000 | Lassen et al. |
| 6,190,897 | B1 | 2/2001 | Kretz |
| 2002/0136754 | A1 | 9/2002 | Short et al. |

FOREIGN PATENT DOCUMENTS

| | | |
|---|---|---|
| EP | 0 282 042 | 6/1994 |
| EP | 0 441 252 | 9/1997 |
| EP | 0 897 985 | 2/1999 |
| GB | 2316082 | 2/1998 |
| JP | 04 349881 | 12/1992 |
| JP | 09 504695 | 5/1997 |
| KR | 99086028 | 12/1999 |

(Continued)

OTHER PUBLICATIONS

Jung et al., J. Athl. Train. 40(2):71-75, 2005.*

(Continued)

*Primary Examiner*—Delia M Ramirez
(74) *Attorney, Agent, or Firm*—Morrison Foerster LLP

(57) ABSTRACT

In one aspect, the invention provides a purified and modified phytase enzyme from *Escherichia coli* K12 appA phytase. The enzyme has phytase activity and improved thermal tolerance as compared with the wild-type enzyme. In addition, the enzyme has improved protease stability at low pH. Glycosylation of the modified phytase provided a further improved enzyme having improved thermal tolerance and protease stability. The enzyme can be produced from native or recombinant host cells and can be used to aid in the digestion of phytate where desired. In one aspect, the phytase of the present invention can be used in foodstuffs to improve the feeding value of phytate rich ingredients.

31 Claims, 10 Drawing Sheets

FOREIGN PATENT DOCUMENTS

| | | |
|---|---|---|
| WO | WO-97/33976 | 9/1997 |
| WO | WO-98/44125 | 10/1998 |
| WO | WO-99/08539 | 2/1999 |
| WO | WO-00/58481 | 10/2000 |
| WO | WO-00/64247 | 11/2000 |
| WO | WO-00/71728 | 11/2000 |
| WO | WO-01/90333 | 11/2001 |

OTHER PUBLICATIONS

Altschul et al., J. Mol. Biol. (1990) 215:403-410.
Arnold, PNAS USA (1998) 95:2035-2036.
Bae et al., Geneseq Accession No. ABK12414, Dec. 15, 1999.
Berka et al., Applied and Environ. Biol. (1998) 64:4423-4427.
Bork et al., Genome Research (2000) 10:348-400.
Brinch-Pedersen et al., Molecular Breeding (2000) pp. 195-206.
Broun et al., Science (1998) 282:1315-1317.
Casey and Walsh, J. Biotechnol. (2004) 110:313-322.
Dassa et al., J. of Bacteriology (1990) 172:5497-5500.
Database Accession No. AAX26540, 2000.
Database Accession No. AR130956, 2001.
Database Accession No. A02249, 1996.
Database Accession No. P07102, 2002.
Dvorakova et al., Folia Microbiol. (1998) 43:323-338.
Forsberg et al., Geneseq Accession No. AAC68296, Nov. 2, 2000.
Forsberg et al., Geneseq Accession No. AAC68299, Nov. 2, 2000.
Giver et al., PNAS USA (1998) 95:12809-12813.
Golovan et al., Canadian Journal of Microbiology (2000) 46:59-71.
Greiner et al., Archives of Biochemistry and Biophysics (1993) 303:107-113.
International Search Report for PCT/US02/16482, mailed on May 24, 2002, 9 pages.
Kerovuo et al., Applied and Environ. Biol. (1998) 64:2079-2085.
Lehmann et al., Biochimica et Biophysica Acta (2000) 1543:408-415.
Lehmann et al., Protein Engineering (2000) 13:49-57.
Lehmann et al., Protein Science (2000) 1866-1872.
Lutz et al., J. of Biotechnology (2001) 85:15-24.
NCBI GenBank entry AAB96873 phytase.
NCBI GenBank entry AAA16898 phytase.
NCBI GenBank entry AAB26466 phytase.
NCBI GenBank entry AAB96871 phytase.
Ostanin et al., GenBank Accession No. L03371 (1992).
Ostanin et al., J. Biol. Chem. (1992) 267:22830-22836.
Pearson and Lipman, PNAS USA (1988) 85:2442-2448.
Pen et al., Biotechnology (1993) 11:811-814.
Rodriguez et al., Archives of Biochemistry and Biophysics (2000) 382:105-112.
Rodriguez et al., Biochemical and Biophysical Research Comm. (1999) 257:117-123.
Rozas and Rozas, Cabios (1995) 11:621-625.
Seffernick et al., Journal of Bacteriology (2001) 183:2405-2410.
Tomschy et al., Protein Science (2000) 9:1304-1311.
Van De Loo et al., PNAS USA (1995) 2:6743-6747.
Verwoerd et al., Med. Fac. Landbouww. Univ. Gent. (1993) 58(4a):1719-1721.
Vetriani et al., PNAS USA (1998) 95:12300-12305.
Von Heijne, Nucleic Acids Research (1986) 14:4683-4690.
Wodzinski and Ullah, "Phytase," in Advantages in Applied Microbiology, Academic Press Inc., vol. 42, (1996) pp. 263-302.
Wyss et al., Applied and Environmental Microbiology (1999) 65:367-373.
Boquet et al., J. of Bacteriology (1987) 169:1663-1669.
Delagrave et al., Protein Eng. (1993) 6:327-331.
Delagrave et al., Nature Biotech. (1993) 11:1548-1552.
Greiner et al., Archives of Biochemistry and Biophysics (1997) 341:201-206.
Institute of Applied Environmental Economics (TME) of the Netherlands, "Use of Phytase in Pig and Poultry Feed to Reduce Phosphorus Excretion," (1995).
Lim et al., Nature Structural Biology (2000) 7:108-113.
Oh et al., Abstracts of the General Meeting of the American Society for Microbiology (2000) 100:499-500.
Rodriguez et al., Archives of Biochemistry and Biophysics (1999) 365:262-267.
Van Hartingsveldt et al., Gene (1993) 127:87-94.
Witkowski et al., Biochemistry (1999) 38:11643-11650.
European Search Report for EP 05 01 3009, mailed on Oct. 7, 2005, 4 pages.
Guo et al., PNAS USA (2004) 101(25):9205-9210.
Branden et al., Introduction to Protein Structure, Garland Publishing Inc., New York, (1991) p. 247.
Supplementary Partial European Search Report for EP 02 74 4174, mailed on Apr. 4, 2006, 7 pages.
Cameron, Molecular Biotechnology (1997) 7:253-265.
Kappel et al., Current Opinion in Biotechnology (1992) 3:548-553.
Mullins et al., Hypertension (1993) 22(4):630-633.
Mullins et al., J. Clin. Invest. (1996) 97(7):1557-1560.
Wigley et al., Reprod. Fert. Dev. (1994) 6:585-588.
Dassa et al., J. of Biological Chemistry (1982) 257(12):6669-6676.
Nelson et al., J. Nutrition (1971) 101:1289-1294.
Warden and Schaible, Poultry Science (1962) 41:725-732.
Wu et al., Poultry Science (2006) 85:64-69.

* cited by examiner

FIGURE 1A (SEQ ID NO:1-nucleotide sequence and SEQ ID NO:2-amino acid sequence)
*Escherichia coli* B Phytase Sequence

```
1
ATG AAA GCG ATC TTA ATC CCA TTT TTA TCT CTT CTG ATT CCG TTA ACC CCG
Met Lys Ala Ile Leu Ile Pro Phe Leu Ser Leu Leu Ile Pro Leu Thr Pro

CAA TCT GCA TTC GCT CAG AGT GAG CCG GAG CTG AAG CTG GAA AGT GTG GTG
Gln Ser Ala Phe Ala Gln Ser Glu Pro Glu Leu Lys Leu Glu Ser Val Val

ATT GTC AGT CGT CAT GGT GTG CGT GCT CCA ACC AAG GCC ACG CAA CTG ATG
Ile Val Ser Arg His Gly Val Arg Ala Pro Thr Lys Ala Thr Gln Leu Met

CAG GAT GTC ACC CCA GAC GCA TGG CCA ACC TGG CCG GTA AAA CTG GGT TGG
Gln Asp Val Thr Pro Asp Ala Trp Pro Thr Trp Pro Val Lys Leu Gly Trp

CTG ACA CCG CGN GGT GGT GAG CTA ATC GCC TAT CTC GGA CAT TAC CAA CGC
Leu Thr Pro Arg Gly Gly Glu Leu Ile Ala Tyr Leu Gly His Tyr Gln Arg

CAG CGT CTG GTA GCC GAC GGA TTG CTG GCG AAA AAG GGC TGC CCG CAG TCT
Gln Arg Leu Val Ala Asp Gly Leu Leu Ala Lys Lys Gly Cys Pro Gln Ser

GGT CAG GTC GCG ATT ATT GCT GAT GTC GAC GAG CGT ACC CGT AAA ACA GGC
Gly Gln Val Ala Ile Ile Ala Asp Val Asp Glu Arg Thr Arg Lys Thr Gly

GAA GCC TTC GCC GCC GGG CTG GCA CCT GAC TGT GCA ATA ACC GTA CAT ACC
Glu Ala Phe Ala Ala Gly Leu Ala Pro Asp Cys Ala Ile Thr Val His Thr

CAG GCA GAT ACG TCC AGT CCC GAT CCG TTA TTT AAT CCT CTA AAA ACT GGC
Gln Ala Asp Thr Ser Ser Pro Asp Pro Leu Phe Asn Pro Leu Lys Thr Gly

GTT TGC CAA CTG GAT AAC GCG AAC GTG ACT GAC GCG ATC CTC AGC AGG GCA
Val Cys Gln Leu Asp Asn Ala Asn Val Thr Asp Ala Ile Leu Ser Arg Ala

GGA GGG TCA ATT GCT GAC TTT ACC GGG CAT CGG CAA ACG GCG TTT CGC GAA
Gly Gly Ser Ile Ala Asp Phe Thr Gly His Arg Gln Thr Ala Phe Arg Glu

CTG GAA CGG GTG CTT AAT TTT CCG CAA TCA AAC TTG TGC CTT AAA CGT GAG
Leu Glu Arg Val Leu Asn Phe Pro Gln Ser Asn Leu Cys Leu Lys Arg Glu

AAA CAG GAC GAA AGC TGT TCA TTA ACG CAG GCA TTA CCA TCG GAA CTC AAG
Lys Gln Asp Glu Ser Cys Ser Leu Thr Gln Ala Leu Pro Ser Glu Leu Lys

GTG AGC GCC GAC AAT GTC TCA TTA ACC GGT GCG GTA AGC CTC GCA TCA ATG
Val Ser Ala Asp Asn Val Ser Leu Thr Gly Ala Val Ser Leu Ala Ser Met

CTG ACG GAG ATA TTT CTC CTG CAA CAA GCA CAG GGA ATG CCG GAG CCG GGG
Leu Thr Glu Ile Phe Leu Leu Gln Gln Ala Gln Gly Met Pro Glu Pro Gly

TGG GGA AGG ATC ACC GAT TCA CAC CAG TGG AAC ACC TTG CTA AGT TTG CAT
Trp Gly Arg Ile Thr Asp Ser His Gln Trp Asn Thr Leu Leu Ser Leu His

AAC GCG CAA TTT TAT TTG CTA CAA CGC ACG CCA GAG GTT GCC CGC AGC CGC
Asn Ala Gln Phe Tyr Leu Leu Gln Arg Thr Pro Glu Val Ala Arg Ser Arg

GCC ACC CCG TTA TTG GAT TTG ATC ATG GCA GCG TTG ACG CCC CAT CCA CCG
Ala Thr Pro Leu Leu Asp Leu Ile Met Ala Ala Leu Thr Pro His Pro Pro
```

FIGURE 1B

```
CAA AAA CAG GCG TAT GGT GTG ACA TTA CCC ACT TCA GTA CTG TTT ATT GCC
Gln Lys Gln Ala Tyr Gly Val Thr Leu Pro Thr Ser Val Leu Phe Ile Ala

GGA CAC GAT ACT AAT CTG GCA AAT CTC GGC GGC GCA CTG GAG CTC AAC TGG
Gly His Asp Thr Asn Leu Ala Asn Leu Gly Gly Ala Leu Glu Leu Asn Trp

ACG CTT CCC GGT CAG CCG GAT AAC ACG CCG CCA GGT GGT GAA CTG GTG TTT
Thr Leu Pro Gly Gln Pro Asp Asn Thr Pro Pro Gly Gly Glu Leu Val Phe

GAA CGC TGG CGT CGG CTA AGC GAT AAC AGC CAG TGG ATT CAG GTT TCG CTG
Glu Arg Trp Arg Arg Leu Ser Asp Asn Ser Gln Trp Ile Gln Val Ser Leu

GTC TTC CAG ACT TTA CAG CAG ATG CGT GAT AAA ACG CCG CTG TCA TTA AAT
Val Phe Gln Thr Leu Gln Gln Met Arg Asp Lys Thr Pro Leu Ser Leu Asn

ACG CCG CCC GGA GAG GTG AAA CTG ACC CTG GCA GGA TGT GAA GAG CGA AAT
Thr Pro Pro Gly Glu Val Lys Leu Thr Leu Ala Gly Cys Glu Glu Arg Asn

GCG CAG GGC ATG TGT TCG TTG GCA GGT TTT ACG CAA ATC GTG AAT GAA GCA
Ala Gln Gly Met Cys Ser Leu Ala Gly Phe Thr Gln Ile Val Asn Glu Ala

CGC ATA CCG GCG TGC AGT TTG AGA TCT CAT CAC CAT CAC CAT CAC TAA   1323
Arg Ile Pro Ala Cys Ser Leu Arg Ser His His His His His His End
``` pH/Temperature Profile and Stability

FIGURE 7A

E. coli appA (GenBank accession no. M58708) (SEQ ID NO:7)

```
   1 taaggagcag aaacaatgtg gtatttactt tggttcgtcg gcattttgtt gatgtgttcg
  61 ctctccaccc ttgtgttggt atggctggac ccgcgtctga aaagttaacg aacgtaggcc
 121 tgatgcggcg cattagcatc gcatcaggca atcaataatg tcagatatga aaagcggaaa
 181 catatcgatg aaagcgatct taatcccatt tttatctctt ctgattccgt taaccccgca
 241 atctgcattc gctcagagtg agccggagct gaagctggaa agtgtggtga ttgtcagtcg
 301 tcatggtgtg cgtgctccaa ccaaggccac gcaactgatg caggatgtca ccccagacgc
 361 atggccaacc tggccggtaa aactggggttg gctgacaccg cgnggtggtg agctaatcgc
 421 ctatctcgga cattaccaac gccagcgtct ggtagccgac ggattgctgg cgaaaaaggg
 481 ctgcccgcag tctggtcagg tcgcgattat tgctgatgtc gacgagcgta cccgtaaaac
 541 aggcgaagcc ttcgccgccg ggctggcacc tgactgtgca ataaccgtac atacccaggc
 601 agatacgtcc agtcccgatc cgttatttaa tcctctaaaa actggcgttt gccaactgga
 661 taacgcgaac gtgactgacg cgatcctcag cagggcagga gggtcaattg ctgactttac
 721 cgggcatcgg caaacggcgt ttcgcgaact ggaacgggtg cttaattttc cgcaatcaaa
 781 cttgtgcctt aaacgtgaga aacaggacga aagctgttca ttaacgcagg cattaccatc
 841 ggaactcaag gtgagcgccg acaatgtctc attaaccggt gcggtaagcc tcgcatcaat
 901 gctgacggag atatttctcc tgcaacaagc acagggaatg ccggagccgg ggtggggaag
 961 gatcaccgat tcacaccagt ggaacaacctt gctaagtttg cataacgcgc aattttattt
1021 gctacaacgc acgccagagg ttgcccgcag ccgcgccacc ccgttattag atttgatcaa
1081 gacagcgttg acgccccatc caccgcaaaa acaggcgtat ggtgtgacat tacccacttc
1141 agtgctgttt atcgccggac acgatactaa tctggcaaat ctcggcggcg cactggagct
1201 caactggacg cttcccggtc agccggataa cacgccgcca ggtggtgaac tggtgtttga
1261 acgctggcgt cggctaagcg ataacagcca gtggattcag gtttcgctgg tcttccagac
1321 tttacagcag atgcgtgata aaacgccgct gtcattaaat acgccgcccg gagaggtgaa
1381 actgaccctg gcaggatgtg aagagcgaaa tgcgcagggc atgtgttcgt tggcaggttt
1441 tacgcaaatc gtgaatgaag cacgcatacc ggcgtgcagt ttgtaatgca taaaaaagag
1501 cattcagtta cctgaatgct ctgaggctga tgacaaacga agaactgtct aatgcgtaga
1561 ccggaaaagg cgttcacgcc gcatccggcc actttcagtt ttcctctttc tcggagtaac
1621 tataaccgta atagttatag ccgtaactgt aagcggtgct ggcgcgttta atcacaccat
1681 tgaggatagc gcctttaata ttgacgcctg cctgttccag acgctgcatt gacaaactca
1741 cctctttggc ggtgttcaag ccaaaacgcg caaccagcag gctggtgcca acagaacgcc
1801 ccacgaccgc ggcatcactc accgccagca tcggcggcgt atcgacaatc accagatcgt
1861 aatggtcgtt cgcccattcc agtaattgac gcatccgatc g
```

FIGURE 7B

```
   1 taaggagcag aaacaatgtg gtatttactt tggttcgtcg gcatttgtt gatgtgttcg
  61 ctctccaccc ttgtgttggt atggctggac ccgcgtctga aaagttaacg aacgtaggcc
 121 tgatgcggcg cattagcatc gcatcaggca atcaataatg tcagatatga aaagcggaaa
 181 catatcgatg aaagcgatct taatcccatt tttatctctt ctgattccgt taaccccgca
 241 atctgcattc gctcagagtg agccggagct gaagctggaa agtgtggtga ttgtcagtcg
 301 tcatggtgtg cgtgctccaa ccaaggccac gcaactgatg caggatgtca ccccagacgc
 361 atggccaacc tggccggtaa aactggggttg gctgacaccg cgnggtggtg agctaatcgc
 421 ctatctcgga cattaccaac gccagcgtct ggtagccgac ggattgctgg cgaaaaaggg
 481 ctgcccgcag tctggtcagg tcgcgattat tgctgatgtc gacgagcgta cccgtaaaac
 541 aggcgaagcc ttcgccgccg ggctggcacc tgactgtgca ataaccgtac atacccaggc
 601 agatacgtcc agtcccgatc cgttatttaa tcctctaaaa actggcgttt gccaactgga
 661 taacgcgaac gtgactgacg cgatcctcag cagggcagga gggtcaattg ctgactttac
 721 cgggcatcgg caaacggcgt ttcgcgaact ggaacgggtg cttaattttc cgcaatcaaa
 781 cttgtgcctt aaacgtgaga aacaggacga aagctgttca ttaacgcagg cattaccatc
 841 ggaactcaag gtgagcgccg acaatgtctc attaaccggt gcggtaagcc tcgcatcaat
 901 gctgacggag atatttctcc tgcaacaagc acagggaatg ccggagccgg ggtggggaag
 961 gatcaccgat tcacaccagt ggaacaccttt gctaagtttg cataacgcgc aatttattt
1021 gctacaacgc acgccagagg ttgcccgcag ccgcgccacc ccgttattag atttgatcaa
1081 gacagcgttg acgccccatc caccgcaaaa acaggcgtat ggtgtgacat tacccacttc
1141 agtgctgttt atcgccggac acgatactaa tctggcaaat ctcggcggcg cactggagct
1201 caactggacg cttcccggtc agccggataa cacgccgcca ggtggtgaac tggtgtttga
1261 acgctggcgt cggctaagcg ataacagcca gtggattcag gtttcgctgg tcttccagac
1321 tttacagcag atgcgtgata aaacgccgct gtcattaaat acgccgcccg gagaggtgaa
1381 actgaccctg gcaggatgtg aagagcgaaa tgcgcagggc atgtgttcgt tggcaggttt
1441 tacgcaaaatc gtgaatgaag cacgcatacc ggcgtgcagt ttgtaatgca taaaaaagag
1501 cattcagtta cctgaatgct ctgaggctga tgacaaacga agaactgtct aatgcgtaga
1561 ccggaaaagg cgttcacgcc gcatccggcc actttcagtt ttcctctttc tcggagtaac
1621 tataaccgta atagttatag ccgtaactgt aagcggtgct ggcgcgttta atcacaccat
1681 tgaggatagc gcctttaata ttgacgcctg cctgttccag acgctgcatt gacaaactca
1741 cctctttggc ggtgttcaag ccaaaacgcg caaccagcag gctggtgcca acagaacgcc
1801 ccacgaccgc ggcatcactc accgccagca tcggcggcgt atcgacaatc accagatcgt
1861 aatggtcgtt cgcccattcc agtaattgac gcatccgatc g
```

FIGURE 8A
Amino acid sequence for E. coli appA (wild type) (SEQ ID NO:8)

MKAILIPFLSLLIPLTPQSAFAQSEPELKLESVVIVSRHGVRAPTKATQLMQDVT
PDAWPTWPVKLGWLTPRGGELIAYLGHYQRQRLVADGLLAKKGCPQSGQVA
IIADVDERTRKTGEAFAAGLAPDCAITVHTQADTSSPDPLFNPLKTGVCQLDNA
NVTDAILSRAGGSIADFTGHRQTAFRELERVLNFPQSNLCLKREKQDESCSLTQ
ALPSELKVSADNVSLTGAVSLASMLTEIFLLQQAQGMPEPGWGRITDSHQWNT
LLSLHNAQFYLLQRTPEVARSRATPLLDLIKTALTPHPPQKQAYGVTLPTSVLFI
AGHDTNLANLGGALELNWTLPGQPDNTPPGGELVFERWRRLSDNSQWIQVSL
VFQTLQQMRDKTPLSLNTPPGEVKLTLAGCEERNAQGMCSLAGFTQIVNEARI
PACSL

FIGURE 8B
Bold-Underlined amino acid residues are shown below in the modified appA enzyme
(SEQ ID NO:10)

MKAILIPFLSLLIPLTPQSAFAQSEPELKLESVVIVSRHGVRAPTKATQLMQDVT
PDAWPTWPVKLGELTPRGGELIAYLGHYWRQRLVADGLLPKCGCPQSGQVAI
IADVDERTRKTGEAFAAGLAPDCAITVHTQADTSSPDPLFNPLKTGVCQLDNA
NVTDAILERAGGSIADFTGHYQTAFRELERVLNFPQSNLCLKREKQDESCSLTQ
ALPSELKVSADCVSLTGAVSLASMLTEIFLLQQAQGMPEPGWGRITDSHQWNT
LLSLHNAQFDLLQRTPEVARSRATPLLDLIKTALTPHPPQKQAYGVTLPTSVLFI
AGHDTNLANLGGALELNWTLPGQPDNTPPGGELVFERWRRLSDNSQWIQVSL
VFQTLQQMRDKTPLSLNTPPGEVKLTLAGCEERNAQGMCSLAGFTQIVNEARI
PACSL

PHYTASES, NUCLEIC ACIDS ENCODING THEM AND METHODS OF MAKING AND USING THEM

CROSS-REFERENCE TO RELATED APPLICATIONS

This application is a continuation in part (CIP) of U.S. patent application Ser. No. 09/866,379, filed May 24, 2001, now U.S. Pat. No. 6,855,365, issued Feb. 15, 2005, which is a continuation-in-part of U.S. patent application Ser. No. 09/580,515, filed May 25, 2000, now U.S. Pat. No. 6,720,014, issued Apr. 13, 2004, which is a continuation-in-part of U.S. patent application Ser. No. 09/318,528, filed May 25, 1999, now U.S. Pat. No. 6,183,740, issued Feb. 06, 2001, which is a continuation-in-part of U.S. patent application Ser. No. 09/291,931, filed Apr. 13, 1999, now U.S. Pat. No. 6,190,897, issued Feb. 20, 2001, which is a continuation of U.S. patent application Ser. No. 09/259,214, filed Mar. 1, 1999, now U.S. Pat. No. 6,110,719, issued Aug. 29, 2000, which is a divisional of U.S. patent application Ser. No. 08/910,798, now U.S. Pat. No. 5,876,997, filed Aug. 13, 1997, all of which are hereby incorporated by reference in their entirety for all purposes.

FIELD OF THE INVENTION

This invention relates to newly identified and newly engineered polynucleotides, polypeptides encoded by such polynucleotides, the use of such polynucleotides and polypeptides, as well as the production and isolation of such polynucleotides and polypeptides. More particularly, the polypeptides of the present invention have been identified as enzymes having phytase activity.

BACKGROUND OF THE INVENTION

Minerals are essential elements for the growth of all organisms. Dietary minerals can be derived from many source materials, including plants. E.g., plant seeds are a rich source of minerals since they contain ions that are complexed with the phosphate groups of phytic acid molecules. These phytate-associated minerals satisfy the dietary needs of some species of farmed organisms, such as multi-stomached ruminants. Accordingly, ruminants do not require dietary supplementation with inorganic phosphate and minerals because microorganisms in the rumen produce enzymes that catalyze conversion of phytate (myo-inositol-hexaphosphate) to inositol and inorganic phosphate. In the process, minerals that have been complexed with phytate are released. The majority of species of farmed organisms, however, are unable to efficiently utilize phytate-associated minerals. Thus, for example, in the livestock production of monogastric animals (e.g., pigs, birds, and fish), feed is commonly supplemented with minerals &/or with antibiotic substances that alter the digestive flora environment of the consuming organism to enhance growth rates.

As such, there are many problematic burdens—related to nutrition, ex vivo processing steps, health and medicine, environmental conservation, and resource management—that are associated with an insufficient hydrolysis of phytate in many applications. The following are non-limiting examples of these problems:

1) The supplementation of diets with inorganic minerals is a costly expense.
2) The presence of unhydrolyzed phytate is undesirable and problematic in many ex vivo applications (e.g. by causing the presence of unwanted sludge).
3) The supplementation of diets with antibiotics poses a medical threat to humans and animals alike by increasing the abundance of antibiotic-tolerant pathogens.
4) The discharge of unabsorbed fecal minerals into the environment disrupts and damages the ecosystems of surrounding soils, fish farm waters, and surface waters at large.
5) The valuable nutritional offerings of many potential foodstuffs remain significantly untapped and squandered.

Many potentially nutritious plants, including particularly their seeds, contain appreciable amounts of nutrients, e.g. phosphate, that are associated with phytate in a manner such that these nutrients are not freely available upon consumption. The unavailability of these nutrients is overcome by some organisms, including cows and other ruminants, that have a sufficient digestive ability—largely derived from the presence of symbiotic life forms in their digestive tracts—to hydrolyze phytate and liberate the associated nutrients. However, the majority of species of farmed animals, including pigs, fish, chickens, turkeys, as well as other non-ruminant organisms including man, are unable to efficiently liberate these nutrients after ingestion.

Consequently, phytate-containing foodstuffs require supplementation with exogenous nutrients and/or with a source of phytase activity in order to ammend their deficient nutritional offerings upon consumption by a very large number of species of organisms.

In yet another aspect, the presence of unhydrolized phytate leads to problematic consequences in ex vivo processes including—but not limited to—the processing of foodstuffs. In but merely one exemplification, as described in EP0321004-B1 (Vaara et al.), there is a step in the processing of corn and sorghum kernels whereby the hard kernels are steeped in water to soften them. Water-soluble substances that leach out during this process become part of a corn steep liquor, which is concentrated by evaporation. Unhydrolized phytic acid in the corn steep liquor, largely in the form of calcium and magnesium salts, is associated with phosphorus and deposits an undesirable sludge with proteins and metal ions. This sludge is problematic in the evaporation, transportation and storage of the corn steep liquor. Accordingly, the instantly disclosed phytase molecules—either alone or in combination with other reagents (including but not limited to enzymes, including proteases)—are serviceable not only in this application (e.g., for prevention of the unwanted sludge) but also in other applications where phytate hydrolysis is desirable.

The supplementation of diets with antibiotic substances has many beneficial results in livestock production. For example, in addition to its role as a prophylactic means to ward off disease, the administration of exogenous antibiotics has been shown to increase growth rates by upwards of 3-5%. The mechanism of this action may also involve—in part—an alteration in the digestive flora environment of farmed animals, resulting in a microfloral balance that is more optimal for nutrient absorption.

However, a significant negative effect associated with the overuse of antibiotics is the danger of creating a repository of pathogenic antibiotic-resistant microbial strains. This danger is imminent, and the rise of drug-resistant pathogens in humans has already been linked to the use of antibiotics in livestock. For example, Avoparcin, the antibiotic used in animal feeds, was banned in many places in 1997, and animals are now being given another antibiotic, virginiamycin, which is very similar to the new drug, Synercid®, used to replace vancomycin in human beings. However, studies have already shown that some enterococci in farm animals are resistant to Synercid®. Consequently, undesired tolerance consequences, such as those already seen with Avoparcin and vancomycin, are likely to reoccur no matter what new antibiotics are used as blanket prophylactics for farmed animals. Accordingly, researchers are calling for tighter controls on drug use in the industry.

The increases in growth rates achieved in animals raised on foodstuffs supplemented with the instantly disclosed phytase molecules matches—if not exceeds —those achieved using antibiotics such as, for example, Avoparcin. Accordingly, the instantly disclosed phytase molecules—either alone or in combination with other reagents (including but not limited to enzymes, including proteases)—are serviceable not only in this application (e.g., for increasing the growth rate of farmed animals) but also in other applications where phytate hydrolysis is desirable.

An environmental consequence is that the consumption of phytate-containing foodstuffs by any organism species that is phytase-deficient—regardless of whether the foodstuffs are supplemented with minerals—leads to fecal pollution resulting from the excretion of unabsorbed minerals. This pollution has a negative impact not only on the immediate habitat but consequently also on the surrounding waters. The environmental alterations occur primarily at the bottom of the food chain, and therefore have the potential to permeate upwards and throughout an ecosystem to effect permanent and catastrophic damage—particularly after years of continual pollution. This problem has the potential to manifest itself in any area where concentrated phytate processing occurs—including in vivo (e.g. by animals in areas of livestock production, zoological grounds, wildlife refuges, etc.) and in vitro (e.g. in commercial corn wet milling, ceral steeping processes, etc.) processing steps.

The decision to use exogenously added phytase molecules—whether to fully replace or to augment the use of exogenously administered minerals &/or antibiotics—ultimately needs to pass a test of financial feasibility & cost effectiveness by the user whose livelihood depends on the relevant application, such as livestock production.

Consequently, there is a need for means to achieve efficient and cost effective hydrolysis of phytate in various applications. Particularly, there is a need for means to optimize the hyrolysis of phytate in commercial applications. In a particular aspect, there is a need to optimize commercial treatment methods that improve the nutritional offerings of phytate-containing foodstuffs for consumption by humans and farmed animals.

Previous reports of recombinant phytases are available, but their inferior activities are eclipsed by the newly discovered phytase molecules of instant invention. Accordingly, the instantly disclosed phytase molecules are counted upon to provide substantially superior commercial performance than previously identified phytase molecules, e.g. phytase molecules of fungal origin.

Phytate occurs as a source of stored phosphorous in virtually all plant feeds (Graf (Ed.), 1986). Phytic acid forms a normal part of the seed in cereals and legumes. It functions to bind dietary minerals that are essential to the new plant as it emerges from the seed. When the phosphate groups of phytic acid are removed by the seed enzyme phytase, the ability to bind metal ions is lost and the minerals become available to the plant. In livestock feed grains, the trace minerals bound by phytic acid are largely unavailable for absorption by monogastric animals, which lack phytase activity.

Although some hydrolysis of phytate occurs in the colon, most phytate passes through the gastrointestinal tract of monogastric animals and is excreted in the manure contributing to fecal phosphate pollution problems in areas of intense livestock production. Inorganic phosphorous released in the colon has an appreciably diminished nutritional value to livestock because inorganic phosphorous is absorbed mostly—if not virtually exclusively—in the small intestine. Thus, an appreciable amount of the nutritionally important dietary minerals in phytate is unavailable to monogastric animals.

In sum, phytate-associated nutrients are comprised of not only phosphate that is covalently linked to phytate, but also other minerals that are chelated by phytate as well. Moreover, upon injestion, unhydrolyzed phytate may further encounter and become associated with additional minerals. The chelation of minerals may inhibit the activity of enzymes for which these minerals serve as co-factors.

Conversion of phytate to inositol and inorganic phosphorous can be catalyzed by microbial enzymes referred to broadly as phytases. Phytases such as phytase #EC 3.1.3.8 are capable of catalyzing the hydrolysis of myo-inositol hexaphosphate to D-myo-inositol 1,2,4,5,6-pentaphosphate and orthophosphate. Certain fungal phytases reportedly hydrolyze inositol pentaphosphate to tetra-, tri-, and lower phosphates. E.g., *A. ficuum* phytases reportedly produce mixtures of myoinositol di- and mono-phosphates (Ullah, 1988). Phytase-producing microorganisms are comprised of bacteria such as *Bacillus subtilis* (Powar and Jagannathan, 1982) and *Pseudomonas* (Cosgrove, 1970); yeasts such as *Sacchoromyces cerevisiae* (Nayini and Markakis, 1984); and fungi such as *Aspergillus terreus* (Yamada et al., 1968).

Acid phosphatases are enzymes that catalytically hydrolyze a wide variety of phosphate esters and usually exhibit pH optima below 6.0 (Igarashi & Hollander, 1968). E.g., #EC 3.1.3.2 enzymes catalyze the hydrolysis of orthophosphoric monoesters to orthophosphate products. An acid phosphatase has reportedly been purified from *A. ficuum*. The deglycosylated form of the acid phosphatase has an apparent molecular weight of 32.6 kDa (Ullah et al., 1987).

Phytase and less specific acid phosphatases are produced by the fungus *Aspergillus ficuum* as extracellular enzymes (Shieh et al., 1969). Ullah reportedly purified a phytase from wild-type *A. ficuum* that had an apparent molecular weight of 61.7 kDA (on SDS-PAGE; as corrected for glycosylation); pH optima at pH 2.5 and pH 5.5; a Km of about 40 $\mu$m; and, a specific activity of about 50 U/mg (Ullah, 1988). PCT patent application WO 91/05053 also reportedly discloses isolation and molecular cloning of a phytase from *Aspergillus ficuum* with pH optima at pH 2.5 and pH 5.5, a Km of about 250 $\mu$m, and specific activity of about 100 U/mg protein.

Summarily, the specific activity cited for these previously reported microbial enzymes has been approximately in the range of 50-100 U/mg protein. In contrast, the phytase activity disclosed in the instant invention has been measured to be approximately 4400 U/mg. This corresponds to about a 40-fold or better improvement in activity.

The possibility of using microbes capable of producing phytase as a feed additive for monogastric animals has been reported previously (U.S. Pat. No. 3,297,548 Shieh and Ware; Nelson et al., 1971). The cost-effectiveness of this approach has been a major limitation for this and other commercial applications. Therefore improved phytase molecules are highly desirable.

Microbial phytases may also reportedly be useful for producing animal feed from certain industrial processes, e.g., wheat and corn waste products. In one aspect, the wet milling process of corn produces glutens sold as animal feeds. The addition of phytase may reportedly improve the nutritional value of the feed product. For example, the use of fungal phytase enzymes and process conditions (t~50° C. and pH ~5.5) have been reported previously in (e.g. EP 0 321 004). Briefly, in processing soybean meal using traditional steeping methods, i.e., methods without the addition of exogenous phytase enzyme, the presence of unhydrolyzed phytate reportedly renders the meal and wastes unsuitable for feeds used in rearing fish, poultry and other non-ruminants as well as calves fed on milk. Phytase is reportedly useful for improving the nutrient and commercial value of this high protein soy material (see Finase Enzymes by Alko, Rajamäki, Finland). A combination of fungal phytase and a pH 2.5 optimum acid phosphatase form *A. niger* has been used by Alko, Ltd as an animal feed supplement in their phytic acid degradative product Finas F and Finase S. However, the cost-effectiveness of this approach has remained a major limitation to more widespread use. Thus a cost-effective source of phytase would greatly enhance the value of soybean meals as an animal feed (Shieh et al., 1969).

To solve the problems disclosed, the treatment of foodstuffs with exogenous phytase enzymes has been proposed, but this approach was not been fully optimized, particularly with respect to feasibility and cost efficiency. This optimization requires the consideration that a wide range of applications exists, particularly for large scale production. For example, there is a wide range of foodstuffs, preparation methods thereof, and species of recipient organisms.

In a particular exemplification, it is appreciated that the manufacture of fish feed pellets requires exposure of ingredients to high temperatures &/or pressure in order to produce pellets that do not dissolve &/or degrade prematurely (e.g. e.g. prior to consumption) upon subjection to water. It would thus be desirable for this manufacturing process to obtain additive enzymes that are stable under high temperature and/or pressure conditions. Accordingly it is appreciated that distinct phytases may be differentially preferable or optimal for distinct applications.

In sum, there is a need for novel, highly active, physiologically effective, and economical sources of phytase activity. Specifically, there is a need to identify novel phytases that: a) have superior activities under one or more specific applications, and are thus serviceable for optimizing these specific applications; b) are serviceable as templates for directed evolution to achieve even further improved novel molecules; and c) are serviceable as tools for the identification of additional related molecules by means such as hybridization-based approaches.

SUMMARY OF THE INVENTION

The invention provides a formulation or a pharmaceutical composition comprising at least one polypeptide having phytase activity, wherein the polypeptide comprises: (a) a polypeptide encoded by a nucleic acid comprising a nucleotide sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; or, 1016 is G; or, any combination thereof, wherein the polynucleotide encodes a phytase; (b) a polypeptide encoded by a nucleic acid comprising a nucleotide sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; and 1016 is G; (c) a polypeptide having an amino acid sequence as set forth in SEQ ID NO:8 and having one or more amino acid modifications selected from W68E, Q84W, A95P, K97C, S168E, R181Y, N226C, Y277D or any combination thereof, wherein the polypeptide has phytase activity; (d) a polypeptide having an amino acid sequence as set forth in SEQ ID NO:8 and having the amino acid modifications W68E, Q84W, A95P, K97C, S1168E, R181Y, N226C, Y277D, wherein the polypeptide has phytase activity; (e) a polypeptide encoded by a nucleic acid comprising a nucleotide sequence as set forth in SEQ ID NO:1; (f) a polypeptide having an amino acid sequence as set forth in SEQ ID NO:2; or, (g) a combination of (a), (b), (c), (d), (e) or (f).

In one aspect, the formulation is a dietary supplement, or, a pharmaceutical composition. In one aspect, the formulation or pharmaceutical composition further comprises at least one vitamin, at least one additional enzyme, at least one mineral or metal, or at least one herb or plant extract, at least one amino acid or amino acid derivative, or any combination thereof. The mineral or metal can be aluminum, antimony, barium, beryllium, bismuth, boron, bromide, bromine, cadmium, calcium, cerium, cesium, chloride, chromium, cobalt, copper, dysprosium, erbium, europium, fluoride, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, promethium, rhenium, rhodium, rubidium, ruthenium, samarium, scandium, selenium, silicon, silver, sodium, strontium, sulfur, tantalum, tellurium, terbium, thorium, thulium, tin, titanium, tungsten, vanadium, ytterbium, yttrium, zinc, zirconium or any combination thereof. In one aspect, the formulation or pharmaceutical composition further comprises a composition comprising a diatomaceous earth, charcoal, choline, inositol, biotin, PABA, Alpha-Lipoic Acid, a carotenoid, beta carotene, coenzyme Q10, chondroitin, melatonin, lecithin, brewer's yeast or a combination thereof The herb or plant extract can comprise an alfalfa, a ginseng, American ginseng, Asian red ginseng, Asian white ginseng, Siberian ginseng, Brazilian ginseng, astragalus, bilberry, black cohosh, cascara sagrada, cat's claw, cayenne, dong quai, echinacea, eucalyptus, feverfew, garlic, ginkgo biloba, goldenseal, gotu kola, horsetail, maca, a mushroom, Maitake mushroom, Reishi mushroom, Shuitake mushroom, leuzea, rhodiola, milk thistle, noni, pau d'arco, papaya, pygeum, saw palmetto, schizandra, senna, suma, wild yam, willow, yucca, wheat grass, barley grass, parsley, broccoli, acerola cherries, aloe vera, quercitin, pine bark, grape seed, green tea, red wine, grapefruit extract, ginger, oat straw, sarsaparilla, an oil, walnut oil, safflower oil, soybean oil, peanut oil, a fish oil, salmon oil, evening primrose oil, borage oil, bee pollen, bee propolis, royal jelly, a bran, oat bran, wheat bran, a fiber, soy, psyllium, apple pectin, a protein, egg protein, milk protein, soy protein, rice protein, whey, algae, spirulina, Chlorella, dulse, kelp, D. salina or a combination thereof. The probiotic can comprise a *Lactobacillus* species, *L. acidophilus,. L. bifidus, L. sporogenes, L. casei, L. rhamnosus, L. plantarum, S. thermophilus*, a *Bifidobacterium* species, an *Escherichia*, an *Enterococcus*, a *Bacillus* or a *Saccharomyces* species. The additional enzyme can be a phytase, an amylase, a bromelain, a cellulase, a chymopapain, a diastase, a glucoamylase, a hemicellulase, a hyaluronidase, an invertase, a lactase, a lipase, a maltase, a pancreatin, a papain, a pectinase, a pepsin, a plasmin, a protease, a rennin or any combination thereof The vitamin can comprise vitamin B, Thiamine (Vitamin B1), Riboflavin (Vitamin B2), Nicotinic acid (Niacin, Vitamin B3), Pantothenic acid (Vitamin B5), Pyridoxine (Vitamin B6), B7, Folic acid (Vitamin B9), Cyanocobalamin (Vitamin B12), vitamin C, a vitamin D, vitamin D1, vitamin D2, vitamin D3, vitamin E, a vitamin K, vitamin K1, vitamin K2, vitamin G, vitamin H, vitamin P or any combination thereof. The amino acid or amino acid derivative can comprise Isoleucine, Leucine, Lysine, Phenylalanine, Threonine, Tryptophan, Valine, Methionine, Cysteine, Alanine, Arginine, Aspartic Acid, Glutamic Acid, Glycine, Histidine, Proline, Seine, Asparagine, Glutamine, Tyrosine, taurine, glucosamine or any combination thereof. In one aspect, the formulation or pharmaceutical composition further comprises vitamin D3 or calcium or both. In one aspect, the formulation or pharmaceutical composition further comprises potassium, glucose, CaCl.sub.2 or a combination thereof. In one aspect, the formulation or pharmaceutical composition further comprises at least one enzyme selected from the group consisting of α-galactosidases, β-galactosidases, lactases, phytases, β-glucanases, endo-β-1,4-glucanases and endo-β1,3(4)-glucanases, cellulases, xylosidases, galactanases, arabinogalactan endo-1,4-β-galactosidases and arabinogalactan endo-1,3-β-galactosidases, endoglucanases, endo-1,2-β-glucanase-, endo-1, 3-α-glucanase, endo-1,3-β-glucanase, pectin degrading enzymes, pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, α-galacturonisidases, mannanases, .beta.-mannosidases, mannan acetyl esterases, xylan acetyl esterases, proteases, xylanases, arabinoxylanases, lipases, phospholipases or a cutinase. In one aspect, the formulation or pharmaceutical composition comprises a powder, a tablet, a concentrate, a geltab, a capsule, a spray, an aerosol, a lotion, an adhesive patch or a drink.

The invention provides pharmaceutical composition comprising at least one polypeptide having phytase activity and a pharmaceutically acceptable excipient, wherein the polypeptide comprises: (a) a polypeptide encoded by a nucleic acid comprising a nucleotide sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; or, 1016 is G; or, any combination thereof, wherein the polynucleotide encodes a phytase; (b) a polypeptide encoded by a nucleic acid comprising a nucleotide sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; and 1016 is G; (c) a polypeptide having an amino acid sequence as set forth in SEQ ID NO:8 and having one or more amino acid modifications selected from W68E, Q84W, A95P, K97C, S168E, R181Y, N226C, Y277D or any combination thereof, wherein the polypeptide has phytase activity; (d) a polypeptide having an amino acid sequence as set forth in SEQ ID NO:8 and having the amino acid modifications W68E, Q84W, A95P, K97C, S168E, R181Y, N226C, Y277D, wherein the polypeptide has phytase activity; (e) a polypeptide encoded by a nucleic acid comprising a nucleotide sequence as set forth in SEQ ID NO:1; (f) a polypeptide having an amino acid sequence as set forth in SEQ ID NO:2; or, (g) a combination of (a), (b), (c), (d), (e) or (f). In one aspect, the formulation or pharmaceutical composition is formulated for oral delivery. In one aspect, the formulation or pharmaceutical composition is formulated as a pill, a tablet, a capsule, a spray, an aerosol or a powder.

The invention provides a kit comprising a formulation of the invention, or a pharmaceutical composition of the invention, and instructions on using the formulation or the pharmaceutical composition.

The invention provides immobilized phytases comprising: (a) a polypeptide encoded by a nucleic acid comprising a nucleotide sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; or, 1016 is G; or, any combination thereof, wherein the polynucleotide encodes a phytase; (b) a polypeptide encoded by a nucleic acid comprising a nucleotide sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; and 1016 is G; (c) a polypeptide having an amino acid sequence as set forth in SEQ ID NO:8 and having one or more amino acid modifications selected from W68E, Q84W, A95P, K97C, S168E, R181Y, N226C, Y277D or any combination thereof, wherein the polypeptide has phytase activity; (d) a polypeptide having an amino acid sequence as set forth in SEQ ID NO:8 and having the amino acid modifications W68E, Q84W, A95P, K97C, S168E, R181Y, N226C, Y277D, wherein the polypeptide has phytase activity; (e) a polypeptide encoded by a nucleic acid comprising a nucleotide sequence as set forth in SEQ ID NO:1; (f) a polypeptide having an amino acid sequence as set forth in SEQ ID NO:2; or, (g) a combination of (a), (b), (c), (d), (e) or (f). In one aspect, the polypeptide is immobilized to a bead, for example, a polysorb bead or a polystyrene bead, or equivalent bead.

The invention provides a dietary supplement comprising the immobilized phytase of the invention. In one aspect, the invention provides a pharmaceutical composition comprising the immobilized phytase of the invention.

The invention provides fertilizer or soil additives comprising at least one immobilized phytase of the invention. The invention provides fertilizer or soil additives comprising at least one polypeptide of the invention having phytase activity. The invention provides liquid supplements for preventing muscle cramps comprising a formulation of the invention or a pharmaceutical composition of the invention. In one aspect, the formulation or pharmaceutical composition can further comprise glucose, potassium, sodium or calcium.

The invention provides hydrating agents comprising a formulation or pharmaceutical composition of the invention. The hydrating agents can further comprise glucose, potassium, sodium or calcium.

The invention provides tissue culture or cell culture media or cell culture media additive comprising at least one polypeptide of the invention having phytase activity.

The invention provides plant food additives comprising at least one polypeptide of the invention having phytase activity.

The invention provides methods for treating or preventing osteoporosis in an individual comprising administering to an individual an effective amount of a formulation or pharmaceutical composition of the invention.

The invention provides method for treating or preventing bone loss in an individual comprising administering to an individual an effective amount of a formulation or pharmaceutical composition of the invention.

The invention provides methods for reversing bone loss or osteoporosis in an individual comprising administering to an individual an effective amount of a formulation or pharmaceutical composition of the invention.

The invention provides methods for preventing muscle cramps comprising administering to an individual an effective amount of a formulation or pharmaceutical composition of the invention.

The invention provides methods for reducing pollution and increasing nutrient availability in an environment or environmental sample by degrading environmental phytic acid comprising applying to the environmental or environmental sample an effective amount of a composition comprising at least one polypeptide of the invention having phytase activity. In one aspect of the methods, the environment or environmental sample comprises a soil or a body of water, for example, a well, a pond, a lake, a river, an aquifer or a reservoir. In one aspect of the methods, the environment or environmental sample comprises a sewage, a sewage effluent, a landfill or a manure pond.

The present invention provides a polynucleotide and a polypeptide encoded thereby which has been identified as a phytase enzyme having phytase activity. In accordance with one aspect of the present invention, there is provided a novel recombinant enzyme, as well as active fragments, analogs and derivatives thereof.

A deposit of the gene designated 819PH59 in *E. coli* XL1-Blue has been made with and accepted by the ATCC located at 10801 University Blvd., Manassas, Va. 20110-2209, on Nov. 26, 2002. The Patent Deposit Designation is PTA-4822.

In one aspect, this invention relates to the use of recombinant phytase molecules of bacterial origin that are serviceable for improving the nutritional value of phytate-containing foodstuffs. Previous publications have disclosed the use of fungal phytases, but the use of bacterial phytases for this purpose is novel.

In one aspect, this invention relates to the use of newly identified recombinant phytase molecules of *E. coli* origin that are serviceable for improving the nutritional value of phytate-containing foodstuffs.

This use is comprised of employing the newly identified molecules to hydrolyze phytate in foodstuffs. Hydrolysis may occur before ingestion or after ingestion or both before and after injestion of the phytate. This application is particularly relevant, but not limited, to non-ruminant organisms and includes the expression of the disclosed novel phytase molecules in transformed hosts, the contacting of the disclosed novel phytase molecules with phytate in foodstuffs and other materials, and the treatment of animal digestive systems with the disclosed novel phytase molecules.

Additionally, hydrolysis may occur independently of consumption, e.g. in an in vitro application, such as in a reaction vessel. Thus, the treatment of phytate-containing materials includes the treatment of a wide range of materials, including ones that are not intended to be foodstuffs, e.g. the treatment of excrementary (or fecal) material.

In one aspect, molecules of the present invention include a recombinant phytase isolated from *Escherichia coli* B that improves the efficiency of release of phosphorous from phytate and the salts of phytic acid when compared to previously identified fungal phytases.

In one aspect, there is provided a phytase enzyme that is serviceable for incorporation into foodstuffs. In one aspect, there is provided a phytase enzyme that is serviceable for improving the nutritional value of phytate-containing foodstuffs. More specifically still, there is provided a phytase enzyme that, when applied to phytate-containing foodstuffs, measurably improves the growth performance of an organism that consumes it. It is theorized that the beneficial mechanism of action of the phytase activity is comprised appreciably if not substantially of the hydrolysis of phytate. It is provided that the beneficial action may occur before injestion or alternatively after injestion or alternatively both before and after injestion of the phytate-containing foodstuff. In the case where the beneficial action occurs after injestion, it is an object of the present invention to provide a phytase enzyme that has activity that is retained upon consumption by non-ruminant organisms.

In one aspect, there are provided isolated nucleic acid molecules encoding the enzyme of the present invention—including mRNA, DNA, cDNA, genomic DNA—as well as active derivatives, analogs and fragments of such enzyme.

In one aspect, there is provided a process for producing such polypeptides by recombinant techniques comprising culturing recombinant prokaryotic and/or eukaryotic host cells, containing a nucleic acid sequence encoding an enzyme of the present invention, under conditions promoting expression of the enzyme and subsequent recovery of the enzyme.

In one aspect, there is provided a process for expressing such enzymes, or polynucleotides encoding such enzymes in transgenic plants or plant organs and methods for the production of such plants. This is achievable by introducing into a plant an expression construct comprised of a nucleic acid sequence encoding such phytase enzymes.

In one aspect, there is provided a process for utilizing such enzymes, or polynucleotides encoding such enzymes for use in commercial processes, such as, for example, processes that liberate minerals from phytates in plant materials either in vitro, i.e., in feed treatment processes, or in vivo, i.e., by administering the enzymes to animals.

In one aspect, there are provided foodstuffs made by the disclosed feed treatment processes.

In accordance with yet a further aspect of the present invention, there are provided a processes for utilizing such enzymes, or polynucleotides encoding such enzymes, for in vitro purposes related to research, discovery, and development. In a non-limiting exemplification, such processes comprise the generation of probes for identifying and isolating similar sequences which might encode similar enzymes from other organisms.

In a particular non-limiting exemplification, there are also provided processes for generating nucleic acid probes comprising nucleic acid molecules of sufficient length to specifically hybridize to a nucleic acid sequence of the present invention. By way of preferred exemplification, hybridization-based uses of these probes include, but are by no means limited to, PCR, Northern and Southern types of hybridizations, RNA protection assays, and in situ types of hybridizations. The uses of the instantly disclosed molecules further include, in a non-limiting manner, diagnostic applications.

In accordance with a non-limiting exemplification, these processes comprise the generation of antibodies to the disclosed molecules, and uses of such antibodies, including, for example, for the identification and isolation of similar sequences in enzymes from other organisms. In another non-limiting examplification, these processes include the use of the present enzymes as templates for directed evolution, comprising the generation of novel molecules by followed by screening-based approaches for discovering of progeny molecules with improved properties.

Also provided is a transgenic non-human organism whose genome comprises a heterologous nucleic acid sequence encoding a polypeptide having phytase activity, wherein the transgene results in expression of a phytase polypeptide.

The invention also provides phytase encoding polynucleotides having a nucleotide sequence substantially identical to SEQ ID NO:7, and having a modified nucleotide sequence selected from nucleotide 389 is G; 390 is A; nucleotide 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; 1016 is G, or any combination thereof.

Further, the invention provides a polynucleotide having a nucleotide sequence substantially identical to SEQ ID NO:7, and having a modified nucleotide sequence selected from nucleotide 389 is G and 390 is A; nucleotide 437 is T, 438 is G and 439 is G; 470 is C and 472 is T; 476 is T, 477 is G, and 478 is T; 689 is G, 690 is A and 691 is G; 728 is T, 729 is A, and 730 is T; 863 is T and 864 is G; 1016 is G, or any combination thereof. The later sequence is exemplified in SEQ ID NO:9 and the corresponding amino acid sequence is SEQ ID NO:10.

These and other aspects of the present invention should be apparent to those skilled in the art from the teachings herein.

All publications, patents, patent applications, GenBank sequences and ATCC deposits, cited herein are hereby expressly incorporated by reference for all purposes.

BRIEF DESCRIPTION OF THE DRAWINGS

The following drawings are illustrative of embodiments of the invention and are not meant to limit the scope of the invention as encompassed by the claims.

FIGS. 1a and 1b show the nucleotide and deduced amino acid sequences an exemplary enzyme of the present invention. Sequencing was performed using a 378 automated DNA sequencer (Applied Biosystems, Inc.).

FIGS. 7A and 7B show the nucleotide sequence of *E. coli* appA phytase (SEQ ID NO:7, encoding the *E. coli* appA wild type phytase SEQ ID NO:8).

FIG. 8 shows the amino acid sequence of *E. coli* appA phytase (SEQ ID NO:8) and an exemplary phytase of the invention having a sequence as set forth in SEQ ID NO:10 (a modified phytase).

DETAILED DESCRIPTION OF THE INVENTION

Figure 2A:
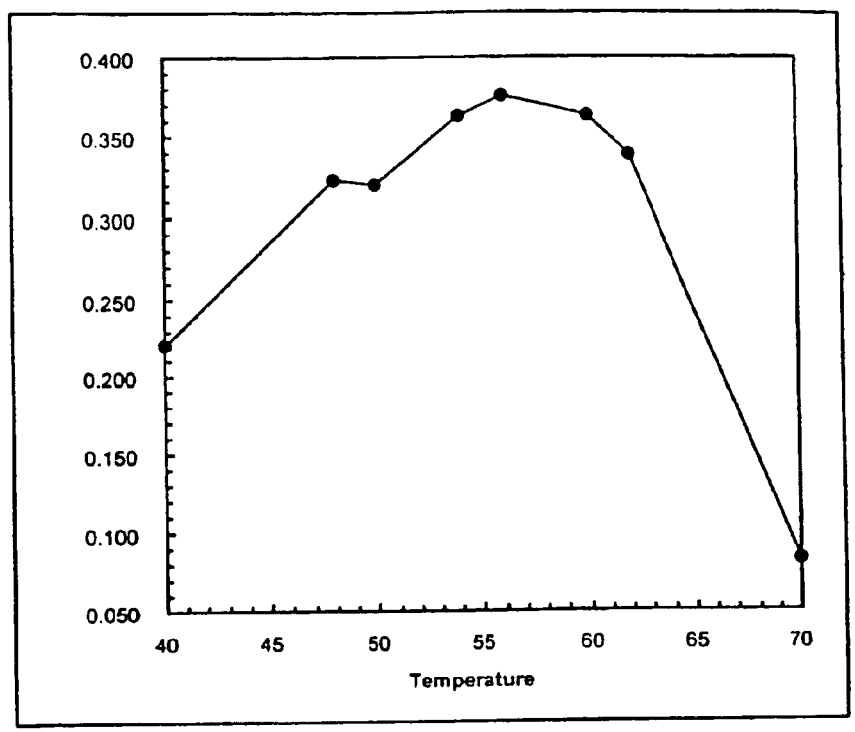
FIGS. 2A and 2B show the pH and temperature profile and stability data for the phytase enzyme of the present invention, as described in detail in Example 6, below.

The present invention provides a thermally stable phytase having a polynucleotide and polypeptide sequence modified in such a way as to provide a phytase having increased thermal stability as compared with other phytase enzymes. Expression of this new phytase in *S. pombe* or *P. pastoris*, for example, resulted in the production of glycosylated variants that exhibited additional thermal tolerance.

The present invention provides purified a recombinant phytase enzyme, shown in FIGS. 1a and 1b. Additionally, the present invention provides isolated nucleic acid molecules (polynucleotides) which encode for the mature enzyme having the deduced amino acid sequence of FIGS. 1a and 1b. The invention also provides an exemplary phytase of the invention having a sequence as set forth in SEQ ID NO:10, and encoded by, e.g., SEQ ID NO:9 (a modified phytase sequence) as shown in FIG. 8 and SEQ ID NO:9 and 10.

The phytase molecules of the instant invention are novel with respect to their structures. Additionally, the instant phytase molecules are patentably novel with respect to activity. For example, using an assay (as described in Food Chemicals Codex, $4^{th}$ Ed.) the activity of the instant phytase enzyme was demonstrated to be far superior in comparison to a fungal (*Aspergillus*) phytase control. Specifically, a plurality of experiments showed the *E. coli* phytase to have an activity of about 4400 units/mg and the *Aspergillus* phytase to have an activity of about 105 units/mg. This corresponds to more than a 40-fold difference in activity. In order to facilitate understanding of the examples provided herein, certain frequently occurring methods and/or terms will be described.

The term "antibody," as used herein, refers to intact immunoglobulin molecules, as well as fragments of immunoglobulin molecules, such as Fab, Fab', (Fab')$_2$, Fv, and SCA fragments, that are capable of binding to an epitope of a phytase polypeptide. These antibody fragments, which retain some ability to selectively bind to the antigen (e.g., an phytase antigen) of the antibody from which they are derived, can be made using well known methods in the art (see, e.g., Harlow and Lane, supra), and are described further, as follows.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) An single chain antibody ("SCA") is a genetically engineered single chain molecule containing the variable region of a light chain and the variable region of a heavy chain, linked by a suitable, flexible polypeptide linker.

The term "degrading effective" amount refers to the amount of enzyme which is required to degrade at least 50% of the phytate, as compared to phytate not contacted with the enzyme. In one aspect, at least 80% of the phytate is degraded.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

As used in this invention, the term "epitope" refers to an antigenic determinant on an antigen, such as a phytase polypeptide, to which the paratope of an antibody, such as an phytase-specific antibody, binds. Antigenic determinants usually consist of chemically active surface groupings of molecules, such as amino acids or sugar side chains, and can have specific three-dimensional structural characteristics, as well as specific charge characteristics.

The terms "fragment", "derivative" and "analog" when referring to the enzyme of FIGS. 1a and 1b comprise a enzyme which retains at least one biological function or activity that is at least essentially same as that of the reference enzyme. Furthermore, the terms "fragment", "derivative" or "analog" are exemplified by a "pro-form" molecule, such as a low activity proprotein that can be modified by cleavage to produce a mature enzyme with significantly higher activity.

The term "gene" means the segment of DNA involved in producing a polypeptide chain; it includes regions preceding and following the coding region (leader and trailer) as well as intervening sequences (introns) between individual coding segments (exons).

The term "isolated" means that the material is removed from its original environment (e.g., the natural environment if it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides could be part of a vector and/or such polynucleotides or enzymes could be part of a composition, and still be isolated in that such vector or composition is not part of its natural environment.

By "isolated nucleic acid" is meant a nucleic acid, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

"Ligation" refers to the process of forming phosphodiester bonds between two double stranded nucleic acid fragments (Sambrook et al., 1989). Unless otherwise provided, ligation may be accomplished using known buffers and conditions with 10 units of T4 DNA ligase ("ligase") per 0.5 µg of approximately equimolar amounts of the DNA fragments to be ligated.

As used herein, a "nucleic acid molecule" is comprised of at least one nucleotide base or one nucleotide base pair, depending on whether it is single-stranded or double-stranded, respectively. Furthermore, a nucleic acid molecule may belong exclusively or chimerically to any group of nucleotide-containing molecules, as exemplified by, but not limited to, the following groups of nucleic acid molecules: RNA, DNA, genomic nucleic acids, non-genomic nucleic acids, naturally occurring and not naturally occurring nucleic acids, and synthetic nucleic acids. This includes, by way of non-limiting example, nucleic acids associated with any organelle, such as the mitochondria, ribosomal RNA, and nucleic acid molecules comprised chimerically of one or more components that are not naturally occurring along with naturally occurring components.

Additionally, a "nucleic acid molecule" may contain in part one or more non-nucleotide-based components as exemplified by, but not limited to, amino acids and sugars. Thus, by way of example, but not limitation, a ribozyme that is in part nucleotide-based and in part protein-based is considered a "nucleic acid molecule".

In addition, by way of example, but not limitation, a nucleic acid molecule that is labeled with a detectable moiety, such as a radioactive or alternatively a non-radioactive label, is likewise considered a "nucleic acid molecule".

The terms "nucleic acid sequence coding for" or a "DNA coding sequence of" or a "nucleotide sequence encoding" a particular enzyme—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases where elements necessary to initiate transcription at levels detectable above background bind. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

The terms "nucleic acid encoding an enzyme (protein)" or "DNA encoding an enzyme (protein)" or "polynucleotide encoding an enzyme (protein)" and other synonymous terms encompasses a polynucleotide which includes only coding sequence for the enzyme as well as a polynucleotide which includes additional coding and/or non-coding sequence.

In one preferred embodiment, a "specific nucleic acid molecule species" is defined by its chemical structure, as exemplified by, but not limited to, its primary sequence. In another preferred embodiment, a specific "nucleic acid molecule species" is defined by a function of the nucleic acid species or by a function of a product derived from the nucleic acid species. Thus, by way of non-limiting example, a "specific nucleic acid molecule species" may be defined by one or more activities or properties attributable to it, including activities or properties attributable its expressed product.

The instant definition of "assembling a working nucleic acid sample into a nucleic acid library" includes the process of incorporating a nucleic acid sample into a vector-based collection, such as by ligation into a vector and transformation of a host. A description of relevant vectors, hosts, and other reagents as well as specific non-limiting examples thereof are provided hereinafter. The instant definition of "assembling a working nucleic acid sample into a nucleic acid library" also includes the process of incorporating a nucleic acid sample into a non-vector-based collection, such as by ligation to adaptors. In one aspect the adaptors can anneal to PCR primers to facilitate amplification by PCR.

Accordingly, in a non-limiting embodiment, a "nucleic acid library" is comprised of a vector-based collection of one or more nucleic acid molecules. In another preferred embodiment a "nucleic acid library" is comprised of a non-vector-based collection of nucleic acid molecules. In yet another preferred embodiment a "nucleic acid library" is comprised of a combined collection of nucleic acid molecules that is in part vector-based and in part non-vector-based. In one aspect, the collection of molecules comprising a library is searchable and separable according to individual nucleic acid molecule species.

The present invention provides a "nucleic acid construct" or alternatively a "nucleotide construct" or alternatively a "DNA construct". The term "construct" is used herein to describe a molecule, such as a polynucleotide (e.g., a phytase polynucleotide) may optionally be chemically bonded to one or more additional molecular moieties, such as a vector, or parts of a vector. In a specific—but by no means limiting— aspect, a nucleotide construct is exemplified by a DNA expression construct suitable for the transformation of a host cell.

"Oligonucleotides" refers to either a single stranded polydeoxynucleotide or two complementary polydeoxynucleotide strands which may be chemically synthesized. Such synthetic oligonucleotides may or may not have a 5' phosphate. Those that do not will not ligate to another oligonucleotide without adding a phosphate with an ATP in the presence of a kinase. A synthetic oligonucleotide will ligate to a fragment that has not been dephosphorylated.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences are ultimately processed to produce the desired protein.

The term "phytase-specific probe", in the context of this method of invention, refers to probes that bind to nucleic acids encoding phytase polypeptides, or to complementary sequences thereof, to a detectably greater extent than to nucleic acids encoding other enzymes, or to complementary sequences thereof.

In a strict sense, the terms "phytate", "phytic acid", and "phytin", may be differentiated as folllows: "phytate" refers to an anionic form of phytic acid; "phytic acid" refers to inositol hexaphosphate, a compound that occurs naturally in plants, including particularly plant leaves, and that may serve as a substrate for the enzyme phytase; and "phytin" refers to a salt of phytic acid, such as a calcium-magnesium salt of phytic acid. It is understood, accordingly, that "phytate", "phytic acid", and "phytin" are chemically related and interconvertible forms having a shared chemical structure. As used herein, therefore, "phytate", "phytic acid", and "phytin" are interchangeable terms in as much as they are highly related, similar, chemically interconvertible, and may all (either with or without the chemical interconversion) be subject to degredation by the novel phytase enzyme disclosed instantly. Accordingly, where only one of the terms "phytate", "phytic acid", or "phytin" is used in the descriptions of the methods disclosed herein, it is understood to function as a representative term that further refers to any substrate of the enzyme phytase including "phytase", "phytic acid", and "phytin".

A "polynucleotide" is a molecule composed of 2 or more nucleotide bases or nucleotide base pairs.

A molecule having a "pre-form" or a "pro-form" refers to a molecule that undergoes any combination of one or more covalent and noncovalent chemical modifications (e.g. glycosylation, proteolytic cleavage, dimerization or oligomerization, temperature-induced or pH-induced conformational change, association with a co-factor, etc.) en route to attain a more mature molecular form having a property difference (e.g. an increase in activity) in comparison with the reference pro-form molecule. When a precursor molecule in "pre-form" or in "pro-form" is able to undergo two or more chemical modification (e.g. two proteolytic cleavages, or a proteolytic cleavage and a change in glycosylation) en route to the production of a mature molecule, the term "pre-pro-form" may also be used in reference to the precursor molecule. Accordingly, a pre-pro-enzyme is an enzyme in "pre-pro-form". Likewise, a pre-pro hormone is a hormone in "pre-pro-form".

As used herein, the term "reagent" includes phytase molecules of the instant invention. In one aspect, such phytase molecules catalyze the hydrolysis of phytate to inositol and free phosphate with release of minerals from the phytic acid complex. An exemplary phytase molecule is a phytase derived from *Escherichia coli* B. This exemplary enzyme is shown in FIGS. 1a and 1b, SEQ ID NO:2. Additionally, as used herein, the term "reagent" includes substrate reagents molecules of the instant invention, such as phytate molecules. In one aspect, such phytate molecules are found in foodstuffs, potential foodstuffs, byproducts of foodstuffs (both in vitro byproducts and in vivo byproducts, e.g. ex vivo reaction products and animal excremental products), precursors of foodstuffs, and any other source of phytate.

"Recombinant" enzymes refer to enzymes produced by recombinant DNA techniques, i.e., produced from cells transformed by an exogenous DNA construct encoding the desired enzyme. "Synthetic" enzymes are those prepared by chemical synthesis.

As known in the art "similarity" between two enzymes is determined by comparing the amino acid sequence and its conserved amino acid substitutes of one enzyme to the sequence of a second enzyme. Similarity may be determined by procedures which are well-known in the art, for example, a BLAST program (Basic Local Alignment Search Tool at the National Center for Biological Information).

The members of a pair of molecules (e.g., an antibody-antigen pair or a nucleic acid pair) are said to "specifically bind" to each other if they bind to each other with greater affinity than to other, non-specific molecules. For example, an antibody raised against an antigen to which it binds more efficiently than to a non-specific protein can be described as specifically binding to the antigen. (Similarly, a nucleic acid probe can be described as specifically binding to a nucleic acid target if it forms a specific duplex with the target by base pairing interactions (see above).)

"Stringent hybridization conditions" means hybridization will occur only if there is at least 90% identity, or, at least 95% identity, or, at least 97% identity between the sequences. See Sambrook et al., 1989.

Also included in the invention are polypeptides having sequences that are "substantially identical" to the sequence of a phytase polypeptide, such as one of SEQ ID NO:1. A "substantially identical" amino acid sequence is a sequence that differs from a reference sequence or sequences only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine).

Additionally a "substantially identical" amino acid sequence is a sequence that differs from a reference sequence or sequences or by one or more non-conservative substitutions, deletions, or insertions, particularly when such a substitution occurs at a site that is not the active site the molecule, and provided that the polypeptide essentially retains its behavioural properties. For example, one or more amino acids can be deleted from a phytase polypeptide, resulting in modification of the structure of the polypeptide, without significantly altering its biological activity. For example, amino- or carboxyl-terminal amino acids that are not required for phytase biological activity can be removed. Such modifications can result in the development of smaller active phytase polypeptides.

The present invention provides a "substantially pure enzyme". The term "substantially pure enzyme" is used herein to describe a molecule, such as a polypeptide (e.g., a phytase polypeptide, or a fragment thereof) that is substantially free of other proteins, lipids, carbohydrates, nucleic acids, and other biological materials with which it is naturally associated. For example, a substantially pure molecule, such as a polypeptide, can be at least 60%, by dry weight, the molecule of interest. The purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

The present invention provides purified a recombinant enzyme that catalyzes the hydrolysis of phytate to inositol and free phosphate with release of minerals from the phytic acid complex. An exemplary purified enzyme is a phytase derived from *Escherichia coli* B. This exemplary enzyme is shown in FIGS. 1a and 1b, SEQ ID NO:2.

The enzymes of the present invention include, in addition to an enzyme of FIGS. 1a and 1b (in particular the mature enzyme), polypeptides having sequences that are "substantially identical" to the sequence of a phytase polypeptide, such as one of SEQ ID 1.

In one embodiment, the phytase enzyme of SEQ ID NO:2 of the present invention has a molecular weight of about 47,056 kilodaltons as measured by SDS-PAGE and inferred from the nucleotide sequence of the gene. The pI is 6.70. The pH and temperature profile and stability data for this enzyme is presented in FIG. 2. This purified enzyme may be used to catalyze the hydrolysis of phytate to inositol and free phosphate where desired. The phytase enzyme of the present invention has a high thermostability; thus it is particularly serviceable for raised temperature and/or pressure applications including, but not limited to, the preparation of fish foodstuff pellets that will not dissolve prematurely in water.

The phytase polypeptide included in the invention can have the amino acid sequences of the phytase shown in FIGS. 1a and 1b (SEQ ID NO:2). Phytase polypeptides, such as those isolated from *E. coli* B, can be characterized by catalyzing the hydrolysis of phytate to inositol and free phosphate with the release of minerals from the phytic acid complex.

Other phytase polypeptides used in the compositions (e.g., formulations, dietary supplements) and methods of the invention comprise phytases of the invention (e.g., a phytase having a sequence identity of at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 97.5%, 98%, 98.5%, 99%, 99.5%, or more, or complete (100%) sequence identity (i.e., homology) to SEQ ID NO:2 (a phytase polypeptide); SEQ ID NO:10 (a phytase polypeptide); a polypeptide having sequence as set forth in SEQ ID NO:8 and having at least one, or all, of the amino acid modifications W68E, Q84W, A95P, K97C, S168E, R181Y, N226C, Y277D, wherein the polypeptide has phytase activity) or other phytases, for example, the *E. coli* appA "wild type" phytase-encoding SEQ ID NO:7, or, a polypeptide sequence of SEQ ID NO:2 or the *E. coli* appA "wild type" phytase SEQ ID NO:8. The length of comparison in determining amino acid sequence homology can be, for example, at least 15 amino acids, and for example, at least 20, 25, 35, 40, 45, 50, 55, 60, 65, 70, 75, 80, 85, 90, 100 or more amino acids.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared, however a database of reference sequences can be used. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482, 1981, by the homology alignment algorithm of Needleman & Wunsch, J. Mol. Biol. 48:443, 1970, by the search for similarity method of person & Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (attem-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project. At least twenty-one other genomes have already been sequenced, including, for example, *M. genitalium* (Fraser et al., 1995), M. jannaschii (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, and *Arabadopsis* sp. Several databases containing genomic information annotated with some functional information are maintained by different organization, and are accessible via the internet.

One example of a useful algorithm is BLAST and BLAST 2.0 algorithms, which are described in Altschul et al., Nuc. Acids Res. 25:3389-3402, 1977, and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915, 1989) alignments (B) of 50, expectation (E) of 10, M=5, N=-4, and a comparison of both strands.

The BLAST algorithm also performs a statistical analysis of the similarity between two sequences (see, e.g., Karlin & Altschul, Proc. Natl. Acad. Sci. USA 90:5873, 1993). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, or, less than about 0.01, or, less than about 0.001.

In one embodiment, protein and nucleic acid sequence homologies are evaluated using the Basic Local Alignment Search Tool ("BLAST") In particular, five specific BLAST programs are used to perform the following task:

(1) BLASTP and BLAST3 compare an amino acid query sequence against a protein sequence database;
(2) BLASTN compares a nucleotide query sequence against a nucleotide sequence database;
(3) BLASTX compares the six-frame conceptual translation products of a query nucleotide sequence (both strands) against a protein sequence database;
(4) TBLASTN compares a query protein sequence against a nucleotide sequence database translated in all six reading frames (both strands); and
(5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is can be obtained from a protein or nucleic acid sequence database. High-scoring segment pairs can be identified (ie., aligned) by means of a scoring matrix, many of which are known in the art. In one aspect, the scoring matrix used is the BLOSUM62 matrix (Gonnet et al., Science 256:1443-1445, 1992; Henikoff and Henikoff, Proteins 17:49-61, 1993). The PAM or PAM250 matrices may also be used (see, e.g., Schwartz and Dayhoff, eds., 1978, *Matrices for Detecting Distance Relationships: Atlas of Protein Sequence and Structure*, Washington: National Biomedical Research Foundation). BLAST programs are accessible through the U.S. National Library of Medicine.

The parameters used with the above algorithms may be adapted depending on the sequence length and degree of homology studied. In some embodiments, the parameters may be the default parameters used by the algorithms in the absence of instructions from the user.

The present invention further relates to an enzyme which has the deduced amino acid sequence of FIGS. 1*a* and 1*b*, as well as analogs, derivatives, and fragments of such enzyme.

An analog, derivative, or fragment of the enzyme of FIGS. 1*a* and 1*b* may be (a) one in which one or more of the amino acid residues are substituted with an amino acid residue which is not encoded by the genetic code, or (b) one in which one or more of the amino acid residues includes a substituent group, or (c) one in which the mature enzyme is fused with another compound, such as a compound to increase the half-life of the enzyme (for example, polyethylene glycol), or (d) to provide a label or a tag, such as a 6×His tag or a green fluorescent protein tag, (e) one in which the additional amino acids are fused to the mature enzyme, such as a leader or secretory sequence or a sequence which is employed for purification of the mature enzyme or a proprotein sequence. Such analogs, derivatives, and fragments are deemed to be within the scope of those skilled in the art from the teachings herein.

A variant, e.g., a "fragment", "analog" or "derivative" enzyme, and reference enzyme may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, in a particular non-limiting exemplification, a substitution can be comprised of a substitution of one amino acid by another amino acid with a like property. In another particular non-limiting exemplification, a substitution can be comprised of a substitution of an amino acid by an unlike amino acid, where the change is non-inhibitory or silent or improved with respect to at least one enzyme property.

Additionally, in a non-limiting exemplification, an addition can be comprised of an addition either at the amino or the carboxy terminal of the protein or alternatively between the terminal sites, where the change is change is non-inhibitory or silent or improved with respect to at least one enzyme property.

In another particular non-limiting exemplification, a change can be comprised of a plurality of modifications, including substitutions, additions, deletions, fusions and/or truncations, in the enzyme encoded by the reference polynucleotide (SEQ ID NO:1, such that, irrespective of the effects of the individual modifications, when taken together as a set, the effect of the modifications is non-inhibitory or silent or improved with respect to at least one enzyme property.

In one aspect, a phytase variant retains substantially the same biological function and activity as the reference polypeptide from which it varies.

The term "variant" refers to polynucleotides or polypeptides of the invention modified at one or more base pairs, codons, introns, exons, or amino acid residues (respectively) yet still retain the biological activity of a phytase of the invention. Variants can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, Gene Site Saturation Mutagenesis™ (GSSM™) and any combination thereof as discussed more fully below. The invention also provides methods for modifying any phytase using these exemplary or other methods.

In accordance with an aspect of the present invention, there are provided isolated nucleic acid molecules (polynucleotides) which encode for the mature enzyme having the deduced amino acid sequence of FIGS. 1a and 1b.

The polynucleotide encoding SEQ ID NO:2 was originally isolated from genomic DNA recovered from *Escherichia coli* B as described below. It contains an open reading frame encoding a protein of 432 amino acid residues.

In accordance with another aspect of the present invention, there is provided an isolated polynucleotide encoding an exemplary enzyme of the present invention (SEQ ID NO:1) comprising the DNA of FIGS. 1a and 1b.

The present invention also relates to polynucleotides which differ from the reference polynucleotide such that the changes are silent changes, for example the changes do not alter the amino acid sequence encoded by the polynucleotide. The present invention also relates to nucleotide changes which result in amino acid substitutions, additions, deletions, fusions and truncations in the enzyme encoded by the reference polynucleotide (SEQ ID NO:1). In a preferred aspect of the invention these enzymes retain about the same biological action as the enzyme encoded by the reference polynucleotide.

The invention also provides isolated nucleic acid molecules that encode the phytase polypeptide described above.

For example, nucleic acids that encode SEQ ID NO:2 are included in the invention. These nucleic acids can contain naturally occurring nucleotide sequences, or sequences that differ from those of the naturally occurring nucleic acids that encode phytases, but encode the same amino acids, due to the degeneracy of the genetic code. The nucleic acids of the invention can contain DNA or RNA nucleotides, or combinations or modifications thereof. Exemplary nucleic acids of the invention are shown in SEQ ID NO:1.

The polynucleotide of the present invention may be in the form of DNA which DNA includes cDNA, genomic DNA, and synthetic DNA. The DNA may be double-stranded or single-stranded, and if single stranded may be the coding strand or non-coding (anti-sense) strand. The coding sequence which encodes the mature enzyme may be identical to the coding sequences shown in FIGS. 1a and 1b and/or that of the deposited clone (SEQ ID NO:1), or may be a different coding sequence which coding sequence, as a result of the redundancy or degeneracy of the genetic code, encodes the same mature enzyme as the DNA of FIGS. 1a and 1b (e.g., SEQ ID NO:1).

The polynucleotide which encodes for the mature enzyme of FIGS. 1a and 1b (e.g., SEQ ID NO:2) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

The present invention further relates to variants of the hereinabove described polynucleotides which encode for fragments, analogs and derivatives of the enzyme having the deduced amino acid sequence of FIGS. 1a and 1b (e.g., SEQ ID NO:2). The variant of the polynucleotide may be a naturally occurring allelic variant of the polynucleotide or a non-naturally occurring variant of the polynucleotide.

Thus, the present invention includes polynucleotides encoding the same mature enzyme as shown in FIGS. 1a and 1b as well as variants of such polynucleotides which variants encode for a fragment, derivative or analog of the enzyme of FIGS. 1a and 1b. Such nucleotide variants include deletion variants, substitution variants and addition or insertion variants.

As hereinabove indicated, the polynucleotide may have a coding sequence which is a naturally occurring allelic variant of the coding sequence shown in FIGS. 1a and 1b. As known in the art, an allelic variant is an alternate form of a polynucleotide sequence which may have a substitution, deletion or addition of one or more nucleotides, which does not substantially alter the function of the encoded enzyme.

Phytase variants, including variant of the phytases of the invention, the phytases described herein, or, any phytase, can be produced by any number of means including methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, GSSM™ and any combination thereof.

In one aspect, a non-stochastic method termed synthetic ligation reassembly (SLR), that is somewhat related to stochastic shuffling, save that the nucleic acid building blocks are not shuffled or concatenated or chimerized randomly, but rather are assembled non-stochastically can be used to create variants.

The SLR method does not depend on the presence of a high level of homology between polynucleotides to be shuffled. The invention can be used to non-stochastically generate libraries (or sets) of progeny molecules comprised of over $10^{100}$ different chimeras. Conceivably, SLR can even be used to generate libraries comprised of over $10^{1000}$ different progeny chimeras.

Thus, in one aspect, the invention provides a non-stochastic method of producing a set of finalized chimeric nucleic acid molecules having an overall assembly order that is chosen by design, which method is comprised of the steps of generating by design a plurality of specific nucleic acid building blocks having serviceable mutually compatible ligatable ends, and assembling these nucleic acid building blocks, such that a designed overall assembly order is achieved.

The mutually compatible ligatable ends of the nucleic acid building blocks to be assembled are considered to be "serviceable" for this type of ordered assembly if they enable the building blocks to be coupled in predetermined orders. Thus, in one aspect, the overall assembly order in which the nucleic acid building blocks can be coupled is specified by the design of the ligatable ends and, if more than one assembly step is to be used, then the overall assembly order in which the nucleic acid building blocks can be coupled is also specified by the sequential order of the assembly step(s). In a one embodiment of the invention, the annealed building pieces are treated with an enzyme, such as a ligase (e.g., T4 DNA ligase) to achieve covalent bonding of the building pieces.

In a another embodiment, the design of nucleic acid building blocks is obtained upon analysis of the sequences of a set of progenitor nucleic acid templates that serve as a basis for producing a progeny set of finalized chimeric nucleic acid molecules. These progenitor nucleic acid templates thus serve as a source of sequence information that aids in the design of the nucleic acid building blocks that are to be mutagenized, i.e. chimerized or shuffled.

In one exemplification, the invention provides for the chimerization of a family of related genes and their encoded family of related products. In a particular exemplification, the encoded products are enzymes. Enzymes and polypeptides of the invention can be mutagenized in accordance with the methods described herein.

Thus according to one aspect of the invention, the sequences of a plurality of progenitor nucleic acid templates are aligned in order to select one or more demarcation points, which demarcation points can be located at an area of homology. The demarcation points can be used to delineate the boundaries of nucleic acid building blocks to be generated. Thus, the demarcation points identified and selected in the progenitor molecules serve as potential chimerization points in the assembly of the progeny molecules.

Typically a serviceable demarcation point is an area of homology (comprised of at least one homologous nucleotide base) shared by at least two progenitor templates, but the demarcation point can be an area of homology that is shared by at least half of the progenitor templates, at least two thirds of the progenitor templates, at least three fourths of the progenitor templates, and can be at almost all of the progenitor templates. A serviceable demarcation point can be an area of homology that is shared by all of the progenitor templates.

In a one embodiment, the ligation reassembly process is performed exhaustively in order to generate an exhaustive library. In other words, all possible ordered combinations of the nucleic acid building blocks are represented in the set of finalized chimeric nucleic acid molecules. At the same time, the assembly order (i.e. the order of assembly of each building block in the 5' to 3 sequence of each finalized chimeric nucleic acid) in each combination is by design (or non-stochastic). Because of the non-stochastic nature of the method, the possibility of unwanted side products is greatly reduced.

In another embodiment, the method provides that, the ligation reassembly process is performed systematically, for example in order to generate a systematically compartmentalized library, with compartments that can be screened systematically, e.g., one by one. In other words the invention provides that, through the selective and judicious use of specific nucleic acid building blocks, coupled with the selective and judicious use of sequentially stepped assembly reactions, an experimental design can be achieved where specific sets of progeny products are made in each of several reaction vessels. This allows a systematic examination and screening procedure to be performed. Thus, it allows a potentially very large number of progeny molecules to be examined systematically in smaller groups.

Because of its ability to perform chimerizations in a manner that is highly flexible yet exhaustive and systematic as well, particularly when there is a low level of homology among the progenitor molecules, the instant invention provides for the generation of a library (or set) comprised of a large number of progeny molecules. Because of the non-stochastic nature of the instant ligation reassembly invention, the progeny molecules generated can comprise a library of finalized chimeric nucleic acid molecules having an overall assembly order that is chosen by design. In a particularly embodiment, such a generated library is comprised of greater than $10^3$ to greater than $10^{1000}$ different progeny molecular species.

In one aspect, a set of finalized chimeric nucleic acid molecules, produced as described is comprised of a polynucleotide encoding a polypeptide. According to one embodiment, this polynucleotide is a gene, which may be a man-made gene. According to another embodiment, this polynucleotide is a gene pathway, which may be a man-made gene pathway. The invention provides that one or more man-made genes generated by the invention may be incorporated into a man-made gene pathway, such as pathway operable in a eukaryotic organism (including a plant).

In another exemplifaction, the synthetic nature of the step in which the building blocks are generated allows the design and introduction of nucleotides (e.g., one or more nucleotides, which may be, for example, codons or introns or regulatory sequences) that can later be optionally removed in an in vitro process (e.g., by mutageneis) or in an in vivo process (e.g., by utilizing the gene splicing ability of a host organism). It is appreciated that in many instances the introduction of these nucleotides may also be desirable for many other reasons in addition to the potential benefit of creating a serviceable demarcation point.

Thus, according to another embodiment, the invention provides that a nucleic acid building block can be used to introduce an intron. Thus, the invention provides that functional introns may be introduced into a man-made gene of the invention. The invention also provides that functional introns may be introduced into a man-made gene pathway of the invention. Accordingly, the invention provides for the generation of a chimeric polynucleotide that is a man-made gene containing one (or more) artificially introduced intron(s).

Accordingly, the invention also provides for the generation of a chimeric polynucleotide that is a man-made gene pathway containing one (or more) artificially introduced intron(s). In one aspect, the artificially introduced intron(s) are functional in one or more host cells for gene splicing much in the way that naturally-occurring introns serve functionally in gene splicing. The invention provides a process of producing man-made intron-containing polynucleotides to be introduced into host organisms for recombination and/or splicing.

A man-made gene produced using the invention can also serve as a substrate for recombination with another nucleic acid. Likewise, a man-made gene pathway produced using the invention can also serve as a substrate for recombination with another nucleic acid. In a preferred instance, the recombination is facilitated by, or occurs at, areas of homology between the man-made intron-containing gene and a nucleic acid with serves as a recombination partner. In a particularly preferred instance, the recombination partner may also be a nucleic acid generated by the invention, including a man-made gene or a man-made gene pathway. Recombination may be facilitated by or may occur at areas of homology that exist at the one (or more) artificially introduced intron(s) in the man-made gene.

The synthetic ligation reassembly method of the invention utilizes a plurality of nucleic acid building blocks, each of which can have two ligatable ends. The two ligatable ends on each nucleic acid building block may be two blunt ends (i.e. each having an overhang of zero nucleotides), or can be one blunt end and one overhang, or, two overhangs.

A serviceable overhang for this purpose may be a 3' overhang or a 5' overhang. Thus, a nucleic acid building block may have a 3' overhang or alternatively a 5' overhang or alternatively two 3' overhangs or alternatively two 5' overhangs. The overall order in which the nucleic acid building blocks are assembled to form a finalized chimeric nucleic acid molecule is determined by purposeful experimental design and is not random.

A nucleic acid building block can be generated by chemical synthesis of two single-stranded nucleic acids (also referred to as single-stranded oligos) and contacting them so as to allow them to anneal to form a double-stranded nucleic acid building block.

A double-stranded nucleic acid building block can be of variable size. The sizes of these building blocks can be small or large. Preferred sizes for building block range from 1 base pair (not including any overhangs) to 100,000 base pairs (not including any overhangs). Other preferred size ranges are also provided, which have lower limits of from 1 bp to 10,000 bp (including every integer value in between), and upper limits of from 2 bp to 100,000 bp (including every integer value in between).

Many methods exist by which a double-stranded nucleic acid building block can be generated that is serviceable for the invention; and these are known in the art and can be readily performed by the skilled artisan.

According to one embodiment, a double-stranded nucleic acid building block is generated by first generating two single stranded nucleic acids and allowing them to anneal to form a double-stranded nucleic acid building block. The two strands of a double-stranded nucleic acid building block may be complementary at every nucleotide apart from any that form an overhang; thus containing no mismatches, apart from any overhang(s). According to another embodiment, the two strands of a double-stranded nucleic acid building block are complementary at fewer than every nucleotide apart from any that form an overhang. Thus, according to this embodiment, a double-stranded nucleic acid building block can be used to introduce codon degeneracy. In one aspect the codon degeneracy is introduced using the site-saturation mutagenesis described herein, using one or more N,N,G/T cassettes or alternatively using one or more N,N,N cassettes.

The in vivo recombination method of the invention can be performed blindly on a pool of unknown hybrids or alleles of a specific polynucleotide or sequence. However, it is not necessary to know the actual DNA or RNA sequence of the specific polynucleotide.

The approach of using recombination within a mixed population of genes can be useful for the generation of any useful proteins, for example, interleukin I, antibodies, tPA and growth hormone. This approach may be used to generate proteins having altered specificity or activity. The approach may also be useful for the generation of hybrid nucleic acid sequences, for example, promoter regions, introns, exons, enhancer sequences, 31 untranslated regions or 51 untranslated regions of genes. Thus this approach may be used to generate genes having increased rates of expression. This approach may also be useful in the study of repetitive DNA sequences. Finally, this approach may be useful to mutate ribozymes or aptamers.

In one aspect variants of the polynucleotides and polypeptides described herein are obtained by the use of repeated cycles of reductive reassortment, recombination and selection which allow for the directed molecular evolution of highly complex linear sequences, such as DNA, RNA or proteins thorough recombination.

In vivo shuffling of molecules is useful in providing variants and can be performed utilizing the natural property of cells to recombine multimers. While recombination in vivo has provided the major natural route to molecular diversity, genetic recombination remains a relatively complex process that involves 1) the recognition of homologies; 2) strand cleavage, strand invasion, and metabolic steps leading to the production of recombinant chiasma; and finally 3) the resolution of chiasma into discrete recombined molecules. The formation of the chiasma requires the recognition of homologous sequences.

In another embodiment, the invention includes a method for producing a hybrid polynucleotide from at least a first polynucleotide and a second polynucleotide. The invention can be used to produce a hybrid polynucleotide by introducing at least a first polynucleotide and a second polynucleotide which share at least one region of partial sequence homology into a suitable host cell. The regions of partial sequence homology promote processes which result in sequence reorganization producing a hybrid polynucleotide. The term "hybrid polynucleotide", as used herein, is any nucleotide sequence which results from the method of the present invention and contains sequence from at least two original polynucleotide sequences. Such hybrid polynucleotides can result from intermolecular recombination events which promote sequence integration between DNA molecules. In addition, such hybrid polynucleotides can result from intramolecular reductive reassortment processes which utilize repeated sequences to alter a nucleotide sequence within a DNA molecule.

The invention provides a means for generating hybrid polynucleotides which may encode biologically active hybrid polypeptides (e.g., a hybrid phytase). In one aspect, the original polynucleotides encode biologically active polypeptides. The method of the invention produces new hybrid polypeptides by utilizing cellular processes which integrate the sequence of the original polynucleotides such that the resulting hybrid polynucleotide encodes a polypeptide demonstrating activities derived from the original biologically active polypeptides. For example, the original polynucleotides may encode a particular enzyme from different microorganisms. An enzyme encoded by a first polynucleotide from one organism or variant may, for example, function effectively under a particular environmental condition, e.g., high salinity. An enzyme encoded by a second polynucleotide from a different organism or variant may function effectively under a different environmental condition, such as extremely high temperatures. A hybrid polynucleotide containing sequences from the first and second original polynucleotides may encode an enzyme which exhibits characteristics of both enzymes encoded by the original polynucleotides. Thus, the enzyme encoded by the hybrid polynucleotide may function effectively under environmental conditions shared by each of the enzymes encoded by the first and second polynucleotides, e.g., high salinity and extreme temperatures.

Enzymes encoded by original polynucleotides include, but are not limited to, phytases. A hybrid polypeptide resulting from the method of the invention may exhibit specialized enzyme activity not displayed in the original enzymes. For example, following recombination and/or reductive reassortment of polynucleotides encoding hydrolase activities, the resulting hybrid polypeptide encoded by a hybrid polynucleotide can be screened for specialized hydrolase activities obtained from each of the original enzymes, i.e., the type of bond on which the hydrolase acts and the temperature at which the hydrolase functions. Thus, for example, the hydrolase may be screened to ascertain those chemical functionalities which distinguish the hybrid hydrolase from the original hydrolyases, such as: (a) amide (peptide bonds), i.e., proteases; (b) ester bonds, i.e., esterases and lipases; (c) acetals, i.e., glycosidases and, for example, the temperature, pH or salt concentration at which the hybrid polypeptide functions.

Sources of the original polynucleotides may be isolated from individual organisms ("isolates"), collections of organisms that have been grown in defined media ("enrichment cultures"), or, uncultivated organisms ("environmental samples"). The use of a culture-independent approach to derive polynucleotides encoding novel bioactivities from environmental samples is most preferable since it allows one to access untapped resources of biodiversity.

"Environmental libraries" are generated from environmental samples and represent the collective genomes of naturally occurring organisms archived in cloning vectors that can be propagated in suitable prokaryotic hosts. Because the cloned DNA is initially extracted directly from environmental samples, the libraries are not limited to the small fraction of prokaryotes that can be grown in pure culture. Additionally, a normalization of the environmental DNA present in these samples could allow more equal representation of the DNA from all of the species present in the original sample. This can dramatically increase the efficiency of finding interesting genes from minor constituents of the sample which may be under-represented by several orders of magnitude compared to the dominant species.

For example, gene libraries generated from one or more uncultivated microorganisms are screened for an activity of interest. Potential pathways encoding bioactive molecules of interest are first captured in prokaryotic cells in the form of gene expression libraries. Polynucleotides encoding activities of interest are isolated from such libraries and introduced into a host cell. The host cell is grown under conditions which promote recombination and/or reductive reassortment creating potentially active biomolecules with novel or enhanced activities.

The microorganisms from which the polynucleotide may be prepared include prokaryotic microorganisms, such as *Xanthobacter*, Eubacteria and Archaebacteria, and lower eukaryotic microorganisms such as fungi, some algae and protozoa. Polynucleotides may be isolated from environmental samples in which case the nucleic acid may be recovered without culturing of an organism or recovered from one or more cultured organisms. In one aspect, such microorganisms may be extremophiles, such as hyperthermophiles, psychrophiles, psychrotrophs, halophiles, barophiles and acidophiles. Polynucleotides encoding enzymes isolated from extremophilic microorganisms are particularly preferred. Such enzymes may function at temperatures above 100° C. in terrestrial hot springs and deep sea thermal vents, at temperatures below 0° C. in arctic waters, in the saturated salt environment of the Dead Sea, at pH values around 0 in coal deposits and geothermal sulfur-rich springs, or at pH values greater than 11 in sewage sludge. For example, several esterases and lipases cloned and expressed from extremophilic organisms show high activity throughout a wide range of temperatures and pHs.

Polynucleotides selected and isolated as hereinabove described are introduced into a suitable host cell. A suitable host cell is any cell which is capable of promoting recombination and/or reductive reassortment. The selected polynucleotides can be already in a vector which includes appropriate control sequences. The host cell can be a higher eukaryotic cell, such as a mammalian cell, or a lower eukaryotic cell, such as a yeast cell, or, the host cell can be a prokaryotic cell, such as a bacterial cell. Introduction of the construct into the host cell can be effected by calcium phosphate transfection, DEAE-Dextran mediated transfection, or electroporation (Davis et al., 1986).

As representative examples of appropriate hosts, there may be mentioned: bacterial cells, such as *Bacillus* (e.g., *Bacillus cereus*), *E. coli, Streptomyces, Salmonella typhimurium*; fungal cells, yeast; insect cells such as *Drosophila* S2 and *Spodoptera* Sf9; animal cells such as CHO, COS or Bowes melanoma; adenoviruses; and plant cells. The selection of an appropriate host is deemed to be within the scope of those skilled in the art from the teachings herein.

With particular references to various mammalian cell culture systems that can be employed to express recombinant protein, examples of mammalian expression systems include the COS-7 lines of monkey kidney fibroblasts, described in "SV40-transformed simian cells support the replication of early SV40 mutants" (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Host cells containing the polynucleotides of interest can be cultured in conventional nutrient media modified as appropriate for activating promoters, selecting transformants or amplifying genes. The culture conditions, such as temperature, pH and the like, are those previously used with the host cell selected for expression, and will be apparent to the ordinarily skilled artisan. The clones which are identified as having the specified enzyme activity may then be sequenced to identify the polynucleotide sequence encoding an enzyme having the enhanced activity.

In another aspect, methods can be used to generate novel polynucleotides encoding biochemical pathways from one or more operons or gene clusters or portions thereof. For example, bacteria and many eukaryotes have a coordinated mechanism for regulating genes whose products are involved in related processes. The genes are clustered, in structures referred to as "gene clusters," on a single chromosome or immediately adjacent to one another and are transcribed together under the control of a single regulatory sequence, including a single promoter which initiates transcription of the entire cluster. Thus, a gene cluster is a group of adjacent genes that are either identical or related, usually as to their function. An example of a biochemical pathway encoded by gene clusters is a polyketide pathway. Polyketides are molecules which are an extremely rich source of bioactivities, including antibiotics (such as tetracyclines and erythromycin), anti-cancer agents (daunomycin), immunosuppressants (FK506 and rapamycin), and veterinary products (monensin). Many polyketides (produced by polyketide synthases) are valuable as therapeutic agents. Polyketide synthases are multifunctional enzymes that catalyze the biosynthesis of an enormous variety of carbon chains differing in length and patterns of functionality and cyclization. Polyketide synthase genes fall into gene clusters and at least one type (designated type I) of polyketide synthases have large size genes and enzymes, complicating genetic manipulation and in vitro studies of these genes/proteins.

Gene cluster DNA can be isolated from different organisms and ligated into vectors, particularly vectors containing expression regulatory sequences which can control and regulate the production of a detectable protein or protein-related array activity from the ligated gene clusters. Use of vectors which have an exceptionally large capacity for exogenous DNA introduction are particularly appropriate for use with such gene clusters and are described by way of example herein to include the f-factor (or fertility factor) of *E. coli*. This f-factor of *E coli* is a plasmid which affects high-frequency transfer of itself during conjugation and is ideal to achieve and stably propagate large DNA fragments, such as gene clusters from mixed microbial samples. Once ligated into an appropriate vector, two or more vectors containing different phytase gene clusters can be introduced into a suitable host cell. Regions of partial sequence homology shared by the gene clusters will promote processes which result in sequence reorganization resulting in a hybrid gene cluster. The novel hybrid gene cluster can then be screened for enhanced activities not found in the original gene clusters.

Therefore, in a one embodiment, the invention relates to a method for producing a biologically active hybrid polypeptide and screening such a polypeptide for enhanced activity by:

1) introducing at least a first polynucleotide in operable linkage and a second polynucleotide in operable linkage, said at least first polynucleotide and second polynucleotide sharing at least one region of partial sequence homology, into a suitable host cell;
2) growing the host cell under conditions which promote sequence reorganization resulting in a hybrid polynucleotide in operable linkage;
3) expressing a hybrid polypeptide encoded by the hybrid polynucleotide;
4) screening the hybrid polypeptide under conditions which promote identification of enhanced biological activity; and
5) isolating the a polynucleotide encoding the hybrid polypeptide.

Methods for screening for various enzyme activities are known to those of skill in the art and are discussed throughout the present specification. Such methods may be employed when isolating the polypeptides and polynucleotides of the invention.

As representative examples of expression vectors which may be used there may be mentioned viral particles, baculovirus, bacteriophage insertion vectors or replacement vectors, phage, plasmids, phagemids, cosmids, fosmids, bacterial artificial chromosomes (BAC), viral DNA (e.g., vaccinia, adenovirus, fowl pox virus, pseudorabies and derivatives of SV40), P1-based artificial chromosomes (PAC), yeast plasmids, yeast artificial chromosomes (YAC), and any other vectors specific for specific hosts of interest (such as *Bacillus, Aspergillus* and yeast). Thus, for example, the DNA may be included in any one of a variety of expression vectors for expressing a polypeptide. Such vectors include chromosomal, nonchromosomal and synthetic DNA sequences. Large numbers of suitable vectors are known to those of skill in the art, and are commercially available. The following vectors are provided by way of example; Bacterial: pQE vectors (Qiagen), pBluescript® plasmids, pNH vectors, (lambda-ZAP® vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia>. However, any other plasmid or other vector may be used so long as they are replicable and viable in the host. Low copy number or high copy number vectors may be employed with the present invention.

An exemplary vector for use in the present invention contains an f-factor origin replication. The f-factor (or fertility factor) in *E. coli* is a plasmid which effects high frequency transfer of itself during conjugation and less frequent transfer of the bacterial chromosome itself. A particularly preferred embodiment is to use cloning vectors, referred to as "fosmids" or bacterial artificial chromosome (BAC) vectors. These are derived from *E. coli* f-factor which is able to stably integrate large segments of genomic DNA. When integrated with DNA from a mixed uncultured environmental sample, this makes it possible to achieve large genomic fragments in the form of a stable "environmental DNA library."

An exemplary vector for use in the present invention is a cosmid vector. Cosmid vectors were originally designed to clone and propagate large segments of genomic DNA. Cloning into cosmid vectors is described in detail in "Molecular Cloning: A laboratory Manual" (Sambrook et al., 1989).

The DNA sequence in the expression vector is operatively linked to an appropriate expression control sequence(s) (promoter) to direct RNA synthesis. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector also contains a ribosome binding site for translation initiation and a transcription terminator. The vector may also include appropriate sequences for amplifying expression. Promoter regions can be selected from any desired gene using CAT (chloranphenicol transferase) vectors or other vectors with selectable markers. In addition, the expression vectors can contain one or more selectable marker genes to provide a phenotypic trait for selection of transformed host cells such as dihydrofolate reductase or neomycin resistance for eukaryotic cell culture, or tetracycline or ampicillin resistance in *E. coli*.

In vivo reassortment is focused on "inter-molecular" processes collectively referred to as "recombination" which in bacteria, is generally viewed as a "RecA-dependent" phenomenon. The invention can rely on recombination processes of a host cell to recombine and re-assort sequences, or the cells' ability to mediate reductive processes to decrease the complexity of quasi-repeated sequences in the cell by deletion. This process of "reductive reassortment" occurs by an "intra-molecular", RecA-independent process.

Therefore, in another aspect of the invention, variant polynucleotides can be generated by the process of reductive reassortment. The method involves the generation of constructs containing consecutive sequences (original encoding sequences), their insertion into an appropriate vector, and their subsequent introduction into an appropriate host cell. The reassortment of the individual molecular identities occurs by combinatorial processes between the consecutive sequences in the construct possessing regions of homology, or between quasi-repeated units. The reassortment process recombines and/or reduces the complexity and extent of the repeated sequences, and results in the production of novel molecular species. Various treatments may be applied to enhance the rate of reassortment. These could include treatment with ultra-violet light, or DNA damaging chemicals, and/or the use of host cell lines displaying enhanced levels of "genetic instability". Thus the reassortment process may involve homologous recombination or the natural property of quasi-repeated sequences to direct their own evolution.

Repeated or "quasi-repeated" sequences play a role in genetic instability. In the present invention, "quasi-repeats" are repeats that are not restricted to their original unit structure. Quasi-repeated units can be presented as an array of sequences in a construct; consecutive units of similar sequences. Once ligated, the junctions between the consecutive sequences become essentially invisible and the quasi-repetitive nature of the resulting construct is now continuous at the molecular level. The deletion process the cell performs to reduce the complexity of the resulting construct operates between the quasi-repeated sequences. The quasi-repeated units provide a practically limitless repertoire of templates upon which slippage events can occur. The constructs containing the quasi-repeats thus effectively provide sufficient molecular elasticity that deletion (and potentially insertion) events can occur virtually anywhere within the quasi-repetitive units.

When the quasi-repeated sequences are all ligated in the same orientation, for instance head to tail or vice versa, the cell cannot distinguish individual units. Consequently, the reductive process can occur throughout the sequences. In contrast, when for example, the units are presented head to head, rather than head to tail, the inversion delineates the endpoints of the adjacent unit so that deletion formation will favor the loss of discrete units. Thus, it is preferable with the present method that the sequences are in the same orientation. Random orientation of quasi-repeated sequences will result in the loss of reassortment efficiency, while consistent orientation of the sequences will offer the highest efficiency. However, while having fewer of the contiguous sequences in the same orientation decreases the efficiency, it may still provide sufficient elasticity for the effective recovery of novel molecules. Constructs can be made with the quasi-repeated sequences in the same orientation to allow higher efficiency.

Sequences can be assembled in a head to tail orientation using any of a variety of methods, including the following:
 a) Primers that include a poly-A head and poly-T tail which when made single-stranded would provide orientation can be utilized. This is accomplished by having the first few bases of the primers made from RNA and hence easily removed RNAseH.
 b) Primers that include unique restriction cleavage sites can be utilized. Multiple sites, a battery of unique sequences, and repeated synthesis and ligation steps would be required.
 c) The inner few bases of the primer could be thiolated and an exonuclease used to produce properly tailed molecules.

The recovery of the re-assorted sequences relies on the identification of cloning vectors with a reduced RI. The re-assorted encoding sequences can then be recovered by amplification. The products are re-cloned and expressed. The recovery of cloning vectors with reduced RI can be effected by:
1) The use of vectors only stably maintained when the construct is reduced in complexity.
2) The physical recovery of shortened vectors by physical procedures. In this case, the cloning vector would be recovered using standard plasmid isolation procedures and size fractionated on either an agarose gel, or column with a low molecular weight cut off utilizing standard procedures.
3) The recovery of vectors containing interrupted genes which can be selected when insert size decreases.
4) The use of direct selection techniques with an expression vector and the appropriate selection.

Encoding sequences (for example, genes) from related organisms may demonstrate a high degree of homology and encode quite diverse protein products. These types of sequences are particularly useful in the present invention as quasi-repeats. However, while the examples illustrated below demonstrate the reassortment of nearly identical original encoding sequences (quasi-repeats), this process is not limited to such nearly identical repeats.

The following example demonstrates a method of the invention. Encoding nucleic acid sequences (quasi-repeats) derived from three (3) unique species are depicted. Each sequence encodes a protein with a distinct set of properties. Each of the sequences differs by a single or a few base pairs at a unique position in the sequence which are designated "A", "B" and "C". The quasi-repeated sequences are separately or collectively amplified and ligated into random assemblies such that all possible permutations and combinations are available in the population of ligated molecules. The number of quasi-repeat units can be controlled by the assembly conditions. The average number of quasi-repeated units in a construct is defined as the repetitive index (RI).

Once formed, the constructs may, or may not be size fractionated on an agarose gel according to published protocols, inserted into a cloning vector, and transfected into an appropriate host cell. The cells are then propagated and "reductive reassortment" is effected. The rate of the reductive reassortment process may be stimulated by the introduction of DNA damage if desired. Whether the reduction in RI is mediated by deletion formation between repeated sequences by an "intra-molecular" mechanism, or mediated by recombination-like events through "inter-molecular" mechanisms is immaterial. The end result is a reassortment of the molecules into all possible combinations.

Optionally, the method comprises the additional step of screening the library members of the shuffled pool to identify individual shuffled library members having the ability to bind or otherwise interact, or catalyze a particular reaction (e.g., such as catalyzing the hydrolysis of a haloalkane).

The polypeptides that are identified from such libraries can be used for therapeutic, diagnostic, research and related purposes (e.g., catalysts, solutes for increasing osmolarity of an aqueous solution, and the like), and/or can be subjected to one or more additional cycles of shuffling and/or selection.

In another aspect, prior to or during recombination or reassortment, polynucleotides of the invention or polynucleotides generated by the method described herein can be subjected to agents or processes which promote the introduction of mutations into the original polynucleotides. The introduction of such mutations would increase the diversity of resulting hybrid polynucleotides and polypeptides encoded therefrom. The agents or processes which promote mutagenesis can include, but are not limited to: (+)-CC-1065, or a synthetic analog such as (+)-CC-1065-(N-3-Adenine, see Sun and Hurley, 1992); an N-acelylated or deacetylated 4'-fluro-4-aminobiphenyl adduct capable of inhibiting DNA synthesis (see, for example, van de Poll et al., 1992); or a N-acetylated or deacetylated 4-aminobiphenyl adduct capable of inhibiting DNA synthesis (see also, van de Poll et al., 1992, pp. 751-758); trivalent chromium, a trivalent chromium salt, a polycyclic aromatic hydrocarbon ("PAH") DNA adduct capable of inhibiting DNA replication, such as 7-bromomethyl-benz[α]anthracene ("BMA"), tris(2,3-dibromopropyl)phosphate ("Tris-BP"), 1,2-dibromo-3-chloropropane ("DBCP"), 2-bromoacrolein (2BA), benzo[α]pyrene-7,8-dihydrodiol-9-10-epoxide ("BPDE"), a platinum(II) halogen salt, N-hydroxy-2-amino-3-methylimidazo[4,5-f]-quinoline ("N-hydroxy-IQ"), and N-hydroxy-2-amino-1-methyl-6-phenylimidazo[4,5-f]-pyridine ("N-hydroxy-PhIP"). Especially preferred means for slowing or halting PCR amplification consist of UV light (+)-CC-1065 and (+)-CC-1065-(N-3-Adenine). Particularly encompassed means are DNA adducts or polynucleotides comprising the DNA adducts from the polynucleotides or polynucleotides pool, which can be released or removed by a process including heating the solution comprising the polynucleotides prior to further processing.

In another aspect the invention is directed to a method of producing recombinant proteins having biological activity by treating a sample comprising double-stranded template polynucleotides encoding a wild-type protein under conditions according to the invention which provide for the production of hybrid or re-assorted polynucleotides.

The invention also provides for the use of codon primers (containing a degenerate N,N,N sequence) to introduce point mutations into a polynucleotide (e.g., a nucleic acid encoding a phytase of the invention, or, any phytase), so as to generate a set of progeny polypeptides in which a full range of single amino acid substitutions is represented at each amino acid position (Gene Site Saturation Mutagenesis™ (GSSM™)). The oligos used are comprised contiguously of a first homologous sequence, a degenerate N,N,N sequence, and can but not necessarily a second homologous sequence. The downstream progeny translational products from the use of such oligos include all possible amino acid changes at each amino acid site along the polypeptide, because the degeneracy of the N,N,N sequence includes codons for all 20 amino acids.

In one aspect, one such degenerate oligo (comprised of one degenerate N,N,G/T cassette) is used for subjecting each original codon in a parental polynucleotide template to a full range of codon substitutions. In another aspect, at least two degenerate N,N,G/T cassettes are used—either in the same oligo or not, for subjecting at least two original codons in a parental polynucleotide template to a full range of codon substitutions. Thus, more than one N,N,G/T sequence can be contained in one oligo to introduce amino acid mutations at more than one site. This plurality of N,N,G/T sequences can be directly contiguous, or separated by one or more additional nucleotide sequence(s). In another aspect, oligos serviceable for introducing additions and deletions can be used either alone or in combination with the codons containing an N,N, G/T sequence, to introduce any combination or permutation of amino acid additions, deletions, and/or substitutions.

In a particular exemplification, it is possible to simultaneously mutagenize two or more contiguous amino acid positions using an oligo that contains contiguous N,N,G/T triplets, i.e. a degenerate (N,N,G/T), sequence.

In another aspect, the present invention provides for the use of degenerate cassettes having less degeneracy than the N,N, G/T sequence. For example, it may be desirable in some instances to use (e.g. in an oligo) a degenerate triplet sequence comprised of only one N, where said N can be in the first second or third position of the triplet. Any other bases including any combinations and permutations thereof can be used in the remaining two positions of the triplet. Alternatively, it may be desirable in some instances to use (e.g., in an oligo) a degenerate N,N,N triplet sequence, or an N,N, G/C triplet sequence.

It is appreciated, however, that the use of a degenerate triplet (such as N,N,G/T or an N,N, G/C triplet sequence) as disclosed in the instant invention is advantageous for several reasons. In one aspect, this invention provides a means to systematically and fairly easily generate the substitution of the full range of possible amino acids (for a total of 20 amino acids) into each and every amino acid position in a polypeptide. Thus, for a 100 amino acid polypeptide, the invention provides a way to systematically and fairly easily generate 2000 distinct species (i.e., 20 possible amino acids per position times 100 amino acid positions). It is appreciated that there is provided, through the use of an oligo containing a degenerate N,N,G/T or an N,N, G/C triplet sequence, 32 individual sequences that code for 20 possible amino acids. Thus, in a reaction vessel in which a parental polynucleotide sequence is subjected to saturation mutagenesis using one such oligo, there are generated 32 distinct progeny polynucleotides encoding 20 distinct polypeptides. In contrast, the use of a non-degenerate oligo in site-directed mutagenesis leads to only one progeny polypeptide product per reaction vessel.

This invention also provides for the use of nondegenerate oligos, which can optionally be used in combination with degenerate primers disclosed. It is appreciated that in some situations, it is advantageous to use nondegenerate oligos to generate specific point mutations in a working polynucleotide. This provides a means to generate specific silent point mutations, point mutations leading to corresponding amino acid changes, and point mutations that cause the generation of stop codons and the corresponding expression of polypeptide fragments.

Thus, in one embodiment, each saturation mutagenesis reaction vessel contains polynucleotides encoding at least 20 progeny polypeptide molecules such that all 20 amino acids are represented at the one specific amino acid position corresponding to the codon position mutagenized in the parental polynucleotide. The 32-fold degenerate progeny polypeptides generated from each saturation mutagenesis reaction vessel can be subjected to clonal amplification (e.g., cloned into a suitable *E. coli* host using an expression vector) and subjected to expression screening. When an individual progeny polypeptide is identified by screening to display a favorable change in property (when compared to the parental polypeptide), it can be sequenced to identify the correspondingly favorable amino acid substitution contained therein.

It is appreciated that upon mutagenizing each and every amino acid position in a parental polypeptide using saturation mutagenesis as disclosed herein, favorable amino acid changes may be identified at more than one amino acid position. One or more new progeny molecules can be generated that contain a combination of all or part of these favorable amino acid substitutions. For example, if 2 specific favorable amino acid changes are identified in each of 3 amino acid positions in a polypeptide, the permutations include 3 possibilities at each position (no change from the original amino acid, and each of two favorable changes) and 3 positions. Thus, there are 3×3×3 or 27 total possibilities, including 7 that were previously examined——6 single point mutations (i.e., 2 at each of three positions) and no change at any position.

In yet another aspect, site-saturation mutagenesis can be used together with shuffling, chimerization, recombination and other mutagenizing processes, along with screening. This invention provides for the use of any mutagenizing process(es), including saturation mutagenesis, in an iterative manner. In one exemplification, the iterative use of any mutagenizing process(es) is used in combination with screening.

Thus, in a non-limiting exemplification, polynucleotides and polypeptides of the invention can be derived by saturation mutagenesis in combination with additional mutagenization processes, such as process where two or more related polynucleotides are introduced into a suitable host cell such that a hybrid polynucleotide is generated by recombination and reductive reassortment.

In addition to performing mutagenesis along the entire sequence of a gene, mutagenesis can be used to replace each of any number of bases in a polynucleotide sequence, wherein the number of bases to be mutagenized can be every integer from 15 to 100,000. Thus, instead of mutagenizing every position along a molecule, one can subject every or a discrete number of bases (can be a subset totaling from 15 to 100,000) to mutagenesis. In one aspect, a separate nucleotide is used for mutagenizing each position or group of positions along a polynucleotide sequence. A group of 3 positions to be mutagenized may be a codon. The mutations can be introduced using a mutagenic primer, containing a heterologous cassette, also referred to as a mutagenic cassette. Preferred cassettes can have from 1 to 500 bases. Each nucleotide position in such heterologous cassettes be N, A, C, G, T, A/C, A/G, A/T, C/G, C/T, G/T, C/G/T, A/G/T, A/C/T, A/C/G, or E, where E is any base that is not A, C, G, or T (E can be referred to as a designer oligo).

In a general sense, saturation mutagenesis is comprised of mutagenizing a complete set of mutagenic cassettes (wherein each cassette can be about 1-500 bases in length) in defined polynucleotide sequence to be mutagenized (wherein the sequence to be mutagenized can be from about 15 to 100,000 bases in length). Thus, a group of mutations (ranging from 1 to 100 mutations) is introduced into each cassette to be mutagenized. A grouping of mutations to be introduced into one cassette can be different or the same from a second grouping of mutations to be introduced into a second cassette during the application of one round of saturation mutagenesis. Such groupings are exemplified by deletions, additions, groupings of particular codons, and groupings of particular nucleotide cassettes.

Defined sequences to be mutagenized include a whole gene, pathway, cDNA, an entire open reading frame (ORF), and entire promoter, enhancer, repressor/transactivator, origin of replication, intron, operator, or any polynucleotide functional group. Generally, a "defined sequences" for this purpose may be any polynucleotide that a 15 base-polynucleotide sequence, and polynucleotide sequences of lengths between 15 bases and 15,000 bases (this invention specifically names every integer in between). Considerations in choosing groupings of codons include types of amino acids encoded by a degenerate mutagenic cassette.

In one aspect a grouping of mutations can be introduced into a mutagenic cassette, this invention specifically provides for degenerate codon substitutions (using degenerate oligos) that code for 2, 3, 4, 5, 6, 7, 8, 9, 10, 11, 12, 13, 14, 15, 16, 17, 18, 19, and 20 amino acids at each position, and a library of polypeptides encoded thereby.

The present invention also includes polynucleotides, wherein the coding sequence for the mature enzyme may be fused in the same reading frame to a polynucleotide sequence which aids in expression and secretion of an enzyme from a host cell, for example, a leader sequence which functions to control transport of an enzyme from the cell. An enzyme having a leader sequence is an example of a preprotein and may have the leader sequence cleaved by the host cell to form the mature form of the enzyme. The polynucleotides may also encode for a proprotein which is exemplified by a mature protein plus additional 5' amino acid residues. An otherwise mature protein having a prosequence is exemplified by a proprotein that is an inactive form of the protein. Once the prosequence is cleaved an active mature protein remains.

Thus, for example, the polynucleotide of the present invention may encode for a mature enzyme, or for an enzyme having a prosequence or for an enzyme having both a prosequence and a presequence (e.g. leader sequence).

The coding sequences for the phytase enzymes of the present invention were identified by preparing $E.\ coli$ B genomic DNA, for example, and recovering (via, for example, PCR amplification) from the genomic DNA, DNA encoding phytase activity. Such methods for recovery are well-known in the art. One means, for example, comprises designing amplification primers to recover the coding sequence, amplifying the gene from the genomic DNA, subcloning the DNA into a vector, transforming the resulting construct into a host strain, and expressing the phytase enzyme for evaluation. Such procedures are well known in the art and methods are provided, for example, in Sambrook et al., 1989, which is hereby incorporated by reference in its entirety.

An exemplary enzyme of the present invention was isolated from an $E.\ coli$ B genomic DNA by the following technique:

$E.\ coli$ B genomic DNA was obtained comercially (Sigma: Catalog # D-2001, St. Louis, N.J.). The following primers were used to amplify the gene directly from the genomic DNA:

5' primer gtttctgaattcaaggaggaatttaaAT-GAAAGCGATCTTAATCCCATT (SEQ ID NO:3); and

3' primer gtttctggatccTTACAAACTGCACGCCGGTAT (SEQ ID NO:4)

Pfu polymerase was used according to manufacturers protocol (Stratagene Cloning Systems, Inc., La Jolla, Calif.).

PCR product and pQE60 vector (Qiagen) were both digested with EcoRI and BglII restriction endonucleases (New England Biolabs) according to manufacturers protocols. Ligation and transformation into, and expression in M15 pREP4 host cells (Qiagen) yields c-term 6×-His tagged protein.

The isolated nucleic acid sequences and other enzymes may then be measured for retention of biological activity characteristic to the enzyme of the present invention, for example, in an assay for detecting enzymatic phytase activity (Food Chemicals Codex, $4^{th}$ Ed.). Such enzymes include truncated forms of phytase, and variants such as deletion and insertion variants.

An in vitro example of such an assay is the following assay for the detection of phytase activity: Phytase activity can be measured by incubating 150 μl of the enzyme preparation with 600 μl of 2 mM sodium phytate in 100 mM Tris HCl buffer pH 7.5, supplemented with 1 mM $CaCl_2$ for 30 minutes at 37° C. After incubation the reaction is stopped by adding 750 μl of 5% trichloroacetic acid. Phosphate released was measured against phosphate standard spectrophotometrically at 700 nm after adding 1500 μl of the color reagent (4 volumes of 1.5% ammonium molybdate in 5.5% sulfuric acid and 1 volume of 2.7% ferrous sulfate; Shimizu, 1992). One unit of enzyme activity is defined as the amount of enzyme required to liberate one μmol Pi per min under assay conditions. Specific activity can be expressed in units of enzyme activity per mg of protein.

The enzyme of the present invention has enzymatic activity with respect to the hydrolysis of phytate to inositol and free phosphate.

The enzymes and polynucleotides of the present invention can be provided in an isolated form, and can be purified to homogeneity. The phytase polypeptide of the invention can be obtained using any of several standard methods. For example, phytase polypeptides can be produced in a standard recombinant expression system (see below), chemically synthesized (this approach may be limited to small phytase peptide fragments), or purified from organisms in which they are naturally expressed. Serviceable recombinant expression methods include the use of mammalian hosts, microbial hosts, and plant hosts.

The recombinant expression of the instant phytase molecules may be achieved in combination with one or more additional molecules such as, for example, other enzymes. This approach is serviceable for producing combination products, such as a plant or plant part that contains the instant phytase molecules as well as one or more additional molecules—preferably said phytase molecules and said additional molecules are serviceable in a combination treatment. The resulting recombinantly expresssed molecules may be used in homogenized and/or purified form or alternatively in relatively unpurified form (e.g. as consumable plant parts that are serviceable when admixed with other foodstuffs for catalyzing the degradation of phytate).

In sum, in a non-limiting embodiment, the present invention provides a recombinant enzyme expressed in a host. In another non-limiting embodiment, the present invention provides a substantially pure phytase enzyme. Thus, an enzyme of the present invention may be a recombinant enzyme, a natural enzyme, or a synthetic enzyme, preferably a recombinant enzyme.

The present invention also relates to vectors which include polynucleotides of the present invention, host cells which are genetically engineered with vectors of the invention, and the production of enzymes of the invention by recombinant techniques.

Host cells are genetically engineered (e.g. transduced or transformed or transfected) with the vectors containing the polynucleotides of this invention. Such vectors may be, for example, a cloning vector or an expression vector. The vector may be, for example, in the form of a plasmid, a viral particle, a phage, a prion, etc. The engineered host cells can be cultured in conventional nutrient media modified as appropriate for activating promoters, &/or selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Inclusive in this meaning is the use of blunt-ended molecules which could be generated by the use of restriction digestion as well as restriction digestion-independent means. Alternatively, the insert may be incorporated into a vector by so called "ligase-independent" means. In a particular aspect, a "ligase-independent" means is exemplified by the use of topoisomerase-mediated ligation at room temperature, for example according to the commercially available kit termed TOPO-TA Cloning® (Invitrogen Corporation, Carlsbad, Calif.). Alteranative enzymes, including isomers of topoisomerase as well as more distantly related recombination enzymes (e.g. recombinases), may also be serviceable for mediating this type of "ligase-independent" incorporation. In another particular aspect, a "ligase-independent" means is exemplified by the use host repair mechanisms. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: an LTR or SV40 promoter, an *E. coli*. lac or trp, a phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli.*

The vector containing the appropriate DNA sequence as hereinabove described, as well as an appropriate promoter or control sequence, may be employed to transform an appropriate host to permit the host to express the protein.

Exemplary organisms for expressing polypeptides of the invention can be *S. pombe, S. cerevisiae, Pichia* sp., e.g., *P. pastoris, E. coli, Streptomyces* sp., *Bacillus* sp. and *Lactobacillus* sp. Exemplary hosts for expressing polypeptides and nucleic acids of the invention, and to practice the methods of the invention, include bacterial cells, such as *E. coli, Streptomyces, Bacillus ceres, Bacillus subtilis*; fungal cells, such as yeast; insect cells such as *Drosophila* S2 and *Spodoptera* Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. One or more additional inserts may also be incorporated that lead to expression of one or more aditional molecules, such as another phytase or a protease enzyme, preferably said one or more additional molecules are serviceable in combination with the instant phytase in a combination treatment.

Large numbers of suitable vectors and promoters are known to those of skill in the art, and are commercially available. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described here are known in the art and will be apparent to the ordinarily skilled artisan.

The following vectors are provided by way of example; Bacterial: pQE70, pQE60, pQE-9 (Qiagen), pBluescript II® (Stratagene); pTRC99a, pKK223-3, pDR540, pRIT2T (Pharmacia); Eukaryotic: pXT1, pSG5 (Stratagene) pSVK3, pBPV, pMSG, pSVLSV40 (Pharmacia). However, any other plasmids or other vectors may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, 1986).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described (e.g. Sambrook et al., 1989, the disclosure of which is hereby incorporated by reference).

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP 1 gene, and a promoter derived from a highly-expressed gene to direct transcription of a downstream structural sequence. Such promoters can be derived from operons encoding glycolytic enzymes such as 3-phosphoglycerate kinase (PGK), Å-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Bacillus cereus, Salmonella typhimurium and various species within the genera Streptomyces, Bacillus and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, as described (Gluzman, 1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture).

Depending upon the host employed in a recombinant production procedure, the enzymes of the present invention may be glycosylated or may be non-glycosylated. Enzymes of the invention may or may not also include an initial methionine amino acid residue.

In a preferred embodiment, the enzyme of the present invention is a phytase enzyme which is stable to heat and is heat resistant and catalyzes the enzymatic hydrolysis of phytate, i.e., the enzyme is able to renature and regain activity after a brief (i.e., 5 to 30 seconds), or longer period, for example, minutes or hours, exposure to temperatures of up to about 50° C. or slightly above 50° C.

The present invention is further described with reference to the examples contained herein; however, it is to be understood that the present invention is not limited to such examples. All parts or amounts, unless otherwise specified, are by weight.

The present invention also provides an isolated variant phytase polynucleotide, or an oligonucleotide portion thereof comprising a mutation as disclosed herein. As used herein, the term "isolated" or "purified," when used in reference to a polynucleotide, oligonucleotide, or polypeptide, means that the material is in a form other than that in which it normally is found in nature. Thus, where a polynucleotide or polypeptide occurs in a cell in nature, an isolated polynucleotide or purified polypeptide can be one that separated, at least in part, from the materials with which it is normally associated with. In general, an isolated polynucleotide or a purified polypeptide is present in a form in which it constitutes at least about 5 to 10% of a composition, usually 20% to 50% of a composition, particularly about 50% to 75% of a composition, and preferably about 90% to 95% or more of a composition. Methods for isolating a polynucleotide or polypeptide are well known and routine in the art.

As part of or following isolation, a polynucleotide can be joined to other polynucleotides, such as DNA molecules, for example, for mutagenesis studies, to form fusion proteins, or for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, nevertheless are considered "isolated" because they are not in a form in which they exist in nature. Similarly, the polynucleotides, oligonucleotides, and polypeptides can be present in a composition such as media formulation (solutions for introduction of polynucleotides, oligonucleotides, or polypeptides, for example, into cells or compositions or solutions for chemical or enzymatic reactions which are not naturally occurring compositions) and, therein remain isolated polynucleotides, oligonucleotides, or polypeptides within the meaning of that term as it is employed herein. An isolated polynucleotide can be a polynucleotide that is not immediately contiguous with nucleotide sequences with which it is immediately contiguous in a genome or other naturally occurring cellular DNA molecule in nature. Thus, a recombinant polynucleotide, which can comprise a polynucleotide incorporated into a vector, an autonomously replicating plasmid, or a virus; or into the genomic DNA of a prokaryote or eukaryote, which does not normally express a particular polypeptide.

As used herein, the term "polynucleotide" or "oligonucleotide" or "nucleotide sequence" or the like refers to a polymer of two or more nucleotides or nucleotide analogs. The polynucleotide can be a ribonucleic acid (RNA) or deoxyribonucleic acid (DNA) molecule, and can be single stranded or double stranded DNA or RNA, or a double stranded DNA: RNA hybrid. A polynucleotide or oligonucleotide can contain one or more modified bases, for example, inosine or a tritylated base. The bonds linking the nucleotides in a polymer generally are phosphodiester bonds, but can be other bonds routinely used to link nucleotides including, for example, phosphorothioate bonds, thioester bonds, and the like. A polynucleotide also can be a chemically, enzymatically or metabolically modified form.

As used herein, the term "mutant or variant polynucleotide" means a nucleotide sequence that has one or a few nucleotide changes as compared to the nucleotide sequence set forth as SEQ ID NO:1, 7 or 9, for example. The nucleotide change can be a deletion, insertion or substitution, and can be silent such that there is no change in the reading frame of a polypeptide encoded by the wild-type polynucleotide, or can be a change that results in an amino acid change or in the introduction of a STOP codon into the polynucleotide, or a change in a nucleotide sequence involved in transcription or translation of the polynucleotide, for example, a change that results in altered splicing of a gene transcript into an mRNA.

For convenience of discussion and for use as a frame of reference, the phytase nucleotide sequence set forth in SEQ ID NO:1 or SEQ ID NO:7 is referred to as a "wild type" polynucleotide or "wild type" gene sequence, and, similarly, the polypeptide set forth as SEQ ID NO:2 or SEQ ID NO:8 (*E. coli* appA wild type phytase) is referred to as a wild type phytase polypeptide.

Examples of a variant phytase polynucleotide sequence include sequences substantially as set forth in SEQ ID NO:7, wherein the polynucleotide has a nucleotide sequence as set forth in a) SEQ ID NO:9; b) SEQ ID NO:9 wherein all Ts are Us (RNA); wherein the expression of the phytase-encoding nucleic acid leads to the production of said substantially pure phytase enzyme; and c) SEQ ID NO:7, wherein 389 is G; 390 is A; nucleotide 437 is T; 438 is G; 439 is G; 470 is C; 72 is T; 476 is T; 477 is G; 478 is T; 689 is G; 690 is A; 691 is G; 728 is T; 729 is A; 730 is T; 863 is T; 864 is G; 1016 is G, or any combination thereof. More specifically, with respect to part c), the invention provides a nucleotide sequence substantially identical to SEQ ID NO:7, and having a modified nucleotide sequence selected from nucleotide 389 is G and 390 is A; nucleotide 437 is T, 438 is G and 439 is G; 470 is C and 472 is T; 476 is T, 477 is G, and 478 is T; 689 is G, 690 is A and 691 is G; 728 is T, 729 is A, and 730 is T; 863 is T and 864 is G; 1016 is G, or any combination thereof.

Examples of a variant phytase polynucleotide of the invention also include a polynucleotide that encodes a polypeptide having substantially as set forth in SEQ ID NO:8, but having an W68E, Q84W, A95P, K97C, S168E, R181Y, N226C, Y277D or any combination thereof and retain phytase activity.

Additional examples of mutant polynucleotides of the invention include polynucleotide sequences that selectively hybridize to the complements of the polynucleotide sequences, or oligonucleotide portions thereof, as disclosed herein, under highly stringent hybridization conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel et al., Current Protocols in Molecular Biology, (Green Publishing Associates, Inc., and John Wiley & Sons, Inc., New York 1989), and supplements; see p. 2.10.3; Sambrook et al., Molecular Cloning: A laboratory manual (Cold Spring Harbor Laboratory Press, 1989), which are incorporated herein by reference), as well as polynucleotides that encode a phytase polypeptide substantially as set forth in SEQ ID NO:8, but having one or more mutations; or an RNA corresponding to such a polynucleotide (e.g., SEQ ID NO:9).

In alternative aspects, the invention provides polynucleotide or polypeptide sequences having 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 97.5%, 98%, 98.5%, 99%, 99.5%, or more, or complete (100%) sequence identity (i.e., homology) (this encompassing the term "substantially identical") to a phytase-encoding polynucleotide or phytase polypeptide of the invention, including: SEQ ID NO:1 (a phytase-encoding polynucleotide); SEQ ID NO:2 (a phytase polypeptide); SEQ ID NO:9 (a phytase-encoding polynucleotide); SEQ ID NO:10 (a phytase polypeptide); a nucleic acid having sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; or, 1016 is G, or, any combination thereof, wherein the polynucleotide encodes a phytase; a nucleic acid having sequence as set forth in SEQ ID NO:7 and wherein nucleotide 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; and 1016 is G; a nucleic acid encoding a polypeptide having sequence as set forth in SEQ ID NO:8 and having one or more amino acid modifications selected from W68E, Q84W, A95P, K97C, S168E, R181 Y, N226C, Y277D, or any combination thereof, wherein the polypeptide has phytase activity; a nucleic acid encoding a polypeptide having sequence as set forth in SEQ ID NO:8 and having the amino acid modifications W68E, Q84W, A95P, K97C, S168E, R181Y, N226C, Y277D, wherein the polypeptide has phytase activity; or other phytases, for example, the E. coli appA "wild type" phytase-encoding SEQ ID NO:7, or, a polypeptide sequence of SEQ ID NO:2 or the E. coli appA "wild type" phytase SEQ ID NO:8.

Sequence identity can be measured using sequence analysis software (e.g., Sequence Analysis Software Package of the Genetics Computer Group, University of Wisconsin Biotechnology Center, 1710 University Avenue, Madison Wis. 53705).

A polynucleotide or oligonucleotide portion thereof of the invention can be useful, for example, as a probe or as a primer for an amplification reaction. Reference to an "oligonucleotide portion" of a polynucleotide means a nucleotide sequence of the variant or mutant polynucleotide that is less than the full length polynucleotide. Generally, an oligonucleotide useful as a probe or a primer contains at least about 10 nucleotides, and usually contains about 15 to 30 nucleotides or more (see, for example, Tables 1 and 2). Polynucleotides and oligonucleotides can be prepared by any suitable method, including, for example, by restriction enzyme digestion of an appropriate polynucleotide, by direct chemical synthesis using a method such as the phosphotriester method (Narang et al., 1979, Meth. Enzymol., 68:90-99); the phosphodiester method (Brown et al., 1979, Meth. Enzymol., 68:109-151); the diethylphosphoramidite method (Beaucage et al., 1981, Tetrahedron Lett., 22:1859-1862); the triester method (Matteucci et al., 1981, J. Am. Chem. Soc., 103:3185-3191), including by automated synthesis methods; or by a solid support method (see, for example, U.S. Pat. No. 4,458,066). In addition, a polynucleotide or oligonucleotide can be prepared using recombinant DNA methods as disclosed herein or otherwise known in the art.

An oligonucleotide of the invention can include a portion of a phytase polynucleotide, including, for example, a sequence substantially identical to that of SEQ ID NO:7, except wherein nucleotide wherein 389 is G; 390 is A; 437 is T; 438 is G; 439 is G; 470 is C; 472 is T; 476 is T; 477 is G; 478 is T; 689 is G; 690 is A; 691 is G; 728 is T; 729 is A; 730 is T; 863 is T; 864 is G; or, 1016 is G, or wherein the oligonucleotide contains a combination of such substitutions with respect to SEQ ID NO:7. Thus, as disclosed herein, the oligonucleotide can be any length and can encompass one or more of the above mutations.

An oligonucleotide of the invention can selectively hybridize to a mutant phytase polynucleotide sequence as disclosed herein. As used herein, "selectively hybridize" refers to the ability of an oligonucleotide (or polynucleotide) probe to hybridize to a mutant polynucleotide, but not substantially to a wild-type sequence. Hybridization conditions that allow for selective hybridization can be obtained by varying the stringency of the hybridization conditions, as described above, and will depend, in part, on the length of the probe, the relative G:C content, the salt concentration, and the like (see Sambrook et al., supra, 1989). Hybridization conditions that are highly stringent conditions include, for example, washing in 6×SSC/0.05% sodium pyrophosphate at about 37° C. (for 14 nucleotide DNA probe), about 48° C. (for 17 nucleotide probe), about 55° C. (for a 20 nucleotide probe), and about 60° C. (for a 23 nucleotide probe).

An oligonucleotide of the invention can be used as a probe to screen for a particular variant or mutant of interest. In addition, the oligonucleotides of the invention include an antisense molecule, which can be useful, for example, in polynucleotide regulation and amplification reactions of polynucleotide sequences, including mutant phytase polynucleotide sequences. Further, such oligonucleotides can be used as part of ribozyme or triple helix sequence for phytase gene regulation. Still further, such oligonucleotides can be used as a component of diagnostic method, whereby the level of phytase transcript can be determined. Further, such oligonucleotides can be used, for example, to screen for and identify phytase homologs from other species.

The term "primer" or "PCR primer" refers to an isolated natural or synthetic oligonucleotide that can act as a point of initiation of DNA synthesis when placed under conditions suitable for primer extension. Synthesis of a primer extension product is initiated in the presence of nucleoside triphosphates and a polymerase in an appropriate buffer at a suitable temperature. A primer can comprise a plurality of primers, for example, where there is some ambiguity in the information regarding one or both ends of the target region to be synthesized. For instance, if a nucleic acid sequence is determined from a protein sequence, a primer generated to synthesize nucleic acid sequence encoding the protein sequence can comprise a collection of primers that contains sequences representing all possible codon variations based on the degeneracy of the genetic code. One or more of the primers in this collection will be homologous with the end of the target sequence or a sequence flanking a target sequence. Likewise, if a conserved region shows significant levels of polymorphism in a population, mixtures of primers can be prepared that will amplify adjacent sequences.

During PCR amplification, primer pairs flanking a target sequence of interest are used to amplify the target sequence. A primer pair typically comprises a forward primer, which hybridizes to the 5' end of the target sequence, and a reverse primer, which hybridizes to the 3' end of the target sequence. A primer pair of the invention includes at least one forward primer and at least one reverse primer that allows for generation of an amplification product, which can be a long range phytase-specific amplification product or a nested amplification product of such an amplification product, including a forward and reverse primer provided that the forward primer is 5' (or upstream) of the reverse primer with reference to a target polynucleotide sequence, and that the primers are in sufficient proximity such that an amplification product can be generated.

Nucleic acid sequences that encode a fusion protein can be produced and can be operatively linked to expression control sequences. Such fusion proteins and compositions are useful in the development of antibodies or to generate and purify peptides and polypeptides of interest. As used herein, the term "operatively linked" refers to a juxtaposition, wherein the components so described are in a relationship permitting them to function in their intended manner. For example, an expression control sequence operatively linked to a coding sequence is ligated such that expression of the coding sequence is achieved under conditions compatible with the expression control sequences, whereas two operatively linked coding sequences can be ligated such that they are in the same reading frame and, therefore, encode a fusion protein.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and STOP codons. Control sequences include, at a minimum, components whose presence can influence expression, and can also include additional components whose presence is advantageous, for example, leader sequences and fusion partner sequences. Expression control sequences can include a promoter.

A polynucleotide of the invention can comprise a portion of a recombinant nucleic acid molecule, which, for example, can encode a fusion protein. The polynucleotide, or recombinant nucleic acid molecule, can be inserted into a vector, which can be an expression vector, and can be derived from a plasmid, a virus or the like. The expression vector generally contains an origin of replication, a promoter, and one or more genes that allow phenotypic selection of transformed cells containing the vector. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988); baculovirus-derived vectors for expression in insect cells; and the like.

The choice of a vector will also depend on the size of the polynucleotide sequence and the host cell to be employed in the methods of the invention. Thus, the vector used in the invention can be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequences to be analyzed or modified is large because these vectors are able to stably propagate large polynucleotides. Cosmids and phagemids are particularly suited for the expression or manipulation of the phytase polynucleotide of SEQ ID NO:1 or 7 or a mutant phytase polynucleotide as in SEQ ID NO:9.

In yeast, a number of vectors containing constitutive or inducible promoters can be used (see Ausubel et al., supra, 1989; Grant et al., Meth. Enzymol. 153:516-544, 1987; Glover, DNA Cloning, Vol. II, IRL Press, Washington D.C., Ch. 3, 1986; and Bitter, Meth. Enzymol. 152:673-684, 1987; and The Molecular Biology of the Yeast *Saccharomyces*, Eds. Strathern et al., Cold Spring Harbor Press, Vols. I and II, 1982). A constitutive yeast promoter such as ADH or LEU2 or an inducible promoter such as GAL can be used ("Cloning in Yeast," Ch. 3, Rothstein, In "DNA Cloning" Vol. 11, A Practical Approach, ed. Glover, IRL Press, 1986). Alternatively, vectors can be used which promote integration of foreign DNA sequences into the yeast chromosome. The construction of expression vectors and the expression of genes in transfected cells involves the use of molecular cloning techniques also well known in the art (see Sambrook et al., supra, 1989; Ausubel et al., supra, 1989). These methods include in vitro recombinant DNA techniques, synthetic techniques and in vivo recombination/genetic recombination.

A polynucleotide or oligonucleotide can be contained in a vector and can be introduced into a cell by transformation or transfection of the cell. By "transformation" or "transfection" is meant a permanent (stable) or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell can be any prokaryotic or eukaryotic cell into which (or into an ancestor of which) has been introduced, by means of recombinant DNA techniques, a polynucleotide sequence of the invention or fragment thereof. Transformation of a host cell can be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art, or using $MgCl_2$ or RbCl. Transformation can also be performed after forming a protoplast of the host cell or by electroporation.

When the host is a eukaryote, such methods of transfection include the use of calcium phosphate co-precipitates, conventional mechanical procedures such as microinjection, electroporation, insertion of a plasmid encased in liposomes, or the use of virus vectors, or other methods known in the art. One method uses a eukaryotic viral vector, such as simian virus 40 (SV40) or bovine papillomavirus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell can be a yeast cell (e.g., *Saccharomyces cerevisiae*), or can be a mammalian cell, including a human cell.

A variety of host-expression vector systems can be utilized to express a phytase polynucleotide sequence such as SEQ ID NO:1 or SEQ ID NO:7, a coding sequence of SEQ ID NO:1 or a mutant phytase polynucleotide such as SEQ ID NO:9. Such host-expression systems represent vehicles by which the nucleotide sequences of interest can be produced and subsequently purified, and also represent cells that, when transformed or transfected with the appropriate nucleotide coding sequences, can express a protein, including a variant or mutant polypeptide or peptide portion thereof in situ. Such cells include, but are not limited to, microorganisms such as bacteria (e.g., *E. coli, B. subtilis*) transformed with recombinant bacteriophage DNA, plasmid DNA or cosmid DNA expression vectors containing a polynucleotide, or oligonucleotide portion thereof (wild type, variant or other mutant); yeast (e.g., *Saccharomyces*, *Pichia*) transformed with recombinant yeast expression vectors containing a polynucleotide, or oligonucleotide portions thereof (wild type, variant or other mutant); insect cell systems infected with recombinant virus expression vectors (e.g., baculovirus) containing a polynucleotide, or oligonucleotide portion thereof (wild type, variant or other mutant); plant cell systems infected with recombinant virus expression vectors (e.g., cauliflower mosaic virus or tobacco mosaic virus) or transformed with recombinant plasmid expression vectors (e.g., Ti plasmid) containing a mutant polynucleotide, or oligonucleotide portion thereof; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the phytase protein (wild type, variant or other phytase mutant) being expressed. For example, when a large quantity of such a protein is to be produced, for the generation of antibodies, or to screen peptide libraries, vectors that direct the expression of high levels of fusion protein products that are readily purified can be desirable. Such vectors include, but are not limited to, the *E. coli* expression vector pUR278 (Ruther et al., 1983, EMBO J. 2:1791), in which a phytase polynucleotide, or oligonucleotide portion thereof (wild type, variant or other mutant) can be ligated individually into the vector in frame with the lac Z coding region so that a fusion protein is produced; pIN vectors (Inouye and Inouye, Nucl. Acids Res. 13:3101-3109, 1985; Van Heeke and Schuster, J. Biol. Chem. 264:5503-5509, 1989); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned phytase protein, variant or mutant can be released from the GST moiety.

In an insect system, *Autographa californica* nuclear polyhedrosis virus (AcNPV) is used as a vector to express foreign genes. The virus grows in *Spodoptera frugiperda* cells. A phytase polynucleotide, or oligonucleotide portion thereof can be cloned individually into non-essential regions (for example the polyhedrin gene) of the virus and placed under control of an AcNPV promoter (for example the polyhedrin promoter). Successful insertion of a phytase polynucleotide, or oligonucleotide portion thereof will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see Smith et al., 1983, J. Virol. 46:584; U.S. Pat. No. 4,215,051).

In mammalian host cells, a number of viral-based expression systems can be utilized. In cases where an adenovirus is used as an expression vector, a phytase polynucleotide, or oligonucleotide portion thereof, can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome such as the E1 or E3 region results in a recombinant virus that is viable and capable of expressing a phytase protein (e.g., wild-type, variants or mutants thereof) in infected hosts (Logan and Shenk, Proc. Natl. Acad. Sci., USA 81:3655-3659, 1984). Specific initiation signals can also be required for efficient translation of an inserted phytase sequence. These signals include the ATG initiation codon and adjacent sequences. Where an entire polynucleotide, including its own initiation codon and adjacent sequences, is inserted into the appropriate expression vector, no additional translational control signals can be needed. However, where only a portion of a sequence is inserted, exogenous translational control signals, including, for example, an ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, and the like (see Bittner et al., Meth. Enzymol. 153:516-544, 1987).

In addition, a host cell strain can be chosen which modulates the expression of the inserted sequences, or modifies and processes the expressed polypeptide in a specific fashion. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein being expressed. To this end, eukaryotic host cells which possess the cellular machinery for proper processing of the primary transcript, glycosylation, and phosphorylation of the polypeptide can be used. Such mammalian host cells include, but are not limited to, CHO, VERO, BHK, HeLa, COS, MDCK, 293, 3T3, W138, and the like.

For long term, high yield production of recombinant proteins, stable expression is preferred. For example, cell lines that stably express a protein, including wild-type, variants or mutants of phytase, can be engineered. Rather than using expression vectors which contain viral origins of replication, host cells can be transformed with DNA controlled by appropriate expression control elements (e.g., promoter and/or enhancer sequences, transcription terminators, polyadenylation sites, and the like), and a selectable marker. Following the introduction of the foreign DNA, engineered cells can be grown for 1-2 days in an enriched media, then switched to selective media. The selectable marker in the recombinant plasmid confers resistance to the selection and allows cells to stably integrate the plasmid into their chromosomes and grow to form foci, which can be cloned and expanded into cell lines. This method can advantageously be used to engineer cell lines that express a phytase variant or mutant polypeptide. Such engineered cell lines can be particularly useful in screening and evaluation of compounds that affect the endogenous activity of a variant or mutant phytase polypeptide. Such engineered cell lines also can be useful to discriminate between factors that have specific vs. non-specific effects. In particular, mutant cell lines should lack key functions, and various mutations can be used to identify key functional domains using in vivo assays.

A number of selection systems can be used, including but not limited to the herpes simplex virus thymidine kinase (Wigler et al., Cell 11:223, 1977), hypoxanthine-guanine phosphoribosyltransferase (Szybalska and Szybalski, Proc. Natl. Acad. Sci. USA 48:2026, 1962), and adenine phosphoribosyltransferase (Lowy et al., Cell 22:817, 1980) genes can be employed in tk⁻, hgprt⁻ or aprt⁻ cells, respectively. Also, antimetabolite resistance can be used as the basis of selection for dhfr, which confers resistance to methotrexate (Wigler et al., Proc. Natl. Acad. Sci. USA 77:3567, 1980; O'Hare et al., Proc. Natl. Acad. Sci. USA 78:1527, 1981); gpt, which confers resistance to mycophenolic acid Mulligan and Berg, Proc. Natl. Acad. Sci. USA 78:2072, 1981); neo, which confers resistance to the aminoglycoside G-418 (Colberre-Garapin et al., J. Mol. Biol. 150:1, 1981); and hygro, which confers resistance to hygromycin (Santerre et al., Gene 30:147, 1984) genes. Accordingly, the invention provides a vector that contains a mutant phytase polynucleotide, or oligonucleotide portion thereof, or one or more primers or their complements, including an expression vector that contains any of the foregoing sequences operatively associated with a regulatory element that directs the expression of a coding sequence or primer; and also provides a host cell that contains any of the foregoing sequences, alone or operatively associated with a regulatory element, which can directs expression of a polypeptide encoded the polynucleotide, as appropriate.

A homolog of a mutant phytase polynucleotide sequence can be isolated by performing a polymerase chain reaction (PCR; see U.S. Pat. No. 4,683,202, which is incorporated herein by reference) using two oligonucleotide primers, including degenerate primer pools designed on the basis of the amino acid sequences of a phytase polypeptide such as that set forth in SEQ ID NO:8 (*E. coli* appA "wild type" phytase) or an exemplary phytase of the invention, as disclosed herein. The template for the reaction can be cDNA obtained by reverse transcription of mRNA prepared from organisms known to express a phytase enzyme or homologue. The PCR product can be subcloned and sequenced or manipulated in any number of ways (e.g., further manipulated by nested PCR) to insure that the amplified sequences represent the sequences of a phytase or mutant polynucleotide sequence. The PCR fragment can then be used to isolate a full length cDNA clone (including clones containing a mutant polynucleotide sequence) by labeling the amplified fragment and screening a nucleic acid library (e.g., a bacteriophage cDNA library). Alternatively, the labeled fragment can be used to screen a genomic library (for review of cloning strategies, see, for example, Sambrook et al., supra, 1989; Ausubel et al., supra, 1989).

Phytase polypeptides that have been modified from the wild-type amino acid sequence, include substitutions of amino acid residues, for example, negatively charged amino acids include aspartic acid and glutamic acid; positively charged amino acids include lysine and arginine; amino acids with uncharged polar head groups having similar hydrophilicity values include the following: leucine, isoleucine, valine, glycine, alanine, asparagine, glutamine, serine, threonine, phenylalanine and tyrosine. In many cases, however, a nucleotide substitution can be silent, resulting in no change in the encoded polypeptide.

Mutant phytase polypeptides and peptide portions thereof that are substantially identical to the phytase polypeptide SEQ ID NO:2 or SEQ ID NO:8 (*E. coli* appA "wild type" phytase) or peptide portions thereof are encompassed within the scope of the invention.

Synthetic polypeptides or peptides can be prepared by chemical synthesis, for example, solid-phase chemical peptide synthesis methods, which are well known (see, for example, Merrifield, J. Am. Chem. Soc., 85:2149-2154, 1963; Stewart and Young, Solid Phase Peptide Synthesis, Second ed., Pierce Chemical Co., Rockford, Ill., pp. 11-12), and have been employed in commercially available laboratory peptide design and synthesis kits (Cambridge Research Biochemicals). Such commercially available laboratory kits have generally utilized the teachings of Geysen et al., Proc. Natl. Acad. Sci., USA, 81:3998 (1984) and provide for synthesizing peptides upon the tips of a multitude of rods or pins, each of which is connected to a single plate. When such a system is utilized, a plate of rods or pins is inverted and inserted into a second plate of corresponding wells or reservoirs, which contain solutions for attaching or anchoring an appropriate amino acid to the tips of the pins or rods. By repeating such a process step, i.e., inverting and inserting the tips of the rods or pins into appropriate solutions, amino acids are built into desired peptides.

A number of available FMOC peptide synthesis systems are available. For example, assembly of a polypeptide or fragment can be carried out on a solid support using an Applied Biosystems, Inc., Model 431A automated peptide synthesizer. Such equipment provides ready access to the peptides of the invention, either by direct synthesis or by synthesis of a series of fragments that can be coupled using other known techniques. Accordingly, methods for the chemical synthesis of polypeptides and peptides are well-known to those of ordinary skill in the art, e.g., peptides can be synthesized by solid phase techniques, cleaved from the resin and purified by preparative high performance liquid chromatography (see, e.g., Creighton, 1983, Proteins: Structures and Molecular Principles, W.H. Freeman & Co., N.Y., pp. 50-60). The composition of the synthetic peptides can be confirmed by amino acid analysis or sequencing; e.g., using the Edman degradation procedure (see e.g., Creighton, 1983, supra at pp. 34-49). Thus, fragments of the phytase polypeptide, variant, or mutant can be chemically synthesized.

In one aspect of the invention, a method for producing an phytase enzyme, such as those shown in FIG. 1, is provided. The method includes growing a host cell which contains a polynucleotide encoding the enzyme (e.g., SEQ ID NO:1, 7 or 9), under conditions which allow the expression of the nucleic acid, and optionally isolating the enzyme encoded by the nucleic acid. Methods of culturing the host cell are described in the Examples and are known by those of skill in the art.

In a particular embodiment, the present invention provides for the expression of phytase in transgenic plants or plant organs and methods for the production thereof. DNA expression constructs are provided for the transformation of plants with a gene encoding phytase under the control of regulatory sequences which are capable of directing the expression of phytase. These regulatory sequences include sequences capable of directing transcription in plants, either constitutively, or in stage and/or tissue specific manners.

The manner of expression depends, in part, on the use of the plant or parts thereof. The transgenic plants and plant organs provided by the present invention may be applied to a variety of industrial processes either directly, e.g. in animal feeds or alternatively, the expressed phytase may be extracted and if desired, purified before application. Alternatively, the recombinant host plant or plant part may be used directly. In a particular aspect, the present invention provides methods of catalyzing phytate-hydrolyzing reactions using seeds containing enhanced amounts of phytase. The method involves contacting transgenic, non-wild type seeds, preferably in a ground or chewed form, with phytate-containing substrate and allowing the enzymes in the seeds to increase the rate of reaction. By directly adding the seeds to a phytate-containing substrate, the invention provides a solution to the expensive and problematic process of extracting and purifying the enzyme. In a particular—but by no means limiting—exemplification, the present invention also provides methods of treatment whereby an organism lacking a sufficient supply of an enzyme is administered the enzyme in the form of seeds containing enhanced amounts of the enzyme. In a preferred embodiment, the timing of the administration of the enzyme to an organism is coordinated with the consumption of a phytate-containing foodstuff.

The expression of phytase in plants can be achieved by a variety of means. Specifically, for example, technologies are available for transforming a large number of plant species, including dicotyledonous species (e.g. tobacco, potato, tomato, Petunia, *Brassica*). Additionally, for example, strategies for the expression of foreign genes in plants are available. Additionally still, regulatory sequences from plant genes have been identified that are serviceable for the construction of chimeric genes that can be functionally expressed in plants and in plant cells (e.g. Klee et al., 1987; Clark et al., 1990; Smith et al., 1990).

The introduction of gene constructs into plants can be achieved using several technologies including transformation with *Agrobacterium tumefaciens* or *Agrobacterium rhizogenes*. Non-limiting examples of plant tissues that can be transformed thusly include protoplasts, microspores or pollen, and explants such as leaves, stems, roots, hypocotyls, and cotyls. Furthermore, DNA can be introduced directly into protoplasts and plant cells or tissues by microinjection, electroporation, particle bombardment, and direct DNA uptake.

Proteins may be produced in plants by a variety of expression systems. For instance, the use of a constitutive promoter such as the 35S promoter of Cauliflower Mosaic Virus (Guilley et al., 1982) is serviceable for the accumulation of the expressed protein in virtually all organs of the transgenic plant. Alternatively, the use of promoters that are highly tissue-specific and/or stage-specific are serviceable for this invention (Higgins, 1984; Shotwell, 1989) in order to bias expression towards desired tissues and/or towards a desired stage of development. Further details relevant to the expression in plants of the phytase molecules of the instant invention are disclosed, for example, in U.S. Pat. No. 5,770,413 (Van Ooijen et al.) and U.S. Pat. No. 5,593,963 (Van Ooijen et al.), although these references do not teach the inventive molecules of the instant application and instead teach the use of fungal phytases.

In sum, it is relevant to this invention that a variety of means can be used to achieve the recombinant expression of phytase in a transgenic plant or plant part. Such a transgenic plants and plant parts are serviceable as sources of recombinantly expressed phytase, which can be added directly to phytate-containing sources. Alternatively, the recombinant plant-expressed phytase can be extracted away from the plant source and, if desired, purified prior to contacting the phytase substrate.

Within the context of the present invention, plants to be selected include, but are not limited to crops producing edible flowers such as cauliflower (*Brassica oleracea*), artichoke (*Cynara scolymus*), fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut, *Arachis hypogeae*), orange (*Citrus*, e.g. *maxima*), peach (*Prunus*, e.g. *persica*), pear (*Pyra*, e.g. *communis*), plum (*Prunus*, e.g. *domestica*), strawberry (*Fragaria*, e.g. *moschata*), tomato (*Lycopersicon*, e.g. *esculentum*), leafs, such as alfalfa (*Medicago*, e.g. *sativa*), cabbages (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*), roots, such as arrowroot (*Maranta*, e.g. *arundinacea*), beet (*Beta*, e.g *vulgaris*), carrot (*Daucus*, e.g. *carota*), cassaya (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*) and seeds, such as bean (*Phaseolus*, e.g. *vulgaris*), pea (*Pisum*, e.g. *sativum*), soybean (*Glycin*, e.g. max), wheat (*Triticum*, e.g. *aestivum*), barley (*Hordeum*, e.g. *vulgare*), corn (*Zea*, e.g. *mays*), rice (*Oryza*, e.g. *sativa*), rapeseed (*Brassica napus*), millet (*Panicum* L.), sunflower (*Helianthus annus*), oats (*Avena sativa*), tubers, such as kohlrabi (*Brassica*, e.g. *oleraceae*), potato (*Solanum*, e.g. *tuberosum*) and the like.

It is understood that additional plant as well as non-plant expression systems can be used within the context of this invention. The choice of the plant species is primarily determined by the intended use of the plant or parts thereof and the amenability of the plant species to transformation.

Several techniques are available for the introduction of the expression construct containing the phytase-encoding DNA sequence into the target plants. Such techniques include but are not limited to transformation of protoplasts using the calcium/polyethylene glycol method, electroporation and microinjection or (coated) particle bombardment (Potrykus, 1990). In addition to these so-called direct DNA transformation methods, transformation systems involving vectors are widely available, such as viral vectors (e.g. from the Cauliflower Mosaic Cirus (CaMV) and bacterial vectors (e.g. from the genus *Agrobacterium*) (Potrykus, 1990). After selection and/or screening, the protoplasts, cells or plant parts that have been transformed can be regenerated into whole plants, using methods known in the art (Horsch et al., 1985). The choice of the transformation and/or regeneration techniques is not critical for this invention.

For dicots, a preferred embodiment of the present invention uses the principle of the binary vector system (Hoekema et al., 1983; EP 0120516 Schilperoort et al.) in which *Agrobacterium* strains are used which contain a vir plasmid with the virulence genes and a compatible plasmid containing the gene construct to be transferred. This vector can replicate in both *E. coli* and in *Agrobacterium*, and is derived from the binary vector Bin19 (Bevan, 1984) which is altered in details that are not relevant for this invention. The binary vectors as used in this example contain between the left- and right-border sequences of the T-DNA, an identical NPTII-gene coding for kanamycin resistance (Bevan, 1984) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerfull methods for introduction of genetic material into plant cells has facilitated transformation. Presently the methods of choice for transformation of monocots are microprojectile bombardment of explants or suspension cells, and direct DNA uptake or electroporation of protoplasts. For example, transgenic rice plants have been successfully obtained using the bacterial hph gene, encoding hygromycin resistance, as a selection marker. The gene was introduced by electroporation (Shimamoto et al., 1993). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm et al., 1990). The introduction of genetic material into aleurone protoplasts of other monocot crops such as wheat and barley has been reported (Lee et al., 1989). Wheat plants have been regenerated from embryogenic suspension culture by selecting only the aged compact and nodular embryogenic callus tissues for the establishment of the embryogenic suspension cultures (Vasil et al., 1972: Vasil et al., 1974). The combination with transformation systems for these crops enables the application of the present invention to monocots. These methods may also be applied for the transformation and regeneration of dicots.

Expression of the phytase construct involves such details as transcription of the gene by plant polymerases, translation of mRNA, etc. that are known to persons skilled in the art of recombinant DNA techniques. Only details relevant for the proper understanding of this invention are discussed below. Regulatory sequences which are known or are found to cause expression of phytase may be used in the present invention. The choice of the regulatory sequences used depends on the target crop and/or target organ of interest. Such regulatory sequences may be obtained from plants or plant viruses, or may be chemically synthesized. Such regulatory sequences are promoters active in directing transcription in plants, either constitutively or stage and/or tissue specific, depending on the use of the plant or parts thereof. These promoters include, but are not limited to promoters showing constitutive expression, such as the 35S promoter of Cauliflower Mosaic Virus (CaMV) (Guilley et al., 1982), those for leaf-specific expression, such as the promoter of the ribulose bisphosphate carboxylase small subunit gene (Coruzzi et al., 1984), those for root-specific expression, such as the promoter from the glutamin synthase gene (Tingey et al., 1987), those for seed-specific expression, such as the cruciferin A promoter from *Brassica napus* (Ryan et al., 1989), those for tuber-specific expression, such as the class-I patatin promoter from potato (Koster-Topfer et al., 1989; Wenzler et al., 1989) or those for fruit-specific expression, such as the polygalacturonase (PG) promoter from tomato (Bird et al., 1988).

Other regulatory sequences such as terminator sequences and polyadenylation signals include any such sequence functioning as such in plants, the choice of which is within the level of the skilled artisan. An example of such sequences is the 3' flanking region of the nopaline synthase (nos) gene of *Agrobacterium tumefaciens* (Bevan, supra). The regulatory sequences may also include enhancer sequences, such as found in the 35S promoter of CaMV, and mRNA stabilizing sequences such as the leader sequence of Alfalfa Mosaic Cirus (AlMV) RNA4 (Brederode et al., 1980) or any other sequences functioning in a like manner.

The phytase should be expressed in an environment that allows for stability of the expressed protein. The choice of cellular compartments, such as cytosol, endoplasmic reticulum, vacuole, protein body or periplasmic space can be used in the present invention to create such a stable environment, depending on the biophysical parameters of the phytase. Such parameters include, but are not limited to pH-optimum, sensitivity to proteases or sensitivity to the molarity of the preferred compartment.

To obtain expression in the cytoplasm of the cell, the expressed enzyme should not contain a secretory signal peptide or any other target sequence. For expression in chloroplasts and mitochondria the expressed enzyme should contain specific so-called transit peptide for import into these organelles. Targeting sequences that can be attached to the enzyme of interest in order to achieve this are known (Smeekens et al., 1990; van den Broeck et al., 1985; Wolter et al., 1988). If the activity of the enzyme is desired in the vacuoles a secretory signal peptide has to be present, as well as a specific targeting sequence that directs the enzyme to these vacuoles (Tague et al., 1990). The same is true for the protein bodies in seeds. The DNA sequence encoding the enzyme of interest should be modified in such a way that the enzyme can exert its action at the desired location in the cell.

To achieve extracellular expression of the phytase, the expression construct of the present invention utilizes a secretory signal sequence. Although signal sequences which are homologous (native) to the plant host species are preferred, heterologous signal sequences, i.e. those originating from other plant species or of microbial origin, may be used as well. Such signal sequences are known to those skilled in the art. Appropriate signal sequences which may be used within the context of the present invention are disclosed in Blobel et al., 1979; Von Heijne, 1986; Garcia et al., 1987; Sijmons et al., 1990; Ng et al., 1994; and Powers et al., 1996).

All parts of the relevant DNA constructs (promoters, regulatory-, secretory-, stabilizing-, targeting-, or termination sequences) of the present invention may be modified, if desired, to affect their control characteristics using methods known to those skilled in the art. It is pointed out that plants containing phytase obtained via the present invention may be used to obtain plants or plant organs with yet higher phytase levels. For example, it may be possible to obtain such plants or plant organs by the use of somoclonal variation techniques or by cross breeding techniques. Such techniques are well known to those skilled in the art.

In one embodiment, the instant invention provides a method (and products thereof) of achieving a highly efficient overexpression system for phytase and other molecules. In one aspect, the instant invention provides a method (and products thereof) of achieving a highly efficient overexpression system for phytase and pH 2.5 acid phosphatase in *Trichoderma*. This system results in enzyme compositions that have particular utility in the animal feed industry. Additional details regarding this approach are in the public literature and/or are known to the skilled artisan. In a particular non-limiting exemplification, such publicly available literature includes EP 0659215 (WO 9403612 A1) (Nevalainen et al.), although these references do not teach the inventive molecules of the instant application.

In one embodiment, the instant invention provides a method (and products thereof) of producing stabilized aqueous liquid formulations having phytase activity that exhibit increased resistance to heat inactivation of the enzyme activity and which retain their phytase activity during prolonged periods of storage. The liquid formulations are stabilized by means of the addition of urea and/or a polyol such as sorbitol and glycerol as stabilizing agent. Also provided are feed preparations for monogastric animals and methods for the production thereof that result from the use of such stabilized aqueous liquid formulations. Additional details regarding this approach are in the public literature and/or are known to the skilled artisan. In a particular non-limiting exemplification, such publicly available literature includes EP 0626010 (WO 9316175 A1) (Barendse et al.), although references in the publicly available literature do not teach the inventive molecules of the instant application.

In one embodiment, the instant invention provides a method of hydrolyzing phytate comprised of contacting the phytate with one or more of the novel phytase molecules disclosed herein. Accordingly, the invention provides a method for catalyzing the hydrolysis of phytate to inositol and free phosphate with release of minerals from the phytic acid complex. The method includes contacting a phytate substrate with a degrading effective amount of an enzyme of the invention, such as the enzyme shown in SEQ ID NO:2. The term "degrading effective" amount refers to the amount of enzyme which is required to degrade at least 50% of the phytate, as compared to phytate not contacted with the enzyme. Preferably, at least 80% of the phytate is degraded.

In another embodiment, the invention provides a method for hydrolyzing phospho-mono-ester bonds in phytate. The method includes administering (e.g., to an individual, e.g., a human, or an animal) an effective amount of a phytase of the invention (e.g., a phytase having a sequence identity of at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97.5%, 98%, 98.5%, 99%, 99.5%, or more, or complete (100%) sequence identity (i.e., homology) to SEQ ID NO:2 (a phytase polypeptide); SEQ ID NO:10 (a phytase polypeptide); a polypeptide having sequence as set forth in SEQ ID NO:8 and having at least one, or all, of the amino acid modifications W68E, Q84W, A95P, K97C, S168E, R181Y, N226C, Y277D, wherein the polypeptide has phytase activity) or other phytases, for example, the E. coli appA "wild type" phytase-encoding SEQ ID NO:7, or, a polypeptide sequence of SEQ ID NO:2 or the E. coli appA "wild type" phytase SEQ ID NO:8, to yield inositol and free phosphate. An "effective" amount refers to the amount of enzyme which is required to hydrolyze at least 50% of the phospho-mono-ester bonds, as compared to phytate not contacted with the enzyme.

In a particular aspect, when desired, the phytase molecules may be used in combination with other reagents, such as other catalysts; in order to effect chemical changes (e.g. hydrolysis) in the phytate molecules and/or in other molecules of the substrate source(s). According to this aspect, the phytase molecules and the additional reagent(s) will not inhibit each other, or, the phytase molecules and the additional reagent(s) will have an overall additive effect, or, the phytase molecules and the additional reagent(s) will have an overall synergistic effect.

Relevant sources of the substrate phytate molecules include foodstuffs, potential foodstuffs, byproducts of foodstuffs (both in vitro byproducts and in vivo byproducts, e.g. ex vivo reaction products and animal excremental products), precursors of foodstuffs, and any other material source of phytate.

In a non-limiting apsect, the recombinant phytase can be consumed by organisms and retains activity upon consumption. In another exemplification, transgenic approches can be used to achieve expression of the recombinant phytase—in one aspect, in a controlled fashion (methods are available for controlling expression of transgenic molecules in time-specific and tissue specific manners).

In a particular exemplification, the phytase activity in the source material (e.g. a transgenic plant source or a recombinant prokaryotic host) may be increased upon consumption; this increase in activity may occur, for example, upon conversion of a precursor phytase molecule in pro-form to a significantly more active enzyme in a more mature form, where said conversion may result, for example, from the injestion and digestion of the phytase source. Hydrolysis of the phytate substrate may occur at any time upon the contacting of the phytase with the phytate; for example, this may occur before injestion or after injestion or both before and after injestion of either the substrate or the enzyme or both. It is additionally appreciated that the phytate substrate may be contacted with—in addition to the phytase—one or more additional reagents, such as another enzyme, which may be also be applied either directly or after purification from its source material.

It is appreciated that the phytase source material(s) can be contacted directly with the phytate source material(s); e.g. upon in vitro or in vivo grinding or chewing of either or both the phytase source(s) and the phytate source(s). Alternatively the phytase enzyme may be purified away from source material(s), or the phytate substrate may be purified away from source material(s), or both the phytase enzyme and the phytate substrate may be purified away from source material(s) prior to the contacing of the phytase enzyme with the phytate substrate. It is appreciated that a combination of purified and unpurified reagents—including enzyme(s) or substrates(s) or both—may be used.

It is appreciated that more than one source material may be used as a source of phytase activity. This is serviceable as one way to achieve a timed release of reagent(s) from source material(s), where release from different reagents from their source materials occur differentially, for example as injested source materials are digested in vivo or as source materials are processed in in vitro applications. The use of more than one source material of phytase activity is also serviceable to obtain phytase activities under a range of conditions and fluctuations thereof, that may be encountered—such as a range of pH values, temperatures, salinities, and time intervals—for example during different processing steps of an application. The use of different source materials is also serviceable in order to obtain different reagents, as exemplified by one or more forms or isomers of phytase and/or phytate &/or other materials.

It is appreciated that a single source material, such a trangenic plant species (or plant parts thereof), may be a source material of both phytase and phytate; and that enzymes and substrates may be differentially compartmentalized within said single source—e.g. secreted vs. non-secreted, differentially expressed &/or having differential abundances in different plant parts or organs or tissues or in subcellular compartments within the same plant part or organ or tissue. Purification of the phytase molecules contained therein may comprise isolating and/or further processing of one or more desirable plant parts or organs or tissues or subcellular compartments.

In a particular aspect, this invention provides a method of catalyzing in vivo and/or in vitro reactions using seeds containing enhanced amounts of enzymes. The method comprises adding transgenic, non-wild type seeds, preferably in a ground form, to a reaction mixture and allowing the enzymes in the seeds to increase the rate of reaction. By directly adding the seeds to the reaction mixture the method provides a solution to the more expensive and cumbersome process of extracting and purifying the enzyme. Methods of treatment are also provided whereby an organism lacking a sufficient supply of an enzyme is administered the enzyme in the form of seeds from one or more plant species, preferably transgenic plant species, containing enhanced amounts of the enzyme. Additional details regarding this approach are in the public literature and/or are known to the skilled artisan. In a particular non-limiting exemplification, such publicly available literature includes U.S. Pat. No. 5,543,576 (Van Ooijen et al.) and U.S. Pat. No. 5,714,474 (Van Ooijen et al.), although these reference do not teach the inventive molecules of the instant application and instead teach the use of fungal phytases.

In one aspect, the instant phytase molecules are serviceable for generating recombinant digestive system life forms (or microbes or flora) and for the administration of said recombinant digestive system life forms to animals. Administration may be optionally performed alone or in combination with other enzymes &/or with other life forms that can provide enzymatic activity in a digestive system, where said other enzymes and said life forms may be recombinant or otherwise. For example, administration may be performed in combination with xylanolytic bacteria In a non-limiting aspect, the present invention provides a method for steeping corn or sorghum kernels in warm water containing sulfur dioxide in the presence of an enzyme preparation comprising one or more phytin-degrading enzymes, preferably in such an amount that the phytin present in the corn or sorghum is substantially degraded. The enzyme preparation may comprise phytase and/or acid phosphatase and optionally other plant material degrading enzymes. The steeping time may be 12 to 18 hours. The steeping may be interrupted by an intermediate milling step, reducing the steeping time. In a preferred embodiment, corn or sorghum kernels are steeped in warm water containing sulfur dioxide in the presence of an enzyme preparation including one or more phytin-degrading enzymes, such as phytase and acid phosphatases, to eliminate or greatly reduce phytic acid and the salts of phytic acid. Additional details regarding this approach are in the public literature and/or are known to the skilled artisan. In a particular non-limiting exemplification, such publicly available literature includes U.S. Pat. No. 4,914,029 (Caransa et al.) and EP 0321004 (Vaara et al.), although these references do not teach the inventive molecules of the instant application.

In a non-limiting aspect, the present invention provides a method to obtain a bread, dough having desirable physical properties such as non-tackiness and elasticity and a bread product of superior quality such as a specific volume comprising adding phytase molecules to the bread dough. In a preferred embodiment, phytase molecules of the instant invention are added to a working bread dough preparation that is subsequently formed and baked. Additional details regarding this approach are in the public literature and/or are known to the skilled artisan. In a particular non-limiting exemplification, such publicly available literature includes JP 03076529 (Hara et al.), although this reference does not teach the inventive phytase molecules of the instant application.

In a non-limiting aspect, the present invention provides a method to produce improved soybean foodstuffs. Soybeans are combined with phytase molecules of the instant invention to remove phytic acid from the soybeans, thus producing soybean foodstuffs that are improved in their supply of trace nutrients essential for consuming organisms and in its digestibility of proteins. In a preferred embodiment, in the production of soybean milk, phytase molecules of the instant invention are added to or brought into contact with soybeans in order to reduce the phytic acid content. In a non-limiting exemplification, the application process can be accelerated by agitating the soybean milk together with the enzyme under heating or by a conducting a mixing-type reaction in an agitation container using an immobilized enzyme. Additional details regarding this approach are in the public literature and/or are known to the skilled artisan. In a particular non-limiting exemplification, such publicly available literature includes JP 59166049 (Kamikubo et al.), although this reference does not teach the inventive molecules of the instant application.

In one aspect, the instant invention provides a method of producing an admixture product for drinking water or animal feed in fluid form, and which comprises using mineral mixtures and vitamin mixtures, and also novel phytase molecules of the instant invention. In a preferred embodiment, there is achieved a correctly dosed and composed mixture of necessary nutrients for the consuming organism without any risk of precipitation and destruction of important minerals/vitamins, while at the same time optimum utilization is made of the phytin-bound phosphate in the feed. Additional details regarding this approach are in the public literature and/or are known to the skilled artisan. In a particular non-limiting exemplification, such publicly available literature includes EP 0772978 (Bendixen et al.), although this reference does not teach the inventive molecules of the instant application.

It is appreciated that the phytase molecules of the instant invention may also be used to produce other alcoholic and non-alcoholic drinkable foodstuffs (or drinks) based on the use of molds &/or on grains &/or on other plants. These drinkable foodstuffs include liquors, wines, mixed alcoholic drinks (e.g. wine coolers, other alcoholic coffees such as Irish coffees, etc.), beers, near-beers, juices, extracts, homogenates, and purees. In a preferred exemplification, the instantly disclosed phytase molecules are used to generate transgenic versions of molds &/or grains &/or other plants serviceable for the production of such drinkable foodstuffs. In another preferred exemplification, the instantly disclosed phytase molecules are used as additional ingredients in the manufacturing process &/or in the final content of such drinkable foodstuffs. Additional details regarding this approach are in the public literature and/or are known to the skilled artisan. However—due to the novelty of the instant invention—references in the publicly available literature do not teach the inventive molecules instantly disclosed.

In another non-limiting exemplification, the present invention provides a means to obtain refined sake having a reduced amount of phytin and an increased content of inositol. Such a sake may have—through direct &/or psychogenic effects—a preventive action on hepatic disease, arteriosclerosis, and other diseases. In a preferred embodiment, a sake is produced from rice Koji by multiplying a rice Koji mold having high phytase activity as a raw material. It is appreciated that the phytase molecules of the instant invention may be used to produce a serviceable mold with enhanced activity (preferably a transgenic mold) &/or added exogenously to augment the effects of a Koji mold. The strain is added to boiled rice and Koji is produced by a conventional procedure. In a preferred exemplification, the prepared Koji is used, the whole rice is prepared at two stages and Sake is produced at constant Sake temperature of 15° C. to give the objective refined Sake having a reduced amount of phytin and an increased amount of inositol. Additional details regarding this approach are in the public literature and/or are known to the skilled artisan. In a particular non-limiting exemplification, such publicly available literature includes JP 06153896 (Soga et al.) and JP 06070749 (Soga et al.), although these references do not teach the inventive molecules of the instant application In a non-limiting aspect, the present invention provides a method to obtain an absorbefacient capable of promoting the absorption of minerals including ingested calcium without being digested by gastric juices or intestinal juices at a low cost. In a preferred embodiment, said mineral absorbefacient contains a partial hydrolysate of phytic acid as an active ingredient. Preferably, a partial hydrolyzate of the phytic acid is produced by hydrolyzing the phytic acid or its salts using novel phytase molecules of the instant invention. The treatment with said phytase molecules may occur either alone &/or in a combination treatment (to inhibit or to augment the final effect), and is followed by inhibiting the hydrolysis within a range so as not to liberate all the phosphate radicals. Additional details regarding this approach are in the public literature and/or are known to the skilled artisan.

In a particular non-limiting exemplification, such publicly available literature includes JP 04270296 (Hoshino), although reference in the publicly available literature do not teach the inventive molecules of the instant application.

In a non-limiting aspect, the present invention provides a method (and products therefrom) to produce an enzyme composition having an additive or preferably a synergistic phytate hydrolyzing activity; said composition comprises novel phytase molecules of the instant invention and one or more additional reagents to achieve a composition that is serviceable for a combination treatment. In a preferred embodiment, the combination treatment of the present invention is achieved with the use of at least two phytases of different position specificity, i.e. any combinations of 1-, 2-, 3-, 4-, 5-, and 6-phytases. By combining phytases of different position specificity an additive or synergistic effect is obtained. Compositions such as food and feed or food and feed additives comprising such phytases in combination are also included in this invention as are processes for their preparation. Additional details regarding this approach are in the public literature and/or are known to the skilled artisan. In a particular non-limiting exemplification, such publicly available literature includes WO9 830681 (Ohmann et al.), although references in the publicly available literature do not teach the use of the inventive molecules of the instant application.

In one aspect, the combination treatment of the present invention is achieved with the use of an acid phosphatase having phytate hydrolyzing activity at a pH of 2.5, in a low ratio corresponding to a pH 2.5:5.0 activity profile of from about 0.1:1.0 to 10:1, preferably of from about 0.5:1.0 to 5:1, more preferably still of from about 0.8:1.0 to 3:1, and more preferably still of from about 0.8:1.0 to 2:1. Said enzyme composition can displays a higher synergetic phytate hydrolyzing efficiency through thermal treatment. Said enzyme composition is serviceable in the treatment of foodstuffs (drinkable and solid food, feed and fodder products) to improve phytate hydrolysis. Additional details regarding this approach are in the public literature and/or are known to the skilled artisan. In a particular non-limiting exemplification, such publicly available literature includes U.S. Pat. No. 5,554,399 (Vanderbeke et al.) and U.S. Pat. No. 5,443,979 (Vanderbeke et al.), although these reference do not teach the use of the inventive molecules of the instant application, but rather teach the use of fungal (in particular *Aspergillus*) phytases.

In a non-limiting aspect, the present invention provides a method (and products therefrom) to produce compositions comprised of the instant novel phytate-acting enzyme in combination with one or more additional enzymes that act on polysaccharides. Such polysaccharides can be selected from the group consisting of arabinans, fructans, fucans, galactans, galacturonans, glucans, mannans, xylans, levan, fucoidan, carrageenan, galactocarolose, pectin, pectic acid, amylose, pullulan, glycogen, amylopectin, cellulose, carboxylmethylcellulose, hydroxypropylmethylcellulose, dextran, pustulan, chitin, agarose, keratan, chondroitin, dermatan, hyaluronic acid, alginic acid, and polysaccharides containing at least one aldose, ketose, acid or amine selected from the group consisting of erythrose, threose, ribose, arabinose, xylose, lyxose, allose, altrose, glucose, mannose, gulose, idose, galactose, talose, erythrulose, ribulose, xylulose, psicose, fructose, sorbose, tagatose, glucuronic acid, gluconic acid, glucaric acid, galacturonic acid, mannuronic acid, glucosamine, galactosamine and neuraminic acid In a particular aspect, the present invention provides a method (and products therefrom) to produce composition having a synergistic phytate hydrolyzing activity comprising one or more novel phytase molecules of the instant invention, a cellulase (in one aspect including but not exclusively a xylanase), optionally a protease, and optionally one or more additonal reagents. In preferred embodiments, such combination treatments are serviceable in the treatment of foodstuffs, wood products, such as paper products, and as cleansing solutions and solids.

In one non-limiting exemplification, the instant phytase molecules are serviceable in combination with cellulosome components. It is known that cellulases of many cellulolytic bacteria are organized into discrete multienzyme complexes, called cellulosomes. The multiple subunits of cellulosomes are composed of numerous functional domains, which interact with each other and with the cellulosic substrate. One of these subunits comprises a distinctive new class of noncatalytic scaffolding polypeptide, which selectively integrates the various cellulase and xylanase subunits into the cohesive complex. Intelligent application of cellulosome hybrids and chimeric constructs of cellulosomal domains should enable better use of cellulosic biomass and may offer a wide range of novel applications in research, medicine and industry.

In another non-limiting exemplification, the instant phytase molecules are serviceable—either alone or in combination treatments—in areas of biopulping and biobleaching where a reduction in the use of environmentally harmful chemicals traditionally used in the pulp and paper industry is desired. Waste water treatment represents another vast application area where biological enzymes have been shown to be effective not only in colour removal but also in the bioconversion of potentially noxious substances into useful bioproducts.

In another non-limiting exemplification, the instant phytase molecules are serviceable for generating life forms that can provide at least one enzymatic activity—either alone or in combination treatments—in the treatment of digestive systems of organisms. Particularly relevant organisms to be treated include non-ruminant organisms. Specifically, it is appreciated that this approach may be performed alone or in combination with other biological molecules (for example, xylanases) to generate a recombinant host that expresses a plurality of biological molecules. It is also appreciated that the administration of the instant phytase molecules &/or recombinant hosts expressing the instant phytase molecules may be performed either alone or in combination with other biological molecules, &/or life forms that can provide enzymatic activities in a digestive system—where said other enzymes and said life forms may be may recombinant or otherwise. For example, administration may be performed in combination with xylanolytic bacteria For example, in addition to phytate, many organisms are also unable to adequately digest hemicelluloses. Hemicelluloses or xylans are major components (35%) of plant materials. For ruminant animals, about 50% of the dietary xylans are degraded, but only small amounts of xylans are degraded in the lower gut of nonruminant animals and humans. In the rumen, the major xylanolytic species are *Butyrivibrio fibrisolvens* and *Bacteroides ruminicola*. In the human colon, *Bacteroides ovatus* and *Bacteroides fragilis* subspecies "a" are major xylanolytic bacteria. Xylans are chemically complex, and their degradation requires multiple enzymes. Expression of these enzymes by gut bacteria varies greatly among species. *Butyrivibrio fibrisolvens* makes extracellular xylanases but *Bacteroides* species have cell-bound xylanase activity. Biochemical characterization of xylanolytic enzymes from gut bacteria has not been done completely. A xylosidase gene has been cloned from *B. fibrosolvens* 113.

The data from DNA hybridizations using a xylanase gene cloned from *B. fibrisolvens* 49 indicate this gene may be present in other *B. fibrisolvens* strains. A cloned xylanase from *Bact. ruminicola* was transferred to and highly expressed in *Bact. fragilis* and *Bact. uniformis*. Arabinosidase and xylosidase genes from *Bact. ovatus* have been cloned and both activities appear to be catalyzed by a single, bifunctional, novel enzyme.

Accordingly, it is appreciated that the present phytase molecules are serviceable for 1) transferring into a suitable host (such as *Bact. fragilis* or *Bact. uniformis*); 2) achieving adequate expression in a resultant recombinant host; and 3) administering said recombinant host to organisms to improve the ability of the treated organisms to degrade phytate. Continued research in genetic and biochemical areas will provide knowledge and insights for manipulation of digestion at the gut level and improved understanding of colonic fiber digestion.

Additional details regarding this approach are in the public literature and/or are known to the skilled artisan. In a particular non-limiting exemplification, such publicly available literature includes U.S. Pat. No. 5,624,678 (Bedford et al.), U.S. Pat. No. 5,683,911 (Bodie et al.), U.S. Pat. No. 5,720,971 (Beauchemin et al.), U.S. Pat. No. 5,759,840 (Sung et al.), U.S. Pat. No. 5,770,012 (Cooper), U.S. Pat. No. 5,786,316 (Baeck et al.), U.S. Pat. No. 5,817,500 (Hansen et al.), and journal articles (Jeffries, 1996; Prade, 1996; Bayer et al., 1994; Duarte et al., 1994; Hespell & Whitehead, 1990; Wong et al., 1988), although these reference do not teach the inventive phytase molecules of the instant application, nor do they all teach the addition of phytase molecules in the production of foodstuffs, wood products, such as paper products, and as cleansing solutions and solids. In contrast, the instant invention teaches that phytase molecules—preferably the inventive phytase molecules of the instant application—may be added to the reagent(s) disclosed in order to obtain preparations having an additional phytase activity. Preferably, said reagent(s) and the additional phytase molecules and will not inhibit each other, more preferably said reagent(s) and the additional phytase molecules will have an overall additive effect, and more preferably still said reagent(s) and the additional phytase molecules will have an overall synergistic effect.

In a non-limiting aspect, the present invention provides a method (and products therefrom) for enhancement of phytate phosphorus utilization and treatment and prevention of tibial dyschondroplasia in animals, particularly poultry, by administering to animals a feed composition containing a hydroxylated vitamin $D_3$ derivative. The vitamin $D_3$ derivative can be administered to animals in feed containing reduced levels of calcium and phosphorus for enhancement of phytate phosphorus utilization. Accordingly, the vitamin $D_3$ derivative can be administered in combination with novel phytase molecules of the instant invention for further enhancement of phytate phosphorus utilization. Additional details regarding this approach are in the public literature and/or are known to the skilled artisan. In a particular non-limiting exemplification, such publicly available literature includes U.S. Pat. No. 5,516,525 (Edwards et al.) and U.S. Pat. No. 5,366,736 (Edwards et al.), U.S. Pat. No. 5,316,770 (Edwards et al.) although these references do not teach the inventive molecules of the instant application.

In a non-limiting aspect, the present invention provides a method (and products thereof) to obtain foodstuff that 1) comprises phytin that is easily absorbed and utilized in a form of inositol in a body of an organism; 2) that is capable of reducing phosphorus in excrementary matter; and 3) that is accordingly useful for improving environmental pollution. Said foodstuff is comprised of an admixture of a phytin-containing grain, a lactic acid-producing microorganism, and a novel phytase molecule of the instant invention. In a preferred embodiment, said foodstuff is produced by compounding a phytin-containing grain (preferably, e.g. rice bran) with an effective microbial group to be added having an acidophilic property, producing lactic acid, without producing butyric acid, free from pathogenicity, and a phytase. Examples of an effective microbial group to be added include e.g. *Streptomyces* sp. (ATCC 3004) belonging to the group of *actinomyces* and *Lactobacillus* sp. (IFO 3070) belonging to the group of *lactobacilli*. Further, a preferable amount of an effective microbial group to be added is 0.2 wt. % in terms of bacterial body weight based on a grain material. Furthermore, the amount of the addition of the phytase to be added can be 1-2 wt. % based on the phytin in the grain material. Additional details regarding this approach are in the public literature and/or are known to the skilled artisan. In a particular non-limiting exemplification, such publicly available literature includes JP 08205785 (Akahori et al.), although references in the publicly available literature do not teach the inventive molecules of the instant application.

In a non-limiting aspect, the present invention provides a method for improving the solubility of vegetable proteins. More specifically, the invention relates to methods for the solubilization of proteins in vegetable protein sources, which methods comprise treating the vegetable protein source with an effective amount of one or more phytase enzymes—including phytase molecules of the instant invention—and treating the vegetable protein source with an effective amount of one or more proteolytic enzymes. In another aspect, the invention provides animal feed additives comprising a phytase and one or more proteolytic enzymes. Additional details regarding this approach are in the public literature and/or are known to the skilled artisan. In a particular non-limiting exemplification, such publicly available literature includes EP 0756457 (WO 9528850 A1) (Nielsen and Knap), although references in the publicly available literature do not teach the inventive molecules of the instant application.

In a non-limiting aspect, the present invention provides a method of producing a plant protein preparation comprising dispersing vegetable protein source materials in water at a pH in the range of 2 to 6 and admixing phytase molecules of the instant invention therein. The acidic extract containing soluble protein is separated and dried to yield a solid protein of desirable character. One or more proteases can also be used to improve the characteristics of the protein. Additional details regarding this approach are in the public literature and/or are known to the skilled artisan. In a particular non-limiting exemplification, such publicly available literature includes U.S. Pat. No. 3,966,971 (Morehouse et al.), although references in the publicly available literature do not teach the inventive molecules of the instant application.

In a non-limiting aspect, the present invention provides a method (and products thereof) to activate inert phosphorus in soil and/or compost, to improve the utilization rate of a nitrogen compound, and to suppress propagation of pathogenic molds by adding three reagents, phytase, saponin and chitosan, to the compost. In a non-limiting embodiment the method can comprise treating the compost by 1) adding phytase-containing microorganisms in media—preferably recombinant hosts that overexpress the novel phytase molecules of the instant invention—e.g. at 100 ml media/100 kg wet compost; 2) alternatively also adding a phytase-containing plant source—such as wheat bran—e.g. at 0.2 to 1 kg/100 kg wet compost; 3) adding a saponin-containing source— such as peat, mugworts and yucca plants—e.g. at 0.5 to 3.0 g/kg; 4) adding chitosan-containing materials—such as pulverized shells of shrimps, crabs, etc.—e.g. at 100 to 300 g/kg wet compost. In another non-limiting embodiment, recombinant forms the three reagents, phytase, saponin, and chitosan, are used. Additional details regarding this approach are in the public literature and/or are known to the skilled artisan. In a particular non-limiting exemplification, such publicly available literature includes JP 07277865 (Toya Taisuke), although references in the publicly available literature do not teach the inventive molecules of the instant application.

Fragments of the full length gene of the present invention may be used as a hybridization probe for a cDNA or a genomic library to isolate the full length DNA and to isolate other DNAs which have a high sequence similarity to the gene or similar biological activity. Probes of this type have at least 10, preferably at least 15, and even more preferably at least 30 bases and may contain, for example, at least 50 or more bases. The probe may also be used to identify a DNA clone corresponding to a full length transcript and a genomic clone or clones that contain the complete gene including regulatory and promotor regions, exons, and introns.

The present invention provides methods for identifying nucleic acid molecules that encode members of the phytase polypeptide family in addition to SEQ ID NO:1. In these methods, a sample, e.g., a nucleic acid library, such as a cDNA library, that contains a nucleic acid encoding a phytase polypeptide is screened with a phytase-specific probe, e.g., a phytase-specific nucleic acid probe. Phytase-specific nucleic acid probes are nucleic acid molecules (e.g., molecules containing DNA or RNA nucleotides, or combinations or modifications thereof) that specifically hybridize to nucleic acids encoding phytase polypeptides, or to complementary sequences thereof. The term "phytase-specific probe," in the context of this method of invention, refers to probes that bind to nucleic acids encoding phytase polypeptides, or to complementary sequences thereof, to a detectably greater extent than to nucleic acids encoding other enzymes, or to complementary sequences thereof.

The invention facilitates production of phytase-specific nucleic acid probes. Methods for obtaining such probes can be designed based on the amino acid sequences shown in FIGS. 1a and 1b. The probes, which can contain at least 12, e.g., at least 15, 25, 35, 50, 100, or 150 nucleotides, can be produced using any of several standard methods (see, e.g., Ausubel et al., supra). For example, preferably, the probes are generated using PCR amplification methods. In these methods, primers are designed that correspond to phytase-conserved sequences (see FIGS. 1a and 1b), which can include phytase-specific amino acids, and the resulting PCR product is used as a probe to screen a nucleic acid library, such as a cDNA library.

This invention can be used to isolate nucleic acid sequences substantially similar to the isolated nucleic acid molecule encoding an phytase enzyme disclosed in FIGS. 1a and 1b (SEQ ID NO:1). Isolated nucleic acid sequences are substantially similar if: (i) they are capable of hybridizing under stringent conditions, hereinafter described, to SEQ ID NO:1; or (ii) they encode a phytase polypeptide as set forth in SEQ ID NO:2 due to the degeneracy of the genetic code (e.g., degenerate to SEQ ID NO:1).

Degenerate DNA sequences encode the amino acid sequence of SEQ ID NO:2, but have variations in the nucleotide coding sequences. As used herein, "substantially similar" refers to the sequences having similar identity to the sequences of the instant invention. The nucleotide sequences that are substantially similar can be identified by hybridization or by sequence comparison. Enzyme sequences that are substantially similar can be identified by one or more of the following: proteolytic digestion, gel electrophoresis and/or microsequencing.

One means for isolating a nucleic acid molecule encoding a phytase enzyme is to probe a genomic gene library with a natural or artificially designed probe using art recognized procedures (see, e.g., Ausubel et al., supra). It is appreciated to one skilled in the art that SEQ ID NO:1, or fragments thereof (comprising at least 15 contiguous nucleotides), is a particularly useful probe. Other particular useful probes for this purpose are hybridizable fragments to the sequences of SEQ ID NO:1 (i.e., comprising at least 15 contiguous nucleotides).

It is also appreciated that such probes can be and can be labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other animal sources or to screen such sources for related sequences.

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acid is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/mL polyriboadenylic acid. Approximately $2\times10^7$ cpm (specific activity $4-9\times10^8$ cpm/ug) of $^{32}P$ end-labeled oligenucleotide probe are then added to the solution. After 12-16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm−10° C. for the oligonucleotide probe. The membrane is then exposed to autoradiographic film for detection of hybridization signals.

The nucleic acid molecules of the invention can be used as templates in standard methods for production of phytase gene products (e.g., phytase RNAs and phytase polypeptides). In addition, the nucleic acid molecules that encode phytase polypeptides (and fragments thereof) and related nucleic acids—such as (1) nucleic acids containing sequences that are complementary to, or that hybridize to, nucleic acids encoding phytase polypeptides, or fragments thereof (e.g., fragments containing at least 12, 15, 20, or 25 nucleotides); and (2) nucleic acids containing sequences that hybridize to sequences that are complementary to nucleic acids encoding phytase polypeptides, or fragments thereof (e.g., fragments containing at least 12, 15, 20, or 25 nucleotides)—can be used in methods focused on their hybridization properties. For example, as is described in further detail herein, such nucleic acid molecules can be used in the following methods: PCR methods for synthesizing phytase nucleic acids, methods for detecting the presence of a phytase nucleic acid in a sample, screening methods for identifying nucleic acids encoding new phytase family members. Hybridization-based uses include Southern-type, Northern-type, RNA protection, and any hybridization procedure were a nucleic acid is used as a hybridization partner.

Fragments or portions of the polynucleotides of the present invention may be used to synthesize full-length polynucleotides of the present invention. Accordingly, fragments or portions of the enzymes of the present invention may be employed for producing the corresponding full-length enzyme by peptide synthesis; therefore, the fragments may be employed as intermediates for producing the full-length enzymes. Size separation of the cleaved fragments is generally performed using 8 percent polyacrylamide gel as described in the literature (e.g. by Goeddel et al., 1980).

This invention provides enzymes, as well as fragments, other derivatives, and analogs thereof, and the corresponding nucleotides for use in directed evolution. The discovery and use of a plurality of templates as disclosed herein may significantly increase the potential yield of directed evolution in comparison to the directed evolution of a single template protein. Hence, the need for discovery is based on the premise that nature provides a wealth of potentially unattainable or unpredictable features in distinct but related members of molecular groupings, and that the exploitation of these features may greatly facilitate directed evolution. Thus, in one aspect, related but distinct molecules may serve as unique starting templates for the directed evolution of a desired characteristic. In another aspect, they may serve as repositories of structure-function information including, but not limited to, a variety of consensus motifs. Both utilities help to obviate the logistically impractical task of at once exploring an overly wide range of mutational permutations on any given molecule. For example, the full range of mutational permutations on a 100 amino acid protein includes over $10^{130}$ possibilities (assuming there are 20 amino acid possibilities at each position), a number too large for practical consideration.

Accordingly, particularly because of logistical and technical constraints, it is a desirable approach—in performing "directed evolution"—to discover and to make use of a plurality of related starting templates that have pre-evolved differences. These templates can then be subjected to a variety of mutagenic manipulations including, by way of non-limiting exemplification, DNA mutagenesis and combinatorial enzyme development, an approach that is further elaborated in co-pending U.S. Pat. No. 5,830,696 (Short et al.).

The enzyme activities of the novel molecules generated can then be screened by a variety of methods including, by way of non-limiting exemplification: a) molecular biopanning; b) recombinant clone screening; and c) extract screening.

This invention provides enzymes, as well as fragments, other derivatives, and analogs thereof, and cells expressing them that can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, 1975), the trioma technique, the human B-cell hybridoma technique (Kozbor et al., 1983), and the EBV-hybridoma technique to produce human monoclonal antibodies (Cole et al., 1985, pp. 77-96).

Techniques described for the production of single chain antibodies (U.S. Pat. No. 4,946,778 Ladner et al.) can be adapted to produce single chain antibodies to immunogenic enzyme products of this invention. Also, transgenic mice may be used to express humanized antibodies to immunogenic enzyme products of this invention.

Antibodies generated against the enzyme of the present invention may be used in screening for similar enzymes from other organisms and samples. Such screening techniques are known in the art. Antibodies may also be employed as a probe to screen gene libraries generated from this or other organisms to identify this or cross reactive activities.

Isolation and purification of polypeptides produced in the systems described above can be carried out using conventional methods, appropriate for the particular system. For example, preparative chromatography and immunological separations employing antibodies, such as monoclonal or polyclonal antibodies, can be used.

As is mentioned above, antigens that can be used in producing phytase-specific antibodies include phytase polypeptides, e.g., any of the phytase shown in Table 3 or polypeptide fragments thereof. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

Phytase-specific polyclonal and monoclonal antibodies can be purified, for example, by binding to, and elution from, a matrix containing a phytase polypeptide, e.g., the phytase polypeptide (or fragment thereof) to which the antibodies were raised. Additional methods for antibody purification and concentration are well known in the art and can be practiced with the phytase-specific antibodies of the invention (see, e.g., Coligan et al., 1996).

Anti-idiotype antibodies corresponding to phytase-specific antigens are also included in the invention, and can be produced using standard methods. These antibodies are raised to phytase-specific antibodies, and thus mimic phytase-specific epitopes.

This invention also includes additional uses of fragments of the phytase polypeptides that retain at least one phytase-specific activity or epitope. Phytase activity can be assayed by examining the catalysis of phytate to inositol and free phosphate. Such fragments can easily be identified by comparing the sequences of phytases found in FIGS. 1a and 1b.

In a non-limiting exemplification, a phytase polypeptide fragment containing, e.g., at least 8-10 amino acids can be used as an immunogen in the production of phytase-specific antibodies. The fragment can contain, for example, an amino acid sequence that is conserved in phytases, and this amino acid sequence can contain amino acids that are conserved in phytases. In another non-limiting exemplification, the above-described phytase fragments can be used in immunoassays, such as ELISAs, to detect the presence of phytase-specific antibodies in samples.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene is incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If micro-injection is to be used with avian species, however, a published procedure by Love et al., (Biotechnology, 12, Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include bovine, porcine, ovine and avian animals (e.g., cow, pig, sheep, chicken). The "transgenic non-human animals" of the invention are produced by introducing "transgenes" into the germ-line of the non-human animal. Embryonal target cells at various developmental stages can be used to introduce transgenes. Different methods are used depending on the stage of development of the embryonal target cell. The zygote is the best target for micro-injection. The use of zygotes as is target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles, 50% of the resulting animals will include the exogenous genetic material within one allele and 25% will include no exogenous genetic material.

In the microinjection method useful in the practice of the subject invention, the transgene is digested and purified free from any vector DNA, e.g., by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retroviral infection (Jaenich, R., Proc. Natl. Acad. Sci USA 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82: 6927-6931, 1985; Van der Putten, et al., Proc. Natl. Acad. Sci USA 82: 6148-6152, 1985). Transfection is easily and efficiently obtained by culturing the blastomeres on a monolayer of virus-producing cells (Van der Putten, supra; Stewart, et al., EMBO J. 6: 383-388, 1987). Alternatively, infection can be performed at a later stage. Virus or virus-producing cells can be injected into the blastocoele (D. Jahner et al., Nature 298: 623-628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al., Nature 292:154-156, 1981; M. O. Bradley et al., Nature 309:255-258, 1984; Gossler, et al., Proc. Natl. Acad. Sci USA 83:9065-9069, 1986; and Robertson et al., Nature 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468-1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode phytases or polypeptides having phytase activity, and include polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

The transgene to be used in the practice of the subject invention is a DNA sequence comprising a sequence coding for a phytase or a polypeptide having phytase activity. In a one embodiment, a polynucleotide having a sequence as set forth in SEQ ID NO:1 or a sequence encoding a polypeptide having a sequence as set forth in SEQ ID NO:2 is the transgene as the term is defined herein. Where appropriate, DNA sequences that encode proteins having phytase activity but differ in nucleic acid sequence due to the degeneracy of the genetic code may also be used herein, as may truncated forms, allelic variants and interspecies homologues.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood or tissue samples using transgene specific probes. PCR is particularly useful in this regard. Positive progeny (G0) are crossbred to produce offspring (G1) which are analyzed for transgene expression by Northern blot analysis of tissue samples.

In one aspect, the present invention provides compositions and methods for increasing the phosphorous uptake in an animal (including a human, a commercially used animal, or, a transgenic animal) by decreasing the amount of phytate pollutant in the manure of the animal (e.g., transgenic organism) by about 15%, 20%, 30%, about 20% to about 50%, 40%, 50%, 50%, 50%, 50%, or more.

Animals used in the practice of the subject invention include, but are not limited to, those animals generally regarded as domesticated animals including pets (e.g., canines, felines, avian species etc.) and those useful for the processing of food stuffs, i.e., avian such as meat bred and egg laying chicken and turkey, ovine such as lamb, bovine such as beef cattle and milk cows, piscine and porcine.

In one aspect, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

In some instances it may be advantageous to deliver and express a phytase sequence of the invention locally (e.g., within a particular tissue or cell type). For example, local expression of a phytase or digestive enzyme in the gut of an animal will assist in the digestion and uptake of, for example, phytate and phosporous, respectively. The nucleic sequence may be directly delivered to the salivary glands, tissue and cells and/or to the epithelial cells lining the gut, for example. Such delivery methods are known in the art and include electroporation, viral vectors and direct DNA uptake. Any polypeptide having phytase activity can be utilized in the methods of the invention (e.g., those specficially described herein, as well as those described in other sections of the invention).

For example, nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency, wherein the delivery vehicle will be dispersed within larger particles comprising a dried hydrophilic excipient material.

One such delivery vehicles comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) CIRC. RES. 71:1508-1517, the disclosure of which is incorporated herein by reference. A suitable adenovirus gene delivery is described in Rosenfeld et al. (1991) SCIENCE 252:431-434, the disclosure of which is incorporated herein by reference. Both retroviral and adenovirus delivery systems are described in Friedman (1989) SCIENCE 244:1275-1281, the disclosure of which is also incorporated herein by reference.

A second type of nucleic acid delivery vehicle comprises liposomal transfection vesicles, including both anionic and cationic liposomal constructs. The use of anionic liposomes requires that the nucleic acids be entrapped within the liposome. Cationic liposomes do not require nucleic acid entrapment and instead may be formed by simple mixing of the nucleic acids and liposomes. The cationic liposomes avidly bind to the negatively charged nucleic acid molecules, including both DNA and RNA, to yield complexes which give reasonable transfection efficiency in many cell types. See, Farhood et al. (1992) BIOCHEM. BIOPHYS. ACTA. 1111: 239-246, the disclosure of which is incorporated herein by reference. A particularly preferred material for forming liposomal vesicles is lipofectin which is composed of an equimolar mixture of dioleylphosphatidyl ethanolamine (DOPE) and dioleyloxypropyl-triethylammonium (DOTMA), as described in Felgner and Ringold (1989) NATURE 337:387-388.

In one aspect, the invention combines these two types of delivery systems. For example, Kahn et al. (1992), supra., teaches that a retrovirus vector may be combined in a cationic DEAE-dextran vesicle to further enhance transformation efficiency. It is also possible to incorporate nuclear proteins into viral and/or liposomal delivery vesicles to even further improve transfection efficiencies. See, Kaneda et al. (1989) SCIENCE 243:375-378.

In another embodiment, the invention provides digestive aids containing a phytase, e.g., an enzyme of the invention, either as the sole active ingredient or in combination with one or more other agents and/or enzymes is provided (as described in co-pending application U.S. Ser. No. 09/580,937, entitled "Dietary Aids and Methods of Use Thereof," filed May 25, 2000). The use of enzymes and other agents in digestive aids of livestock or domesticated animals not only improves the animal's health and life expectancy but also assists in increasing the health of livestock and in the production of foodstuffs from livestock.

Currently, some types of feed for livestock (e.g., certain poultry feed) are highly supplemented with numerous minerals (e.g., inorganic phosphorous), enzymes, growth factors, drugs, and other agents for delivery to the livestock. These supplements replace many of the calories and natural nutrients present in grain, for example. By reducing or eliminating the inorganic phosphorous supplement and other supplements (e.g., trace mineral salts, growth factors, enzymes, antibiotics) from the feed itself, the feed would be able to carry more nutrient and energy. Accordingly, the remaining diet would contain more usable energy. For example, grain-oilseed meal diets generally contain about 3,200 kcal metabolizable energy per kilogram of diet, and mineral salts supply no metabolizable energy. Removal of the unneeded minerals and substitution with grain would therefore increase the usable energy in the diet. Thus, the invention can be differentiated over commonly used phytase containing feed. For example, in one embodiment, a biocompatible material is used that is resistant to digestion by the gastrointestinal tract of an organism.

In many organisms, including, for example, poultry or birds such as, for example, chickens, turkeys, geese, ducks, parrots, peacocks, ostriches, pheasants, quail, pigeons, emu, kiwi, loons, cockatiel, cockatoo, canaries, penguins, flamingoes, and dove, the digestive tract includes a gizzard which stores and uses hard biocompatible objects (e.g., rocks and shells from shell fish) to help in the digestion of seeds or other feed consumed by a bird. A typical digestive tract of this general family of organisms, includes the esophagus which contains a pouch, called a crop, where food is stored for a brief period of time. From the crop, food moves down into the true stomach, or proventriculus, where hydrochloric acid and pepsin starts the process of digestion. Next, food moves into the gizzard, which is oval shaped and thick walled with powerful muscles. The chief function of the gizzard is to grind or crush food particles—a process which is aided by the bird swallowing small amounts of fine gravel or grit. From the gizzard, food moves into the duodenum. The small intestine of birds is similar to mammals. There are two blind pouches or ceca, about 4-6 inches in length at the junction of the small and large intestine. The large intestine is short, consisting mostly of the rectum about 3-4 inches in length. The rectum empties into the cloaca and feces are excreted through the vent.

Hard, biocompatible objects consumed (or otherwise introduced) and present in the gizzard provide a useful vector for delivery of various enzymatic, chemical, therapeutic and antibiotic agents. These hard substances have a life span of a few hours to a few days and are passed after a period of time. Accordingly, the invention provides coated, impregnated (e.g., impregnated matrix and membranes) modified dietary aids for delivery of useful digestive or therapeutic agents to an organism. Such dietary aids include objects which are typically ingested by an organism to assist in digestion within the gizzard (e.g., rocks or grit). The invention provides biocompatible objects that have coated thereon or impregnated therein agents useful as a digestive aid for an organism or for the delivery of a therapeutic or medicinal agent or chemical.

In a first embodiment, the invention provides a dietary aid, having a biocompatible composition designed for release of an agent that assists in digestion, wherein the biocompatible composition is designed for oral consumption and release in the digestive tract (e.g., the gizzard) of an organism. "Biocompatible" means that the substance, upon contact with a host organism (e.g., a bird), does not elicit a detrimental response sufficient to result in the rejection of the substance or to render the substance inoperable. Such inoperability may occur, for example, by formation of a fibrotic structure around the substance limiting diffusion of impregnated agents to the host organism therein or a substance which results in an increase in mortality or morbidity in the organism due to toxicity or infection. A biocompatible substance may be non-biodegradable or biodegradable. In one embodiment, the biocompatible composition is resistant to degradation or digestion by the gastrointestinal tract. In another embodiment, the biocompatible composition has the consistency of a rock or stone.

A non-biodegradable material useful in the invention is one that allows attachment or impregnation of a dietary agent. Such non-biodegradable materials include, for example, thermoplastics, such as acrylic, modacrylic, polyamide, polycarbonate, polyester, polyethylene, polypropylene, polystyrene, polysulfone, polyethersulfone, and polyvinylidene fluoride. Elastomers are also useful materials and include, for example, polyamide, polyester, polyethylene, polypropylene, polystyrene, polyurethane, polyvinyl alcohol and silicone (e.g., silicone based or containing silica). The invention provides that the biocompatible composition can contain a plurality of such materials, which can be, e.g., admixed or layered to form blends, copolymers or combinations thereof.

As used herein, a "biodegradable" material means that the composition will erode or degrade in vivo to form smaller chemical species. Degradation may occur, for example, by enzymatic, chemical or physical processes. Suitable biodegradable materials contemplated for use in the invention include poly(lactide)s, poly(glycolide)s, poly(lactic acid)s, poly(glycolic acid)s, polyanhydrides, polyorthoesters, polyetheresters, polycaprolactone, polyesteramides, polycarbonate, polycyanoacrylate, polyurethanes, polyacrylate. Such materials can be admixed or layered to form blends, copolymers or combinations thereof.

It is contemplated that a number of different biocompatible substances may be ingested or otherwise provided to the same organism simultaneously, or in various combinations (e.g., one material before the other). In addition, the biocompatible substance may be designed for slow passage through the digestive tract. For example, large or fatty substances tend to move more slowly through the digestive tract, accordingly, a biocompatible material having a large size to prevent rapid passing in the digestive tract can be used. Such large substances can be a combination of non-biodegradable and biodegradable substances. For example, a small non-biodegradable substance can be encompassed by a biodegradable substance such that over a period of time the biodegradable portion will be degraded allowing the non-biodegradable portion to pass through the digestive trace. In addition, it is recognized that any number of flavorings can be provided to the biocompatible substance to assist in consumption.

Any number of agents alone or in combination with other agents can be coated on the biocompatible substance including polypeptides (e.g., enzymes, antibodies, cytokines or therapeutic small molecules), and antibiotics, for example. Examples of particular useful agents are listed in Table 1 and 2, below. It is also contemplated that cells can be encapsulated into the biocompatible material of the invention and used to deliver the enzymes or therapeutics. For example, porous substances can be designed that have pores large enough for cells to grow in and through and that these porous materials can then be taken into the digestive tract. For example, the biocompatible substance can be comprised of a plurality of microfloral environments (e.g., different porosity, pH etc.) that provide support for a plurality of cell types. The cells can be genetically engineered to deliver a particular drug, enzyme or chemical to the organism. The cells can be eukaryotic or prokaryotic.

TABLE 1

| Treatment Class | Chemical | Description |
| --- | --- | --- |
| Antibiotics | Amoxycillin and Its Combination Mastox Injection (Amoxycillin and Cloxacillin) | Treatment Against Bacterial Diseases Caused By Gram + and Gram – Bacteria |
| | Ampicillin and Its Combination Biolox Injection (Ampicillin and Cloxacillin) | Treatment Against Bacterial Diseases Caused By Gram + And Gram – Bacteria. |
| | Nitrofurazone + Urea Nefrea Bolus | Treatment Of Genital Infections |
| | Trimethoprim + Sulphamethoxazole Trizol Bolus | Treatment Of Respiratory Tract Infections, Gastro Intestinal Tract Infections, Urino- Genital Infections. |
| | Metronidazole and Furazolidone Metofur Bolus | Treatment Of Bacterial And Protozoal Diseases. |
| | Phthalylsulphathiazole, Pectin and Kaolin Pectolin Bolus Suspension | Treatment Of Bacterial And Non-Specific Diarrhoea, Bacillary Dysentery And Calf Scours. |
| Antihelmintics | Ectoparasiticide Germex Ointment (Gamma Benzene Hexachloride, Proflavin Hemisulphate and Cetrimide) | Ectoparasiticide and Antiseptic |
| | Endoparasiticides > Albendazole and Its Combination Alben (Albendazole) Suspension (Albendazole 2.5%) Plus Suspension (Albendazole 5%) Forte Bolus (Albendazole 1.5 Gm.) Tablet (Albendazole 600 Mg.) Powder (Albendazole 5%, 15%) | Prevention And Treatment Of Roundworm, Tapeworm and Fluke Infestations |
| | Alpraz (Albendazole and Praziquantel)Tablet | Prevention And Treatment Of Roundworm and Tapeworm Infestation In Canines and Felines. |
| | Oxyclozanide and Its Combination Clozan (Oxyclozanide) Bolus, Suspension | Prevention and Treatment Of Fluke Infestations |
| | Tetzan (Oxyclozanide and Tetramisole Hcl) Bolus, Suspension | Prevention and Treatment Of Roundworm and Fluke Infestations |
| | Fluzan (Oxyclozanide and Levamisole Hcl) Bolus, Suspension | Prevention and Treatment Of Roundworm Infestations and Increasing Immunity |
| | Levamisole Nemasol Injection Wormnil Powder | Prevention and Treatment Of Roundworm Infestations and Increasing Immunity. |
| | Fenbendazole Fenzole Tablet (Fenbendazole 150 Mg.) Bolus (Fenbendazole 1.5 Gm.) Powder (Fenbendazole 2.5% W/W) | Prevention And Treatment of Roundworm and Tapeworm Infestations |
| Tonics | Vitamin B Complex, Amino Acids and Liver Extract Heptogen Injection | Treatment Of Anorexia, Hepatitis, Debility, Neuralgic Convulsions Emaciation and Stunted Growth. |

TABLE 1-continued

| Treatment Class | Chemical | Description |
|---|---|---|
| | Calcium Levulinate With Vit. $B_{12}$ and Vit $D_3$<br>Hylactin Injection | Prevention and treatment of hypocalcaemia, supportive therapy in sick conditions (especially hypothermia) and treatment of early stages of rickets. |
| Animal Feed Supplements | Essential Minerals, Selenium and Vitamin E<br>Gynolactin Bolus<br>Essential Minerals, Vitamin E, and Iodine<br>Hylactin Powder<br>Essential Electrolytes With Vitamin C<br>Electra - C Powder | Treatment Of Anoestrus Causing Infertility and Repeat Breeding In Dairy Animals and Horses. Infertility, Improper Lactation, Decreased Immunity, Stunted Growth and Debility. Diarrhoea, Dehydration, Prior to and after Transportation, In Extreme temperatures (High Or Low) and other Conditions of stress. |
| | Pyrenox Plus (Diclofenac Sodium + Paracetamol) Bolus, Injection. | Treatment Of Mastitis, Pyrexia Post Surgical Pain and Inflammation, Prolapse Of Uterus, Lameness and Arthritis. |

TABLE 2

Therapeutic Formulations

| Product | Description |
|---|---|
| Acutrim ® (phenylpropanolamine) | Once-daily appetite suppressant tablets. |
| The Baxter ® Infusor | For controlled intravenous delivery of anticoagulants, antibiotics, chemotherapeutic agents, and other widely used drugs. |
| Catapres-TTS ® (clonidine transdermal therapeutic system) | Once-weekly transdermal system for the treatment of hypertension. |
| Covera HS3 (verapamil hydrochloride) | Once-daily Controlled-Onset Extended-Release (COER-24) tablets for the treatment of hypertension and angina pectoris. |
| DynaCirc CR ® (isradipine) | Once-daily extended release tablets for the treatment of hypertension. |
| Efidac 24 ® (chlorpheniramine maleate) | Once-daily extended release tablets for the relief of allergy symptoms. |
| Estraderm ® (estradiol transdermal system) | Twice-weekly transdermal system for treating certain postmenopausal symptoms and preventing osteoporosis |
| Glucotrol XL ® (glipizide) | Once-daily extended release tablets used as an adjunct to diet for the control of hyperglycemia in patients with non-insulin-dependent diabetes mellitus. |
| IVOMEC SR ® Bolus (ivermectin) | Ruminal delivery system for season-long control of major internal and external parasites in cattle. |
| Minipress XL ® (prazosin) | Once-daily extended release tablets for the treatment of hypertension. |
| NicoDerm ® CQ ™ (nicotine transdermal system) | Transdermal system used as a once-daily aid to smoking cessation for relief of nicotine withdrawal symptoms. |
| Procardia XL ® (nifedipine) | Once-daily extended release tablets for the treatment of angina and hypertension. |
| Sudafed ® 24 Hour (pseudoephedrine) | Once-daily nasal decongestant for relief of colds, sinusitis, hay fever and other respiratory allergies. |
| Transderm-Nitro ® (nitroglycerin transdermal system) | Once-daily transdermal system for the prevention of angina pectoris due to coronary artery disease. |
| Transderm Scop ® (scopolamin transdermal system) | Transdermal system for the prevention of nausea and vomiting associated with motion sickness. |
| Volmax (albuterol) | Extended release tablets for relief of bronchospasm in patients with reversible obstructive airway disease. |
| Actisite ® | (tetracycline hydrochloride) Periodontal fiber used as an adjunct to scaling and root planing for reduction of pocket depth and bleeding on probing in patients with adult periodontitis. |
| ALZET ® | Osmotic pumps for laboratory research. |
| Amphotec ® (amphotericin B cholesteryl sulfate complex for injection) | AMPHOTEC ® is a fungicidal treatment for invasive aspergillosis in patients where renal impairment or unacceptable toxicity precludes use of amphotericin B in effective doses and in patients with invasive aspergillosis where prior amphotericin B therapy has failed. |

TABLE 2-continued

Therapeutic Formulations

| Product | Description |
| --- | --- |
| BiCitra ® (sodium citrate and citric acid) | Alkalinizing agent used in those conditions where long-term maintenance of alkaline urine is desirable. |
| Ditropan ® (oxybutynin chloride) | For the relief of symptoms of bladder instability associated with uninhibited neurogenic or reflex neurogenic bladder (i.e., urgency, frequency, urinary leakage, urge incontinence, dysuria). |
| Ditropan ® XL (oxybutynin chloride) | is a once-daily controlled-release tablet indicated for the treatment of overactive bladder with symptoms of urge urinary incontinence, urgency and frequency. |
| DOXIL ® (doxorubicin HCl liposome injection) | |
| Duragesic ® (fentanyl transdermal system) CII | 72-hour transdermal system for management of chronic pain in patients who require continuous opioid analgesia for pain that cannot be managed by lesser means such as acetaminophen-opioid combinations, non-steroidal analgesics, or PRN dosing with short-acting opioids. |
| Elmiron ® (pentosan polysulfate sodium) | Indicated for the relief of bladder pain or discomfort associated with interstitial cystitis. |
| ENACT AirWatch ™ | An asthma monitoring and management system. |
| Ethyol ® (amifostine) | Indicated to reduce the cumulative renal toxicity associated with repeated administration of cisplatin in patients with advanced ovarian cancer or non-small cell lung cancer. Indicated to reduce the incidence of moderate to severe xerostomia in patients undergoing post-operative radiation treatment for head and neck cancer, where the radiation port includes a substantial portion of the parotid glands. |
| Mycelex ® Troche (clotrimazole) | For the local treatment of oropharyngeal candidiasis. Also indicated prophylactically to reduce the incidence of oropharyngeal candidiasis in patients immunocompromised by conditions that include chemotherapy, radiotherapy, or steroid therapy utilized in the treatment of leukemia, solid tumors, or renal transplantation. |
| Neutra-Phos ® (potassium and sodium phosphate) | a dietary/nutritional supplement |
| PolyCitra ® -K Oral Solution and PolyCitra ® -K Crystals (potassium citrate and citric acid) | Alkalinizing agent useful in those conditions where long-term maintenance of an alkaline urine is desirable, such as in patents with uric acid and cystine calculi of the urinary tract, especially when the administration of sodium salts is undesirable or contraindicated |
| PolyCitra ® -K Syrup and LC (tricitrates) | Alkalinizing agent useful in those conditions where long-term maintenance of an alkaline urine is desirable, such as in patients with uric acid and cystine calculi of the urinary tract. |
| Progestasert ® (progesterone) | Intrauterine Progesterone Contraceptive System |
| Testoderm ® Testoderm ® with Adhesive and Testoderm ® TTS CIII | Testosterone Transdermal System The Testoderm ® products are indicated for replacement therapy in males for conditions associated with a deficiency or absence of endogenous testosterone: (1) Primary hypogonadism (congenital or acquired) or (2) Hypogonadotropic hypogonadism (congenital or acquired). |
| Viadur ™ (leuprolide acetate implant) | Once-yearly implant for the palliative treatment of prostate cancer |

Certain agents can be designed to become active or in activated under certain conditions (e.g., at certain pH's, in the presence of an activating agent etc.). In addition, it may be advantageous to use pro-enzymes in the compositions of the invention. For example, a pro-enzymes can be activated by a protease (e.g., a salivary protease that is present in the digestive tract or is artificially introduced into the digestive tract of an organism). It is contemplated that the agents delivered by the biocompatible compositions of the invention can be activated or inactivated by the addition of an activating agent which may be ingested by, or otherwise delivered to, the organism. Another mechanism for control of the agent in the digestive tract is an environment sensitive agent that is activated in the proper digestive compartment. For example, an agent may be inactive at low pH but active at neutral pH. Accordingly, the agent would be inactive in the gut but active in the intestinal tract. Alternatively, the agent can become active in response to the presence of a microorganism specific factor (e.g., microorganisms present in the intestine).

In summary, the potential benefits of the present invention include, for example, (1) reduction in or possible elimination of the need for mineral supplements (e.g., inorganic phosphorous supplements), enzymes, or therapeutic drugs for animal (including fish) from the daily feed or grain thereby increasing the amount of calories and nutrients present in the feed, and (2) increased health and growth of domestic and non-domestic animals including, for example, poultry, porcine, bovine, equine, canine, and feline animals.

A large number of enzymes can be used in the methods and compositions of the present invention. These enzymes include enzymes necessary for proper digestion of consumed foods, or for proper metabolism, activation or derivation of chemicals, prodrugs or other agents or compounds delivered to the animal via the digestive tract. Examples of enzymes that can be delivered or incorporated into the compositions of the invention, include, for example, feed enhancing enzymes selected from the group consisting of α-galactosidases, β-galactosidases, in particular lactases, phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phospholipases and cutinases. Phytases as set forth in SEQ ID NO:1 and 2 and in Table 3 below are preferred. The sequences described in Table 3 are SEQ ID NO:1 and 2 having the amino acid substitutions and nucleotide substitutions as described therein.

TABLE 3

| Designation | Source | AA seq | Nuc. Sequence |
|---|---|---|---|
| E. coli B (reference) | E. coli B | S10; P26; D176; M298; A299; G312; I428 | |
| 868PH1 | Bison E. coli | I428T | |
| 872PH1 | Kangaroo rat E. coli | D176G; G312S M298K; A299T | GAC(176)GGC; GGT(312)AGT; ATG(298)AAG; GCA(299)ACA |
| 875PH2 | E. coli W | A160S; D176G; M298K; A299T | GCG(160)TCG; GAC(176)GGC; ATG(298)AAG; GCA(299)ACA |
| 873PH1 | Calf E. coli | I428R | |
| E. coli B | E. coli B | K298M; T299A | AAG(298)ATG; ACA(299)GCA |
| K12 appA | E. coli K12 | M298K; A299T | ATG(298)AAG; GCA(299)ACA |

The enzymes used in the invention (including the phytases of the invention) can be modified to enhance their activity, delivery, activation and degradation. Such modifications can be performed in vivo or in vitro and use methods and processes generally known in the art as described more fully below. Such methodology generally uses polynucleotide or polypeptide sequences that are either synthesized by automated machines or are cloned, expressed, or manipulated by recombinant DNA techniques.

In a preferred embodiment, the enzyme used in the compositions (e.g., a dietary aid) of the present invention is a phytase enzyme (e.g., a phytase of the invention) which is stable to heat and is heat resistant and catalyzes the enzymatic hydrolysis of phytate, i.e., the enzyme is able to renature and regain activity after a brief (i.e., 5 to 30 seconds), or longer period, for example, minutes or hours, exposure to temperatures of above 50° C.

A "feed" and a "food," respectively, means any natural or artificial diet, meal or the like or components of such meals intended or suitable for being eaten, taken in, digested, by an animal and a human being, respectively. "Dietary Aid," as used herein, denotes, for example, a composition containing agents that provide a therapeutic or digestive agent to an animal or organism. A "dietary aid," typically is not a source of caloric intake for an organism, in other words, a dietary aid typically is not a source of energy for the organism, but rather is a composition which is taken in addition to typical "feed" or "food".

An agent or enzyme (e.g., a phytase) may exert its effect in vitro or in vivo, i.e. before intake or in the stomach or gizzard of the organism, respectively. Also a combined action is possible.

Although any enzyme may be incorporated into a dietary aid of the invention, reference is made herein to phytase as an exemplification of the methods and compositions of the invention. A dietary aid of the invention includes an enzyme (e.g., a phytase of the invention, e.g., a polypeptide having a sequence as set forth in SEQ ID NO:10). In one aspect, a dietary aid of the invention containing a phytase composition is liquid or dry.

Liquid compositions need not contain anything more than the enzyme (e.g. a phytase), preferably in a highly purified form. Usually, however, a stabilizer such as glycerol, sorbitol or mono propylen glycol is also added. The liquid composition may also comprise other additives, such as salts, sugars, preservatives, pH-adjusting agents, proteins, phytate (a phytase substrate). Typical liquid compositions are aqueous or oil-based slurries. The liquid compositions can be added to a biocompatible composition for slow release. Preferably the enzyme is added to a dietary aid composition that is a biocompatible material (e.g., biodegradable or non-biodegradable) and includes the addition of recombinant cells into, for example, porous microbeads.

Dry compositions may be spray dried compositions, in which case the composition need not contain anything more than the enzyme in a dry form. Usually, however, dry compositions are so-called granulates which may readily be mixed with a food or feed components, or more preferably, form a component of a pre-mix. The particle size of the enzyme granulates preferably is compatible with that of the other components of the mixture. This provides a safe and convenient means of incorporating enzymes into animal feed. Preferably the granulates are biocompatible and more preferably the biocompatible granulates are non-biodegradable.

Agglomeration granulates coated by an enzyme can be prepared using agglomeration techniques in a high shear mixer Absorption granulates are prepared by having cores of a carrier material to absorb be coated by the enzyme. Preferably the carrier material is a biocompatible non-biodegradable material that simulates the role of stones or grit in the gizzard of an animal. Typical filler materials used in agglomeration techniques include salts, such as disodium sulphate. Other fillers are kaolin, talc, magnesium aluminum silicate and cellulose fibres. Optionally, binders such as dextrins are also included in agglomeration granulates. The carrier materials can be any biocompatible material including biodegradable and non-biodegradable materials (e.g., rocks, stones, ceramics, various polymers). Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, the dietary aid compositions of the invention (e.g., phytase dietary aid compositions of the invention) may contain other substituents such as colouring agents, aroma compounds, stabilizers, vitamins, minerals, other feed or food enhancing enzymes etc. A typical additive usually comprises one or more compounds such as vitamins, minerals or feed enhancing enzymes and suitable carriers and/or excipients.

In one embodiment, the dietary aid compositions of the invention additionally comprises an effective amount of one or more feed enhancing enzymes, in particular feed enhancing enzymes selected from the group consisting of α-galactosidases, β-galactosidases, in particular lactases, other phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phospholipases and cutinases.

The animal dietary aid of the invention is supplemented to the mono-gastric animal before or simultaneously with the diet. In one embodiment, the dietary aid of the invention is supplemented to the mono-gastric animal simultaneously with the diet. In another embodiment, the dietary aid is added to the diet in the form of a granulate or a stabilized liquid.

Phytase activity is expressed as FYT, FTU, PU and U. All are same and one unit of phytase is defined as the amount of enzyme that liberates 1 micromole of inorganic phosphorus per minute from 1.5 millimole sodium phytate solution at 37° C. and pH 5.5. An effective amount of an enzyme in a dietary aid of the invention is from about 10-20,000; preferably from about 10 to 15,000, more preferably from about 10 to 10,000, in particular from about 100 to 5,000, especially from about 100 to about 2,000 FYT/kg dietary aid. In one aspect, phytases (e.g., a phytase of the invention) is administered (e.g., fed to the animal or individual) at a dosage of about 500 FYT per kg feed or 100 grams of phytase per ton feed with an activity of 5,000 FYT/gm, or 200 grams of phytase per ton feed with an activity of 2,500 FYT/gm. Other dosages can be administered, depending on the animal whose diet is to supplemented, and for what reason; for example, for poultry layers, add about 450 to 500 FYT per kg feed or 180 to 200 grams of phytase with an activity of 2,500 FYT/gm of phytase per ton feed.

Examples of other specific uses of a phytase of the invention is in soy processing and in the manufacture of inositol or derivatives thereof.

The invention also relates to a method for reducing phytate levels in animal manure, wherein the animal is fed a dietary aid containing an effective amount of the phytase of the invention. As stated in the beginning of the present application one important effect thereof is to reduce the phosphate pollution in the environment.

In another embodiment, the dietary aid of the invention is a magnetic carrier. For example, a magnetic carrier containing an enzyme (e.g., a phytase of the invention) distributed in, on or through a magnetic carrier (e.g., a porous magnetic bead), can be distributed over an area high in phytate and collected by magnets after a period of time. Such distribution and recollection of beads reduces additional pollution and allows for reuse of the beads. In addition, use of such magnetic beads in vivo allows for the localization of the dietary aid to a point in the digestive tract where, for example, phytase activity can be carried out. For example, a dietary aid of the invention containing digestive enzymes (e.g., a phytase) can be localized to the gizzard of the animal by juxtapositioning a magnet next to the gizzard of the animal after the animal consumes a dietary aid of magnetic carriers. The magnet can be removed after a period of time allowing the dietary aid to pass through the digestive tract. In addition, the magnetic carriers are suitable for removal from the organism after sacrificing or to aid in collection.

When the dietary aid of the invention is a porous particle, such particles can be impregnated by a substance with which to form a slow release particle. Such slow release particles may be prepared not only by impregnating the porous particles with the substance it is desired to release, but also by first dissolving the desired substance in the first dispersion phase. In this case, slow release particles prepared by the method in which the substance to be released is first dissolved in the first dispersion phase are also within the scope and spirit of the invention. The porous hollow particles may, for example, be impregnated by a slow release substance such as a medicine, agricultural chemical or enzyme. In particular, when porous hollow particles impregnated by an enzyme are made of a biodegradable polymers, the particles themselves may be used as an agricultural chemical or fertilizer, and they have no adverse effect on the environment. In one embodiment the porous particles are magnetic in nature.

The porous hollow particles may be used as a bioreactor support, in particular an enzyme support. Therefore, it is advantageous to prepare the dietary aid utilizing a method for slow release, for instance by encapsulating the enzyme of agent in a microvesicle, such as a liposome, from which the dose is released over the course of several days, preferably between about 3 to 20 days. Alternatively, the agent (e.g., an enzyme) can be formulated for slow release, such as incorporation into a slow release polymer from which the agent (e.g., enzyme) is slowly released over the course of several days, for example from 2 to 30 days and can range up to the life of the animal.

The invention also provides compositions, e.g., dietary aids, including phytases, such as the enzymes of the invention, in the form of liposomal-formulated compositions. Liposomes of the invention can be derived from phospholipids or other lipid substances. Liposomes can be formed by mono- or multilamellar hydrated liquid crystals that are dispersed in an aqueous medium. Any non-toxic, physiologically acceptable and metabolizable lipid capable of forming liposomes can be used. The present compositions of the invention in liposome form can contain stabilizers, preservatives, excipients, and the like in addition to the agent. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Also within the scope of the invention is the use of a phytase of the invention during the preparation of food or feed preparations or additives, e.g., dietary additives or dietary aids. For example, in one aspect, the phytase exerts its phytase activity during the manufacture only and is not active in the final food or feed product. This aspect is relevant for instance in dough making and baking. Accordingly, phytase or recombinant yeast expressing phytase can be impregnated in, on or through magnetic carriers, distributed in the dough or food medium, and retrieved by magnets.

The dietary aid of the invention may be administered alone to animals in a biocompatible (e.g., a biodegradable or non-biodegradable) carrier or in combination with other digestion additive agents. The dietary aid of the invention thereof can be readily administered as a top dressing or by mixing them directly into animal feed or provided separate from the feed, by separate oral dosage, by injection or by transdermal means or in combination with other growth related edible compounds, the proportions of each of the compounds in the combination being dependent upon the particular organism or problem being addressed and the degree of response desired. It should be understood that the specific dietary dosage administered in any given case will be adjusted in accordance with the specific compounds being administered, the problem to be treated, the condition of the subject and the other relevant facts that may modify the activity of the effective ingredient or the response of the subject, as is well known by those skilled in the art. In general, either a single daily dose or divided daily dosages may be employed, as is well known in the art.

If administered separately from the animal feed, forms of the dietary aid can be prepared by combining them with non-toxic pharmaceutically acceptable edible carriers to make either immediate release or slow release formulations, as is well known in the art. Such edible carriers may be either solid or liquid such as, for example, corn starch, lactose, sucrose, soy flakes, peanut oil, olive oil, sesame oil and propylene glycol. If a solid carrier is used the dosage form of the compounds may be tablets, capsules, powders, troches or lozenges or top dressing as micro-dispersable forms. If a liquid carrier is used, soft gelatin capsules, or syrup or liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

Thus, significant advantages of the invention can include for example, 1) ease of manufacture of the active ingredient loaded biocompatible compositions; 2) versatility as it relates to the class of polymers and/or active ingredients which may be utilized; 3) higher yields and loading efficiencies; and 4) the provision of sustained release formulations that release active, intact active agents in vivo, thus providing for controlled release of an active agent over an extended period of time. In addition, another advantage is due to the local delivery of the agent with in the digestive tract (e.g., the gizzard) of the organism. As used herein the phrase "contained within" denotes a method for formulating an agent into a composition useful for controlled release, over an extended period of time.

In the sustained-release or slow release compositions of the invention, an effective amount of an agent (e.g., an enzyme or antibiotic) will be utilized. As used herein, sustained release or slow release refers to the gradual release of an agent from a biocompatible material, over an extended period of time. The sustained release can be continuous or discontinuous, linear or non-linear, and this can be accomplished using one or more biodegradable or non-biodegradable compositions, drug loadings, selection of excipients, or other modifications. However, it is to be recognized that it may be desirable to provide for a "fast" release composition, that provides for rapid release once consumed by the organism. It is also to be understood that "release" does not necessarily mean that the agent is released from the biocompatible carrier. Rather in one embodiment, the slow release encompasses slow activation or continual activation of an agent present on the biocompatible composition. For example, a phytase need not be released from the biocompatible composition to be effective. In this embodiment, the phytase is immobilized on the biocompatible composition.

The animal feed may be any protein-containing organic meal normally employed to meet the dietary requirements of animals. Many of such protein-containing meals are typically primarily composed of corn, soybean meal or a corn/soybean meal mix. For example, typical commercially available products fed to fowl include Egg Maker Complete, a poultry feed product of Land O'Lakes AG Services, as well as Country Game & Turkey Grower a product of Agway, Inc. (see also The Emu Farmer's Handbook by Phillip Minnaar and Maria Minnaar). Both of these commercially available products are typical examples of animal feeds with which the present dietary aid and/or the enzyme phytase may be incorporated to reduce or eliminate the amount of supplemental phosphorus, zinc, manganese and iron intake required in such compositions.

The present invention is applicable to the diet of numerous animals, which herein is defined as including mammals (including humans), fowl and fish. In particular, the diet may be employed with commercially significant mammals such as pigs, cattle, sheep, goats, laboratory rodents (rats, mice, hamsters and gerbils), fur-bearing animals such as mink and fox, and zoo animals such as monkeys and apes, as well as domestic mammals such as cats and dogs. Typical commercially significant avian species include chickens, turkeys, ducks, geese, pheasants, emu, ostrich, loons, kiwi, doves, parrots, cockatiel, cockatoo, canaries, penguins, flamingoes, and quail. Commercially farmed fish such as trout would also benefit from the dietary aids disclosed herein. Other fish that can benefit include, for example, fish (especially in an aquarium or acquaculture environment, e.g., tropical fish), goldfish and other ornamental carp, catfish, trout, salmon, shark, ray, flounder, sole, tilapia, medaka, guppy, molly, platyfish, swordtail, zebrafish, and loach.

Unless otherwise stated, transformation was performed as described in the method of Sambrook, Fritsch and Maniatus, 1989.

Human and Animal Dietary Supplements

The invention provides novel dietary formulation, supplements and additives for humans and animals and methods for diet supplementation comprising phytases, e.g., a phytase of the invention (e.g., a phytase having a sequence identity of at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97.5%, 98%, 98.5%, 99%, 99.5%, or more, or complete (100%) sequence identity (i.e., homology) to SEQ ID NO:2 (a phytase polypeptide); SEQ ID NO:10 (a phytase polypeptide); a polypeptide having sequence as set forth in SEQ ID NO:8 and having at least one, or all, of the amino acid modifications W68E, Q84W, A95P, K97C, S168E, R181Y, N226C, Y277D, wherein the polypeptide has phytase activity) or other phytases, for example, the E. coli appA "wild type" phytase-encoding SEQ ID NO:7, or, a polypeptide sequence of SEQ ID NO:2 or the E. coli appA "wild type" phytase SEQ ID NO:8.

For example, the invention provides novel formulations and dietary supplements and additives, and methods for diet supplementation for certain diets, e.g., Atkins' diet, vegetarian diet, macrobiotic diet, vegan diet or regional diets, e.g., developing world diets. Foods associated with certain elective diets, such as Atkins, vegetarian, macrobiotic, vegan or regional diets (for example, developing world diets) emphasize certain food categories, such as proteins and fats, soy, etc., or they rely on indigenous crops, e.g., cereals, rice, beans, and the like as substantial or sole contributors to individual nutrition. Many of these cereal based crops have elevated (3 to 10 fold) levels of phytic acid. Processed food products such as soy protein hydrolysate and others appear to retain elevated levels of phytic acid and their inclusion as a protein source to nutrient bars, powders and other foods or food supplements and ingredients increases the phytic acid load experienced by individuals who practice these diets.

Preventing and Reversing Bone Loss

The invention also provides novel pharmaceutical and dietary formulations to be used as supplements and additives, and methods for dietary supplementation, comprising phytases, e.g., any phytase, including a phytase of the invention, for individuals predisposed to bone loss, individuals with bone loss, and individuals with certain medical conditions, e.g., osteoporosis, cachexia, and medical treatments, such as chemotherapies, which can compromise the proper uptake or utilization of essential nutrients. The methods and compositions of the invention can be used alone or in combination with other supplements or treatment regimens, including with medications and the like. For example, the formulations, dietary supplements and methods for diet supplementation can be administered with other dietary supplements or medications for the treatment or prevention of osteoporosis, e.g., with vitamin D3 and/or calcium (which are proven in preventing bone loss). In one aspect, the invention provides a formulation comprising a phytase, e.g., any phytase or a phytase of the invention, and vitamin D3 and/or calcium. In one aspect, the invention provides a formulation comprising a phytase, e.g., any phytase or a phytase of the invention, for preventing bone loss. In one aspect, the invention provides a formulation comprising a phytase, e.g., any phytase or a phytase of the invention, for reversing bone loss.

The formulation can be in the form of a pharmaceutical composition, or, can be an additive to a pharmaceutical, either of which can be in liquid, solid, powder, lotion, spray or aerosol forms. Pharmaceutical compositions and formulations of the invention for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

The invention provides aqueous suspensions comprising a phytase, e.g., a phytase of the invention, in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol monooleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest edition of Remington, *The Science and Practice of Pharmacy* $20^{th}$ Ed. Lippincott Williams & Wilkins). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention (e.g., reversing bone loss, or, preventing bone loss) are appropriate and correct.

Physical Training Supplements

The invention also provides novel dietary supplements and additives, and methods of using them, comprising phytases, e.g., any phytase, or, a phytase of the invention, for individuals undergoing athletic or other intense physical training, e.g., training for soldiers. Athletic training and hyperexertion can deplete essential nutrients and require dietary supplementation. These diets and conditions have in common a lack of essential micronutrients such as metals (K, Ca, Fe, Zn, Mn, Se) and ions ($PO_4$) necessary for optimal nutrition. Diets rich in phytic acid exacerbate this problem and may also lead to both chronic and acute conditions that result from either voluntary or economically enforced dependence on diets rich in high phytic acid foods.

For example, individuals following various low carbohydrate ("low carb") diets are often plagued with muscle, e.g., leg muscle, cramps. Typical advice for this is to add additional potassium, calcium and other nutrients to their diet. This invention provides compositions for dietary supplementation, dietary aids and supplements and methods for diet supplementation to enhance otherwise compromised nutrition via the mobilization of macro and micronutrients using phytase supplementation to the diet (including use of any phytase, or, a phytase of the invention).

In one aspect of the invention, the use of a phytase (e.g., use of any phytase, or, a phytase of the invention) is optimized to demonstrate thermolabile or pH-stability profiles that will make it suitable for addition directly to the food and supplement process and/or demonstrate enhanced stability and activity in the human or animal gastro intestinal tract.

The invention also provides novel dietary supplements and additives, and methods of using them, comprising phytases, e.g., any phytase, or, a phytase of the invention, for individuals undergoing mineral supplementation. Mineral supplementation for people on foods with high phytic acid content may actually exacerbate problems with nutrient availability.

Literature references suggest that complexes of phytic acid, calcium and zinc are much more insoluble that complexes of phytic acid and calcium. People often take multi mineral supplements. The addition of phytase to a scheme devised to combine mineral supplements in the presence of high phytic acid foods could make these supplements much more effective.

In alternative aspects, the compositions and methods of the invention (comprising any phytase, or, a phytase of the invention) are used as supplements or additives to Weight-loss programs which limit intake of particular food groups, vegetarian, macrobiotic or vegan diets which limit or preclude intake of meats, nightshade vegetables, breads, etc and other diets which focus on intake of nuts, Specific supplement for individuals on low carb diets rich in high phytic acid foods to ease physiological symptoms based on reduced mineral uptake, Athletic training regimens which seek to enhance performance through dietary intake, including military training regimens, Hospital diets tailored to specific needs of patients compromised in uptake or restricted to food groups Micronutrient-poor cereal and legume diets in the developing world, School lunch programs.

The invention also provides kits comprising compositions of the invention (comprising any phytase, or, a phytase of the invention) and instructions on incorporating the composition or method of the invention into these diets. The kits can comprise any packaging, labeling, product inserts and the like.

In one aspect, the invention provides a natural phytase or an optimized phytase of the invention, formulated for or optimized for (e.g., sequence optimized for) production, processing or passage thru human or animal system, e.g., digestive tract. The phytase enzyme can be optimized using alternative formulations.

Alternatively, a phytase enzyme of the invention, or, any phytase, can be optimized by engineering of its sequence, e.g., using for example, directed evolution, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, ligation reassembly, GSSM™ and any combination thereof, to retain activity during processing, ingestion and in the human gut.

The compositions (e.g., dietary formulations comprising any phytase enzyme, or a phytase enzyme of the invention) can be delivered in a number of ways to provide dietary efficacy. For example, the invention provides compositions (e.g., dietary formulations or additives comprising any phytase enzyme, or a phytase enzyme of the invention) and methods comprising use of:

In packaged food supplements such as chewable tablets or nutritional bars,

As a lyophilized product available for hydration prior to ingestion,

Co-packaged with dietary products, eg., processed soy product or sold as a formulation with soybean protein hydrolysate and other processing fractions from whole foods that are sold as ingredients to the processed food industry, In commercial baked goods, Spray-on to breakfast cereals, Spray-administered (e.g., nasal spray) formulations, As a transgenic product expressed in indigenous crops, ie., cereals and legumes (e.g., as a transgenic product of a microorganism, such as a bacterium)

As a transgenic organism, e.g., a microorganism; for example, a human or animal is fed a bacteria or other microorganism capable of making (and, in an alternative embodiment, secreting) a recombinant phytase, such as a phytase of the invention, after ingestion or implantation, e.g., into the gut of the human or animal.

Phytase-containing products and methods of the invention can be branded as nutrient enhanced, nutrient compatible or otherwise noted for an ability to enhance nutrient performance and relieve various symptoms associated with nutrient deficiency.

Phytase-containing products and methods of the invention are used to mitigate the anti-nutritive effects of phytate, which chelates important dietary minerals such as zinc, copper, iron, magnesium, tin, and calcium. According, phytase-containing products and methods of the invention are used as dietary supplements to prevent the precipitation of metal-binding enzymes and proteins in ingested foods. In one aspect, the phytase-containing products and methods of the invention are used to mitigate the anti-nutritive effects of phytate in human diets, in particular those rich in legumes and cereals, to increase mineral bioavailability. In one aspect, a phytase in a dietary supplement of the invention catalyzes the partial or complete hydrolytic removal of orthophosphate from a phytate, where complete hydrolysis of phytate results in the production of 1 molecule of inositol and 6 molecules of inorganic phosphate.

Phytase-containing products and methods of the invention are applicable to the diet of humans and numerous animals, including fowl and fish. For example, phytase-containing dietary supplement products and dietary supplement methods of the invention can be practiced with commercially significant species, e.g., pigs, cattle, sheep, goats, laboratory rodents (rats, mice, hamsters and gerbils), fur-bearing animals such as mink and fox, and zoo animals such as monkeys and apes, as well as domestic mammals such as cats and dogs. Typical commercially significant avian species include chickens, turkeys, ducks, geese, pheasants, emu, ostrich, loons, kiwi, doves, parrots, cockatiel, cockatoo, canaries, penguins, flamingoes, and quail. Commercially farmed fish such as trout would also benefit from the dietary aids disclosed herein. Other fish that can benefit include, for example, fish (especially in an aquarium or aquaculture environment, e.g., tropical fish), goldfish and other ornamental carp, catfish, trout, salmon, shark, ray, flounder, sole, tilapia, medaka, guppy, molly, platyfish, swordtail, zebrafish, and loach.

Phytase-containing products and methods of the invention are also used in various agars, gels, medias, and solutions used in tissue and/or cell culturing. Inconsistent soy hydrolysates can be a problem encountered when using tissue and/or cell culturing. In one aspect, phytase-containing products and methods of the invention are used as cell culture media additives or as treatments to, e.g., increase cell culture yield and performance consistency. In one aspect, the invention provides hydrolysate for cell culturing comprising phytases, e.g., phytases of the invention.

In one aspect, to provide a consistent product, the invention provide methods for making hydrolysates, supplements or other additives for cell culturing comprising phytases by using phytase biomarkers. For example, the method would comprise "scoring" or "marking" several molecules of phytase in batches of hydrolysate, supplement or other additive, and then blending the batches in the hydrolysate, supplement or other additive to achieve a consistent biomarker pattern. In one aspect, culture performance with each batch is measured in a mini-bioreactor(s) and performance with each biomarker and batch is correlated. In one aspect, a blend is made to generate a higher performance product that is consistent or better than average. In one aspect, thioredoxin (TRX) is added to increase the bioavailability of many proteins by eliminating secondary structure caused by disulfide bonds. In one aspect, proteases are also added to the hydrolysates, supplements or additives of the invention. The proteases can be "scored" or quality controlled with other biomarkers (as with phytase, as discussed above) to direct the blending process.

In one aspect, the invention provides methods for adding phytases to grains to provide a consistent product using a biomarker "scoring" or quality control process analogous to that described above for the hydrolysates, supplements or additives of the invention.

Enzyme Enhanced Diets for Increased Warfighter Efficiency and Morale

In one aspect, the invention provides novel dietary supplements and additives and methods for diet supplementation comprising phytases, e.g., any phytase, or, a phytase of the invention, for enzyme-enhanced diets for increased warfighter efficiency and morale. In one aspect, these dietary supplement compositions of the invention work, in situ, to enhance energy, stamina and morale in a stable, easily usable and desirable format while limiting food waste.

In one aspect, these dietary supplement compositions and methods of the invention address the military operational challenge comprising efficient delivery of nutrients and the associated health, morale and operational effectiveness of soldiers. The invention provides enzymes optimized to function efficiently in the human gut. These enzymes can enhance extraction of nutrients and generation of energy as well as prolong maintenance of nutritional sufficiency and individual satiety.

In addition to phytase, other enzymes, e.g., amylases, xylanases, proteases, lipases, are used to practice the dietary supplement compositions and methods of the invention. In one aspect, the invention provides formulations, food supplements, foods, self-contained meal Ready-to-Eat units (MREs), drinks, hydrating agents and the like, comprising phytase, e.g., a phytase of the invention, and another enzyme, e.g., amylases, xylanases, proteases, lipases or a combination thereof. When ingested with food, these enzymes have been shown to enhance the release of critical nutrients, e.g., phosphorus, essential metals and ions, amino acids, and sugars. Furthermore, co-ingestion of these enzymes increases gastrointestinal mechanics and absorption by depolymerizing plant-derived cellulose, hemicellulose and starch. This white paper proposes the development of these enzymes as supplements to military diets to provide enhanced nutrient utilization for warfighter.

In one aspect, the food supplement of the invention causes the release of essential phosphate from normally anti-nutritive, plant-derived phytate to increase food energy yield and bone $CaPO_4$ deposition. In one aspect, phytases and other potential nutritional supplement enzymes can withstand gut pH and endogenous protease activities.

In one aspect, the invention provides enzyme supplements to rations, drinks, foods, MREs, hydrating agents and the like to significantly improve nutritional value, digestibility and energy content of military meals (or any meal, including general consumer meal and diet supplementation products) served to warfighters in training, battle or any stressful situation. The supplement can be formulated for ease of use and personal transport (in or with MREs, hydrating agents, etc).

In one aspect, the enzyme supplement will not compromise food appearance, taste and/or consistency. In one aspect, the product improve health and increases the stamina of warfighters.

In alternative aspects, the enzyme supplement is delivered in a number of ways to provide dietary efficacy; for example, the invention provides phytases, including phytases of the invention, and in some aspects, additional enzymes, in:

Packaged food or drink supplements such as MREs, rations, survival kits, hydrating agents, chewable tablets or nutritional bars;

As a lyophilized product (e.g., a powder) available for hydration prior to ingestion;

Co-packaged with dietary products, foods, drinks, e.g., processed soy product or a formulation with soybean protein hydrolysate and other processing fractions from whole foods that are sold as ingredients to the processed food industry;

In baked goods;

Spray-on to cereals;

Formulations such as tablets, geltabs, capsules, sprays and the like.

In one aspect, the compositions and methods of the invention provide nutritional supplementation that rapidly releases calories and macro- and micronutrients from ingested meals. In one aspect, the compositions and methods of the invention provides energy and body strength to individuals in stressful situations, e.g., involving hyperexertion and discontinuous periods of depravation. In one aspect, the compositions and methods of the invention provide enzymes optimized and formulated to work effectively in human gut while maintaining stability, shelf life and transportability in a desired environment, e.g., a military setting.

In one aspect, the compositions and methods of the invention provide formulations for increased taste characteristics, dissolvability, chewability and personal transport efficiency of the product. In one aspect, the compositions and methods of the invention further comprise other components, such as potassium, glucose, $CaCl_2$. $CaCl_2$ in the formulation can combine with released phosphate and, in turn, enhance bone deposition and weight gain. In one aspect, the compositions and methods of the invention further comprise formulations of other enzymes, such as proteases, cellulases, hemicellulases, for protein, cellulose and hemicellulose digestion, respectively. These enzymes can improve protein and starch availability and further increase iron absorption from many iron-rich foods.

In one aspect, the compositions and methods of the invention further comprise enzymes for hydrolyzing foods derived from plant material, which is rich in the glucose and xylose-based polymers, cellulose, hemicellulose and starch, as well as in the amino acid polymer, protein. In one aspect, the compositions and, methods of the invention facilitate hydrolysis of polymeric materials in foods; i.e., to facilitate complete digestion polymers to monomers, e.g., polysaccharides to monomeric sugars, or proteins to amino acid moieties. Thus, in this aspect, the compositions and methods of the invention allow a food, drink or ration to realize its full caloric and nutritional value. In one aspect, enzyme supplementation comprises use of stabile enzymes, e.g., hydrolases of various kinds, cellulases, hemicellulases, amylases, lipases, amidases, proteases and other enzymes. In one aspect, enzymes used in the compositions and methods of the invention can withstand ambient gut conditions, i.e., stability at low pH and in the presence of gastric proteases.

Industrial Uses of Phytases

In addition to those described above, the invention provides novel industrial uses for phytases, inlcuding use of the novel phytases of the invention.

In one aspect, the invention provides compositions comprising phytases (including the phytases of the invention) for addition to waste or manure piles to convert "environmental" phytic acid. In one aspect, this serves the purposes of reducing pollution and increasing nutrient availability. The invention also provides compositions and methods for adding a phytase to soil, natural or artificial bodies of water (e.g., lakes, ponds, wells, manure ponds, and the like), municipal sewage, any sewage effluent, and the like. As described above, the invention provides compositions and methods for reducing phytate levels in waste or sewage, e.g., an animal manure, wherein the animal is fed a dietary aid containing an effective amount of a phytase, e.g., a phytase of the invention. An exemplary application of the compositions and methods of the invention is to reduce the phosphate pollution in the environment. Thus, the compositions and methods of the invention can be used in any application that reduces pollution by degrading phytic acids.

In one aspect, the invention provides compositions comprising phytases (including the phytases of the invention) and methods for farming applications or other plant growth applications, e.g., adding phytases to fertilizers or plant food additives (e.g., MIRACLEGROW™) for plants, e.g., house plants. In using the compositions and methods of the invention for farming applications, users include organic farmers. The compositions and methods of the invention can be used for adding phytases to any soil deficient in phosphorous or needing supplementary phosphorous for a particular crop or application. Because phosphorous release helps plants grow, compositions and methods of the invention can be used for adding phytases to anything that has algae or plant material in it.

In one aspect, the invention provides compositions comprising phytases (including the phytases of the invention) and methods for cosmetic applications, e.g., shampoos, lotions or soaps containing plant products.

In one aspect, the invention provides compositions comprising phytases (including the phytases of the invention) and methods for immobilizing the phytase. In one aspect, the immobilized phytase acts as a controlled release mechanism. For example, in one aspect, the invention provides control released (time release) formulations of phytases for application to soil, e.g., clay, to house plants, etc. In one aspect, the phytases are immobilized to beads, e.g., polysorb beads. These beads can be delivered to soil, e.g., for agricultural or house plants. In another aspect, control released (time release) formulations of phytases of the invention are used in dietary supplements and additives.

The invention will be further described with reference to the following examples; however, it is to be understood that the invention is not limited to such examples. While the procedures described in the examples are typical of those that can be used to carry out certain aspects of the invention, other procedures known to those skilled in the art can also be used.

EXAMPLES

Example 1

Isolation, Bacterial Expression, and Purification of Phytase

*E. coli* B genomic DNA was obtained from Sigma (Catalog # D-2001), St. Louis, N.J.

The following primers were used to PCR amplify the gene directly from the genomic DNA:

5' primer gtttctgaattcaaggaggaatttaaAT-GAAAGCGATCTTAATCCCATT (SEQ ID NO:3); and

3' primer gtttctggatccTTACAAACTGCACGCCGGTAT (SEQ ID NO:4).

Pfu polymerase in the PCR reaction, and amplification was performed according to manufacturers protocol (Stratagene Cloning Systems, Inc., La Jolla, Calif.).

PCR product was purified and purified product and pQE60 vector (Qiagen) were both digested with EcoRI and BglII restriction endonucleases (New England Biolabs) according to manufacturers protocols. Overnight ligations were performed using standard protocols to yield pQE60.

The amplified sequences were inserted in frame with the sequence encoding for the RBS. The ligation mixture was then used to transform the *E. coli* strain M15/pREP4 (Qiagen, Inc.) by electroporation. M 15/pREP4 contains multiple copies of the plasmid pREP4, which expresses the lacI repressor and also confers kanamycin resistance (Kan$^r$). Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation.

The primer sequences set out above may also be employed to isolate the target gene from the deposited material by hybridization techniques described above.

This invention also provides for the isolation and use of phytase molecules (nucleic acids and phytase enzymes encoded thereby) from all other strains of *E. coli* (whether virulent or non-virulent, including K12, W, C), as well as all bacteria. These include all known species and strains belonging to:

Thermotogales

Green Nonsulfur Bacteria

Cyanobacteria & chloroplasts

Low G+C Gram-Positive Bacteria

Fusobacteria

High G+C Gram-Positive Bacteria

Gytophaga/Flexibacter/*Bacteroides* group

Fibrobacteria

Spriochaetes

Planctomyces/*Chlamydia* group

Purple bacteria (Proteobacteria), including the following subdivisions:

Delta & Epsilon, including:
  Desulfuromonas acetoxidans
  Desulfosarcina variabilis
  Bdellovibrio stolpii
  Nannocystis exedens
  Stigmatella aurantiaca
  Myxococcus xanthus
  Desulfovibrio desulfuricans
  Thiovulum sp.
  Campylobacter jejuni
  Wolinella succinogenes
  Helicobacter pylori
Alpha, including:
  Methylobacterium extorquens
  Beijerinckia indica
  Hyphomicrobium vulgare
  Rhodomicrobium vannieli
  Agrobacterium tumefaciens
  Brucella abortus
  Rochalimaea quintana
  Rhodopseudomonas marina subsp. agilis
  Zea mays-mitochondrion
  Rickettsia rickettsii
  Ehrlichia risticii
  Wolbachia pipientis
  Anaplasma marginale
  Erythrobacter longus
  Rhodospirillum salexigens
  Rhodobacter capsulatus
  Azospirillum lipoferum
  Rhodospirillum rubrum
Gamma, including:
  Ectothiorhodospira shaposhnikovii
  Chromatium vinosum
  Methylomonas methanica
  Cardiobacterium hominis
  Xanthomonas maltophilia
  Coxiella burnetii
  Legionella pneumophila subsp. pneumophila
  Oceanospirillum linum
  Acinetobacter calcoaceticus
  Pseudomonas aeruginosa
  Haemophilus influenzae
  Vibrio parahaemolyticus
  Proteus vulgaris
  Erwinia carotovora
  Escherichia coli, including:
Beta, including:
  Eikenella corrodens
  Neisseria gonorrhoeae
  Vitreoscilla stercoraria
  Chromobacterium violaceum
  Alcaligenes faecalis
  Rubrivivax gelatinosus
  Pseudomonas testosteroni
  Nitrosomonas europae
  Spirillum volutans Substances that alter the digestive flora environment of the consuming organism to enhance growth rates. As such, there are many problematic burdens—related to nutrition, ex vivo processing steps, health and medicine, environmental conservation. Such phytase molecules can be isolated from these bacteria by know methods, including library screening methods, e.g. expression screening, hybridization methods, PCR (e.g. see Sammbrook, 1989).

Example 2

Thermal Tolerance Assay

Figure 3:
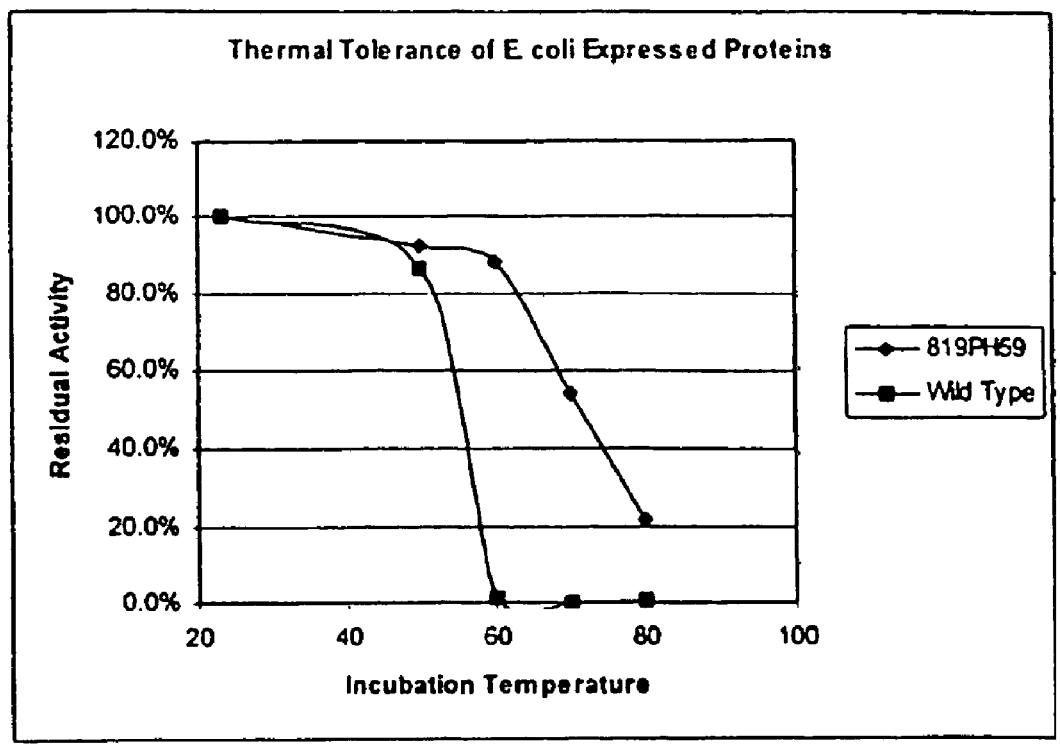
FIG. 3 shows a graph with the results of a thermal tolerance assay between SEQ ID NO:8 (*E. coli* appA wild type) and an exemplary phytase of the invention having a sequence as set forth in SEQ ID NO:10 (modified phytase).

The wild type appA from *E. coli* (strain K12) and a mutagenized version designated 819PH59 (SEQ ID NO:9 and 10) were expressed in *E. coli* and purified to homogeneity. In the thermal tolerance assay, 100 uL of 0.01 mg/mL of protein in 100 mM MOPS/pH 7.0 was heated to the indicated incubation temperature for 5 minutes in an RJ research thermocycler. Upon completion of the 5 minutes at the incubation temperature, the samples were cooled to 4° C. and incubated on ice. An activity assay was run using 40 uL of the enzyme solution in 1.5 mL of 100 mM NaOAc/4 mM phytate/pH 4.5 at 37° C. Aliquots of 60 uL were withdrawn at 2 minute intervals and added to 60 uL of the color developer/Stop solution of the TNO assay. Clearly, the modified enzyme, SEQ ID NO:10, containing 8 amino acid changes, is tolerant to temperatures greater than the wild-type enzyme. See FIG. 3.

Example 3

Stability of Phytase Enzyme in Simulated Digestibility Conditions

Figure 4:
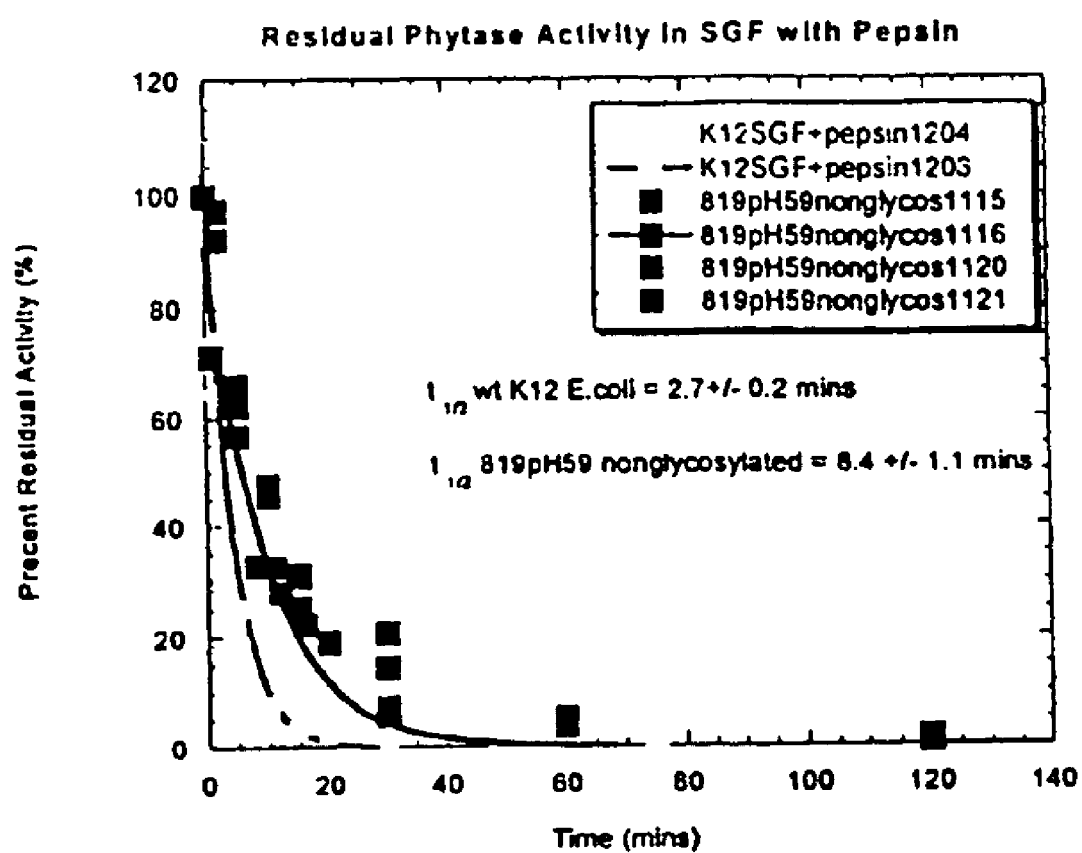
FIG. 4 shows a graph with the stability of phytase enzymes under simulated digestibility conditions.

The percent residual activities (based on initial rates) of the in vitro digested *E. coli* K12 and the nonglycosylated 819pH59 phytase were plotted verses time. A standard concentration of simulated gastric fluid containing 2 mg/ml NaCl, 6 M HCl and 3.2 mg/mL pepsin was prepared as described. The pH of the solution was about 1.4 and was not adjusted. The in vitro digestibility assay was performed by adding 1:4 (vol:vol) of phytase to digestion solution and immediately incubating at 37° C. to initiate the digestion reaction. Aliquots of the digestion reaction mixture were removed at various time intervals and assayed for residual phytase activity using the TNO assay. Each of the assays was performed at least twice. An exponential curve with the equation y=Ae-kt was fit to the data. The half lives of the proteins were determined using the equation t ½=ln 2/k. The half-life of the *E. coli* K12 phytase was only 2.7±0.2 minutes while the nonglycosylated 819pH59 phytase had a half-life of 8.4±1.1 minutes. Therefore, the mutations in the wildtype *E. coli* K12 phytase enhanced the stability of the enzyme under simulated in vitro digestibility conditions. See FIG. 4.

Example 4

Expression Host Comparisons

Figure 5:
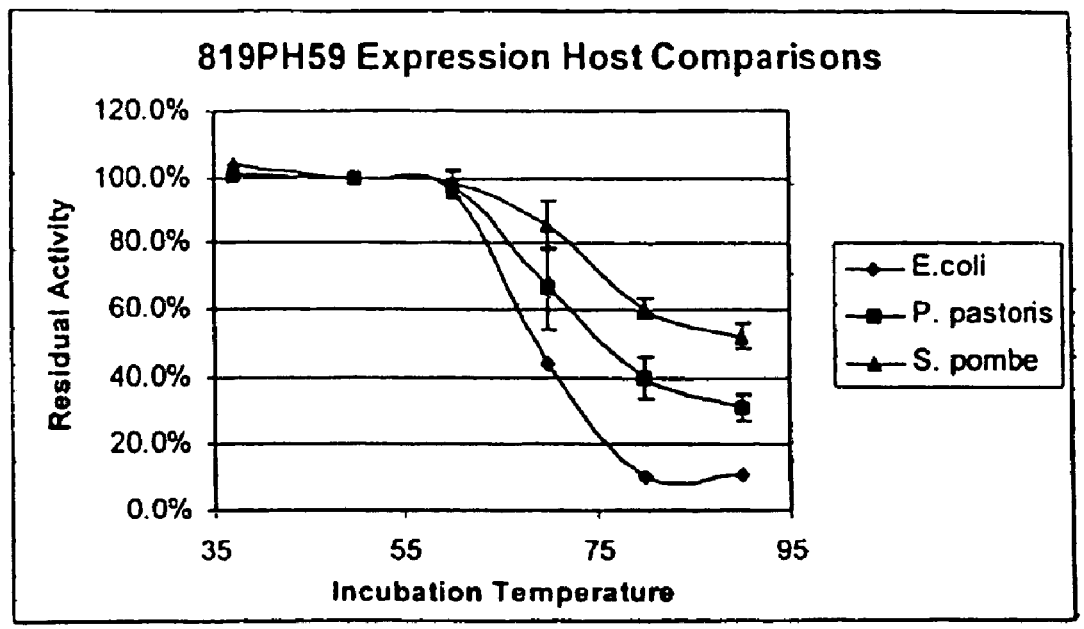
FIG. 5 shows a graph with expression of wild-type and modified phytase (SEQ ID NO:10) in various host cells.

The GSSM™ DNA construct from 819PH59 was inserted into *E. coli*, *P. pastoris*, and *S. pombe* for expression. The expressed proteins were purified to homogeneity. In the thermal tolerance assay, 100 uL of 0.01 mg/mL of protein in 100 mM MOPS, pH 7.0 was heated to the indicated incubation temperature for 5 minutes in an RJ research thermocycler. Upon completion of the 5 minutes at the incubation temperature, the samples were cooled to 4° C. and incubated on ice. An activity assay was run using 40 uL of the enzyme solution in 1.46 mL of 100 mM NaOAc/4 mM phytate/pH 4.5 at 37° C. Aliquots of 60 uL were withdrawn at 2 minute intervals and added to 60 uL of the color developer/Stop solution of the TNO assay. See FIG. 5.

Example 5

Figure 6:
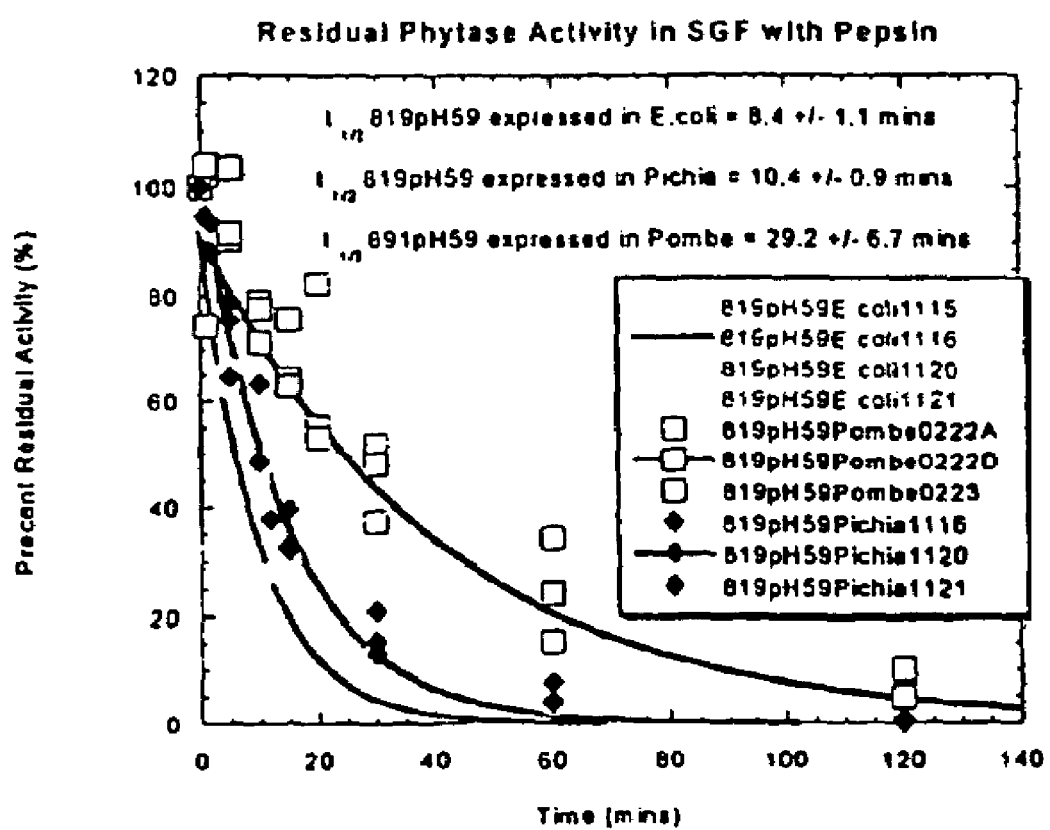
FIG. 6 shows a graph of residual phytase activity in SGF with pepsin.

The percent residual activities (based on initial rates) of the in vitro digested 819pH59 phytase expressed in various expression hosts were plotted verses time. The 819pH59 phytase was expressed in *E. coli* (nonglycosylated), as well as in *S. pombe* and *P. pastoris* (glycosylated). A standard concentration of simulated gastric fluid containing 2 mg/ml NaCl, 6 M HCl and 3.2 mg/mL pepsin was prepared as described in the S.O.P. The pH of the solution was about 1.4 and was not adjusted. The in vitro digestibility assay was performed by adding 1:4 (vol:vol) of phytase to digestion solution and immediately incubating at 37° C. to initiate the digestion reaction. Aliquots of the digestion reaction mixture were removed at various time intervals and assayed for residual phytase activity using the TNO assay. Each of the assays was performed in triplicate. An exponential curve with the equation $y=Ae^{-kt}$ was fit to the data. The half lives of the proteins were determined using the equation $t_{1/2}=\ln 2/k$. The half-life of the nonglycosylated 819pH59 phytase expressed in *E. coli* was 8.4±1.1 minutes while the glycosylated 819pH59 phytase expressed in *S. pombe* had a half-life of 10.4±0.9 minutes and the same phytase expressed in *P. pastoris* had a half-life of 29.2±6.7 mins. Therefore, the glycosylation of the 819pH59 phytase enhanced the stability of the enzyme under simulated in vitro digestibility conditions. See FIG. 6.

LITERATURE CITED (The teachings of all references cited in this application are hereby incorporated by reference in their entirety unless otherwise indicated.)

Association of Official Analytical Chemists: Official Methods of Analysis. Association of Official Analytical Chemists, Washington, D.C., 1970.

Ausubel F M, et al. Current Protocols in Molecular Biology. Greene Publishing Assoc., Media, PA. ©1987, ©1989, ©1992.

Barnes W M: PCR amplification of up to 35-kb DNA with high fidelity and high yield from lambda bacteriophage templates. *Proceedings of the National Academy of Sciences, USA* 91(6):2216-2220, 1994.

Bayer E A, Morag E, Lamed R: The cellulosome—a treasure-trove for biotechnology. *Trends Biotechnol* 12(9):379-86, (Sep) 1994.

Bevan M: Binary *Agrobacterium* vectors for plant transformation. *Nucleic Acids Research* 12(22):8711-21, 1984.

Bird et al. *Plant Mol Biol* 11:651, 1988.

Blobel G, Walter P, Chang C N, Goldman B M, Erickson A H, Lingappa V R: Translocation of proteins across membranes: the signal hypothesis and beyond. *Symp Soc Exp Biol* 33:9-36, 1979.

Brederode F T, Koper-Zawrthoff E C, Bol J F: Complete nucleotide sequence of alfalfa mosaic virus RNA 4. *Nucleic Acids Research* 8(10):2213-23, 1980.

Clark W G, Register J C 3d, Nejidat A, Eichholtz D A, Sanders P R, Fraley R T, Beachy R N: Tissue-specific expression of the TMV coat protein in transgenic tobacco plants affects the level of coat protein-mediated virus protection. *Virology* 179(2):640-7, (December) 1990.

Cole, et al.: Monoclonal Antibodies and Cancer Therapy. A. R. Liss, New York. ©1985.

Coligan J E, et al.: Current Protocols in Immunology. J. Wiley & Sons, New York. ©1996.

Coruzzi G, Broglie R, Edwards C, Chua N H: Tissue-specific and light-regulated expression of a pea nuclear gene encoding the small subunit of ribulose-1,5-bisphosphate carboxylase. *EMBO J.* 3(8):1671-9, 1984.

Cosgrove D J: Inositol phosphate phosphatases of microbiological origin. Inositol phosphate intermediates in the dephosphorylation of the hexaphosphates of myo-inositol, scyllo-inositol, and D-chiro-inositol by a bacterial (*Pseudomonas* sp.) phytase. *Aust J Biol Sci* 23(6):1207-1220, 1970.

Dassa E, Cahu M, Desjoyaux-Cherel B, Boquet P L: The acid phosphatase with optimum pH of 2.5 of *Escherichia coli*. Physiological and Biochemical study. *J Biol Chem* 257 (12):6669-76, (June 25) 1982.

Davis L G, et al. Basic Methods in Molecular Biology. Elsevier, New York, ©1986.

Duarte J C, Costa-Ferreira M: *Aspergilli* and lignocellulosics: enzymology and biotechnological applications. *FEMS Microbiol Rev* 13(2-3):377-86, (March) 1994.

Food Chemicals Codex, 4th Edition. Committee on Food Chemicals Codex, Food and Nutrition Board, Institute of Medicine, National Academy of Sciences. Published: National Academy Press, Washington, D.C.,) 1996.

Garcia P D, Ghrayeb J, Inouye M, Walter P: Wild type and mutant signal peptides of *Escherichia coli* outer membrane lipoprotein interact with equal efficiency with mammalian signal recognition particle. *J Biol Chem* 262(20):9463-8, (July 15) 1987.

Gluzman Y: SV40-transformed simian cells support the replication of early SV40 mutants. *Cell* 23(1):175-182, 1981.

Goeddel D V, Shepard H M, Yelverton E, Leung D, Crea R, Sloma A, Pestka S: Synthesis of human fibroblast interferon by *E. Coli*. *Nucleic Acids Research* 8(18):4057-4074, 1980.

Gordon-Kamm W J, Spencer T M, Mangano M L, Adams T R, Daines R J, Start W G, O'Brien J V, Chambers S A, Adams Jr. W R, Willets N G, Rice T B, Mackey C J, Krueger R W, Kausch A P, Lemaux P G. *Plant Cell* 2:603, 1990.

Graf E: Phytic Acid: Chemistry and Applications. Pilatus Press, Minneapolis. 1986.

Greiner R, Haller E, Konietzny U, Jany K D: Purification and characterization of a phytase from *Klebsiella terrigena*. *Arch Biochem Biophys* 341(2):201-6, (May 15) 1997.

Greiner R, Konietzny U: Construction of a bioreactor to produce special breakdown products of phytate. *J Biotechnol* 48(1-2):153-9, (July 18) 1996.

Greiner R, Konietzny U, Jany K D: Purification and characterization of two phytases from *Escherichia coli*. *Arch Biochem Biophys* 303(1):107-13, (May 15) 1993.

Guilley H, Dudley R K, Jonard G, Balazs E, Richards K E: Transcription of Cauliflower mosaic virus DNA: detection of promoter sequences, and characterization of transcripts. *Cell* 30(3):763-73, 1982.

Hespell R B, Whitehead T R: Physiology and genetics of xylan degradation by gastrointestinal tract bacteria. *J Dairy Sci* 73(10):3013-22, (Oct) 1990.

Hoekema A, Hirsch P R, Hooykaas P J J, Schilperoort R A. *Nature* 303:179, 1983.

Horsch R B, Fry J E, Hoffmann N L, Eichholtz D, Rogers S G, Fraley R T. *Science* 227:1229, 1985.

Igarashi M, Hollander VP: Acid phosphatase from rat liver. Purification, crystallization, and properties. *J Biol Chem* 243(23):6084-9, (Dec. 10) 1968.

International Union of Biochemistry and Molecular Biology, Nomenclature Committee: Enzyme nomenclature 1992: recommendations of the Nomenclature Committee of the International Union of Biochemistry and Molecular Biology on the nomenclature and classification of enzymes/ prepared for NC-IUBMB by Edwin C. Webb. Academic Press, ©1992.

Jeffries T W: Biochemistry and genetics of microbial xylanases. *Curr Opin Biotechnol* 7(3):337-42, (Jun.) 1996.

Klee H J, Muskopf Y M, Gasser CS: Cloning of an *Arabidopsis thaliana* gene encoding 5-enolpyruvylshikimate-3-phosphate synthase: sequence analysis and manipulation to obtain glyphosate-tolerant plants. *Mol Gen Genet* 210 (3):437-42, (Dec) 1987.

Kohler G, Milstein C: Continuous cultures of fused cells secreting antibody of predefined specificity. *Nature* 256 (5517):495-497, 1975.

Koster-Topfer M, Frommer WB, Rocha-Sosa M, Rosahl S, Schell J, Willmitzer L: A class II patatin promoter is under developmental control in both transgenic potato and tobacco plants. *Mol Gen Genet* 219(3):390-6, (Nov) 1989.

Kozbor. *Immunology Today* 4:72, 1983.

Lee B, Murdoch K, Topping J, Kreis M, Jones MG: Transient gene expression in aleurone protoplasts isolated from developing caryopses of barley and wheat. *Plant Mol Biol* 13(1):21-9, 1989.

National Research Council: Nutrient Requirements of Poultry (9th Revised ed.). National Academy Press, Washington, D.C., 1994.

Nayini N R, Markakis P: *Lebensmittel Wissenschaft und Technologie* 17:24-26, 1984.

NCBI, National Library of Medicine. National Institutes of Health: BLAST Sequence Similarity Searching.

Nelson T S, Shieh T R, Wodzinski R J, Ware J H: Effect of supplemental phytase on the utilization of phytate phosphorus by chicks. *J Nutr* 101 (10): 1289-1293, 1971.

Ng D T, Walter P: Protein translocation across the endoplasmic reticulum. *Curr Opin Cell Biol* 6(4):510-6, (Aug), 1994.

Potrykus I: Gene transfer methods for plants and cell cultures. *Ciba Found Symp* 154:198-208; discussion 208-12, 1990.

Powar V K, Jagannathan V: Purification and properties of phytate-specific phosphatase from *Bacillus subtilis*. *J Bacteriol* 151(3):1102-1108, 1982.

Powers T, Walter P: The nascent polypeptide-associated complex modulates interactions between the signal recognition particle and the ribosome. *Curr Biol* 6(3):331-8, (March 1), 1996.

Prade R A: Xylanases: from biology to biotechnology. *Biotechnol Genet Eng Rev;*13:101-31, 1996.

Ryan A J, Royal C L, Hutchinson J, Shaw C H: Genomic sequence of a 12S seed storage protein from oilseed rape (*Brassica napus* c.v. jet neuf). *Nucl Acids Res* 17(9):3584, 1989.

Saiki R K, Gelfand D H, Stoffel S, Scharf S J, Higuchi R, Horn G T, Mullis K B, Erlich H A: Primer-directed enzymatic amplification of DNA with a thermostable DNA polymerase. *Science* 239(4839):487-491, 1988.

Sambrook J, Fritsch E F, Maniatis T: Molecular Cloning: A Laboratory Manual, Cold Spring Habor Press, Cold Spring Habor, NY, ©1989.

SAS: Statistics In: SAS User's Guide (1984 ed.). SAS Institute, Carey, NC, 1984.

Schoner F J, Hope P P, Schwarz G, Wiesche H: Comparative effects of microbial phytase and inorganic phosphorus on performance and retention of phosphorus, calcium, and crude ash in broilers. *J Anim Physiol Anim Nutr* 66:248, 1991.

Schoner F J, Hope P P, Schwarz G, Wiesche H: Effects of microbial phytase and inorganic phosphate in broiler chicken: Performance and mineral retention at various calcium levels. *J Anim Physiol Anim Nutr* 69:235, 1993.

Shieh T R, Wodzinski R J, Ware J H: Regulation of the formation of acid phosphatases by inorganic phosphate in *Aspergillus ficuum*. *J Bacteriol* 100(3):1161-5, (Dec) 1969.

Shimamoto K, Miyazaki C, Hashimoto H, Izawa T, Itoh K, Terada R, Inagaki Y, Iida S: Trans-activation and stable integration of the maize transposable element Ds cotransfected with the Ac transposase gene in transgenic rice plants. *Mol Gen Genet* 239(3):354-60, (June) 1993.

Shimizu M: *Bioscience, Biotechnology, and Biochemistry* 56:1266-1269, 1992.

Sijmons P C, Dekker B M, Schrammeijer B, Verwoerd T C, van den Elzen P J, Hoekema A: Production of correctly processed human serum albumin in transgenic plants. *Biotechnology* (N Y) 8(3):217-21, 1990.

Simons P C, Versteegh H A, Jongbloed A W, Kemme P A, Slump P, Bos K D,. Wolters M G, Beudeker R F, Verschoor G J: Improvement of phosphorus availability by microbial phytase in broilers and pigs. *Br J Nutr* 64(2):525-540, 1990.

Smeekens S, Weisbeek P, Robinson C: Protein transport into and within chloroplasts. *Trends Biochem Sci* 15(2):73-6, 1990.

Smith A G, Gasser C S, Budelier K A, Fraley R T: Identification and characterization of stamen- and tapetum-specific genes from tomato. *Mol Gen Genet* 222(1):9-16, (June)1990.

Tague B W, Dickinson C D, Chrispeels M J: A short domain of the plant vacuolar protein phytohemagglutinin targets invertase to the yeast vacuole. *Plant Cell* 2(6):533-46, (June) 1990.

Tingey S V, Walker E L, Corruzzi G M: Glutamine synthetase genes of pea encode distinct polypeptides which are differentially expressed in leaves, roots and nodules. *EMBO J*. 6(1):1-9, 1987.

Ullah A H: Production, rapid purification and catalytic characterization of extracellular phytase from *Aspergillus ficuum*. *Prep Biochem* 18(4):443-458, 1988.

Ullah A H, Gibson DM: Extracellular phytase (E.C. 3.1.3.8) from *Aspergillus ficuum* NRRL 3135: purification and characterization. *Prep Biochem* 17(1):63-91, 1987

Van den Broeck G, Timko M P, Kausch A P, Cashmore A R, Van Montagu M, Herrera-Estrella L: Targeting of a foreign protein to chloroplasts by fusion to the transit peptide from the small subunit of ribulose 1,5-bisphosphate carboxylase. *Nature* 313(6001):358-63, 1985.

Vasil I K, Vasil V: Totipotency and embryogenesis in plant cell and tissue cultures. *In Vitro* 8(3):117-27, (November-December) 1972.

Vasil V, Vasil I K: Regeneration of tobacco and petunia plants from protoplasts and culture of corn protoplasts. *In Vitro* 10:83-96, (July-August) 1974.

Von Heijne G: Towards a comparative anatomy of N-terminal topogenic protein sequences. *J Mol Biol* 189(1):239-42, 1986.

*Walter P, Blobel G. *Biochem. Soc Symp* 47:183, 1986.

Wenzler H, Mignery G, Fisher L, Park W: Sucrose-regulated expression of a chimeric potato tuber gene in leaves of transgenic tobacco plants. *Plant Mol Biol* 13(4):347-54, 1989.

Wolter F P, Fritz CC, Willmitzer L, Schell J, Schreier P H rbcS genes in *Solanum tuberosum*: conservation of transit peptide and exon shuffling during evolution. *Proc Natl Acad Sci USA* 85(3):846-50, (Feb.) 1988.

Wong K K, Tan L U, Saddler J N: Multiplicity of beta-1,4-xylanase in microorganisms: functions and applications. *Microbiol Rev* 52(3):305-17, (Sept.) 1988.

Yamada K, et al.: *Agricultural and Biological Chemistry* 32:1275-1282, 1968.

U.S. Pat. No. 3,297,548; Filed Jul. 28, 1964; Issued Jan. 10, 1967. Ware J H, Bluff L, Shieh T K: Preparation of acid phytase.

U.S. Pat. No. 4,946,778; Filed Jan. 19, 1989; Issued Aug. 7, 1990. Ladner R C, Bird R E, Hardman K: Single polypeptide chain binding molecules.

EP0 120,516; Filed Feb. 21, 1984; Issued Oct. 3, 1984. Schilperoort R A, Hoekema A, Hooykaas R J J: A process of the incorporation of foreign DNA into the genome of dicotyledonous plants; *Agrobacterium tumefaciens* bacteria and a process for the production thereof; plants and plant cells with modified genetic properties; a process for the preparation.

EP0 321,004; Filed Oct. 28, 1988; Issued Jan. 22, 1992. Vaara T, Vaara M, Simell M, Lehmussaari A, Caransa A: A process for steeping cereals with a new enzyme preparation.

IPN WO 91/05053; Filed Sep. 27, 1990; Issued Apr. 18, 1991. VanGorcom R, et al.: Cloning and expression of microbial phytase.

Example 6

Figure 2B:
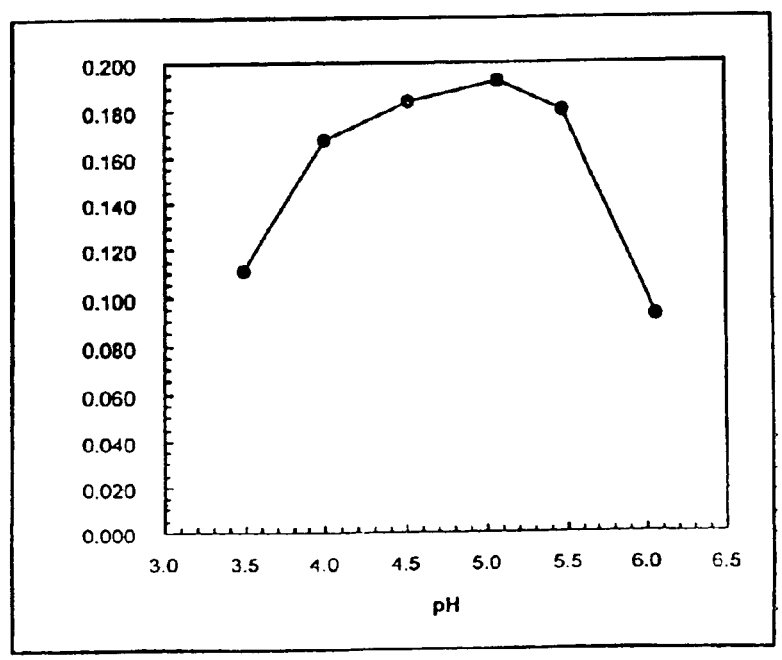

The following example describes an exemplary assay that can be used to determine if a polypeptide has phytase activity and is within the scope of the invention.

pH and temperature profile and stability data were measured for the exemplary phytase having a sequence as set forth in SEQ ID NO:2. FIGS. 2A and 2B show the pH and temperature profile and stability data, respectively, for an exemplary phytase enzyme of the present invention (having a sequence as set forth in SEQ ID NO:2). The assay used for these analyses is the following for the detection of phytase activity: Phytase activity is measured by incubating 10 μl of the enzyme preparation with 65 μl of 2 mM sodium phytate in 100 mM Tris maleate buffer pH 5.2, supplemented with 1 mM $CaCl_2$ for 30 minutes at 42° C. After incubation the reaction is stopped by adding 75 μl of 5% trichloroacetic acid. Phosphate released was measured against phosphate standard spectrophotometrically at 700 nm after adding 150 μl of the color reagent (4 volumes of 1.5% ammonium molybdate in 5.5% sulfuric acid and 1 volume of 2.7% ferrous sulfate; Shimizu, M., 1992; Biosci. Biotech. Biochem 56:1266-1269). OD at 700 nm is indicated on the Y-axis of the graphs in FIG. 2. Temperature or pH is indicated on the X-axis of the graphs.

Example 7

The following example describes an exemplary assay that can be used to determine if a polypeptide has phytase activity and is within the scope of the invention. This exemplary assay, also described by Engelen (1994) J. of AOAC International 77(3):760-764 (see also Nagashima (1999) Appl Environ Microbiol. 65(10):4682-4684), can be used as a simple and rapid determination as to whether a polypeptide has phytase activity under acidic conditions, e.g., at pH 5.5. The method is based on the determination of inorganic orthophosphate released on hydrolysis of sodium phytate at pH 5.5.

Weighed samples were diluted in duplicate with buffer (adjusted to pH 5.5 with acetic acid) and placed in waterbath at 37° C. Substrate solution (sodium phytate from rice adjusted to pH 5.5) added, samples mixed, and at 65 minutes incubation terminated with color-stop mix (ammonium heptamolybdate and ammonium vanadate). Tubes with sample centrifuged for 5 min. and absorbance measured at 415 nm with spectrophotometer. Corrected absorbance difference calculated by subtracting absorbance blank from that of corresponding sample. Enzyme activity is expressed in activity units (FTU), where 1 FTU is the amount of enzyme that liberates 1 umol inorganic orthophosphate per min under the test conditions (pH 5.5, 37° C.) See Engelen (1994) supra.

Numerous modifications and variations of the present invention are possible in light of the above teachings and, therefore, within the scope of the appended claims, the invention may be practiced otherwise than as particularly described. It is to be understood that, while the invention has been described with reference to the above detailed description, the foregoing description is intended to illustrate, but not to limit, the scope of the invention. Other aspects, advantages, and modifications of the invention are within the scope of the following claims. All publications, patent applications, patents, and other references mentioned herein are incorporated by reference in their entirety.

Although the invention has been described with reference to the presently preferred embodiments, it should be understood that various modifications can be made without departing from the spirit of the invention. Accordingly, the invention is limited only by the following claims.

---

What is claimed is:

1. A formulation comprising:
   (A) a polypeptide having phytase activity wherein the polypeptide is encoded by a nucleic acid comprising a variant of the nucleic acid of SEQ ID NO:7, wherein said variant has a nucleotide sequence which differs from SEQ ID NO:7 solely by:
       (i) substituting nucleotide 389 with G, substituting nucleotide 390 with A, substituting nucleotide 437 with T, substituting nucleotide 438 with G, substituting nucleotide 439 with G, substituting nucleotide 470 with C, substituting nucleotide 472 with T, substituting nucleotide 476 with T, substituting nucleotide 477 with G, substituting nucleotide 478 with T, substituting nucleotide 689 with G, substituting nucleotide 690 with A, substituting nucleotide 691 with G, substituting nucleotide 728 with T, substituting nucleotide 729 with A, substituting nucleotide 730 with T, substituting nucleotide 863 with T, substituting 864 with G, substituting nucleotide 1016 with G, or any combination thereof; or
       (ii) substituting nucleotide 389 with G, substituting nucleotide 390 with A, substituting nucleotide 437 with T, substituting nucleotide 438 with G, substituting nucleotide 439 with G, substituting nucleotide 470 with C, substituting nucleotide 472 with T, substituting nucleotide 476 with T, substituting nucleotide 477 with G, substituting nucleotide 478 with T, substituting nucleotide 689 with G, substituting nucleotide 690 with A, substituting nucleotide 691 with G, substituting nucleotide 728 with T, substituting nucleotide 729 with A, substituting nucleotide 730 with T, substituting nucleotide 863 with T, substituting 864 with G, and substituting nucleotide 1016 with G;
   (B) a polypeptide having phrase activity wherein said polypeptide comprises an amino acid sequence which is a variant of SEQ ID NO:8, wherein said variant differs from SEQ ID NO:8 solely by:
       (i) substituting amino acid 68 with E, substituting amino acid 84 with W, substituting amino acid 95 with P, substituting amino acid 97 with C, substituting amino acid 168 with E, substituting amino acid 181 with Y, substituting amino acid 226 with C, substituting amino acid 277 with D, or any combination thereof; or
       (ii) substituting amino acid 68 with E, substituting amino acid 84 with W, substituting amino acid 95 with P, substituting amino acid 97 with C, substituting amino acid 168 with E, substituting amino acid 181 with Y, substituting amino acid 226 with C, and substituting amino acid 277 with D;
   (C) the polypeptide of (A) or (B) wherein the polypeptide lacks a leader sequence;
   (D) the polypeptide of (A), (B) or (C) wherein the polypeptide further comprises a heterologous sequence;
   (E) the polypeptide of (D) wherein the heterologous sequence encodes a leader or signal peptide, or an N-terminal identification peptide which provides stabilization or allows for simplified purification;
   (F) the polypeptide of (A), (B), (C), (D) or (E) wherein the polypeptide is glycosylated;
   (G) the polypeptide of (A), (B), (C), (D), (E) or (F) and a stabilizing agent; or (H) the polypeptide of (A), (B), (C), (D), (E), (F) or (G) and a stabilizing agent which comprises urea, polyol, sorbitol, and/or glycerol.

2. The formulation of claim 1, wherein the formulation is or comprises a dietary supplement.

3. The formulation of claim 1, further comprising at least one probiotic, at least one vitamin, at least one additional enzyme, at least one mineral or metal, at least one herb or plant extract, at least one amino acid or amino acid derivative, or any combination thereof.

4. The formulation of claim 3, wherein the mineral or metal is selected from the group consisting of aluminum, antimony, barium, beryllium, bismuth, boron, bromide, bromine, cadmium, calcium, cerium, cesium, chloride, chromium, cobalt, copper, dysprosium, erbium, europium, fluoride, fluorine, gadolinium, gallium, germanium, gold, hafnium, holmium, indium, iodine, iridium, iron, lanthanum, lithium, lutetium, magnesium, manganese, molybdenum, neodymium, nickel, niobium, osmium, palladium, phosphorous, platinum, potassium, praseodymium, promethium, rhenium, rhodium, rubidium, ruthenium, samarium, scandium, selenium, silicon, silver, sodium, strontium, sulfur, tantalum, tellurium, terbium, thorium, thulium, tin, titanium, tungsten, vanadium, ytterbium, yttrium, zinc, zirconium and any combination thereof.

5. The formulation of claim 1, further comprising an herb, a plant extract, diatomaceous earth, charcoal, choline, inositol, biotin, PABA, alpha-lipoic acid, a carotenoid, beta carotene, coenzyine Q10, chondroitin, melatonin, lecithin, brewer's yeast, or a combination thereof.

6. The formulation of claim 1, further comprising alfalfa, ginseng, American ginseng, Asian red ginseng, Asian white ginseng, Siberian ginseng, Brazilian ginseng, astragalus, bilberry, back cohosh, cascara sagrada, cat's claw, cayenne, dong quai, echinacea, eucalyptus, feverfew, garlic, ginkgo biloba, goldenseal, gotu kola, horsetail, maca, a mushroom, Maitake mushroom, Reishi mushroom, Shiitake mushroom, leuzea, rhodiola, milk thistle, noni, pau d'arco, papaya, pygeum, saw palmetto, schizandra, senna, suma, wild yam, willow, yucca, wheat grass, barley grass, parsley, broccoli, acerola cherries, aloe vera, quercitin, pine bark, grape seed, green tea, red wine, grapefruit extract, ginger, oat straw, sarsaparilla, oil, walnut oil, safflower oil, soybean oil, peanut oil, fish oil, salmon oil, evening primrose oil, borage oil, bee pollen, bee propolis, royal jelly, bran, oat bran, wheat bran, fiber, soy, psyllium, apple pectin, protein, egg protein, milk protein, soy protein, rice protein, whey, algae, spirulina, Chlorella, dulse, kelp, D. salina, or a combination thereof.

7. The formulation of claim 3, wherein the probiotic is selected from the group consisting of a *Lactobacillus* species, *L. acidophilus*, *L. bifidus*, *L. sporogenes*, *L. casei*, *L. rhamnosus*, *L. plantarum*, *S. thermophilus*, a *Bifidobacterium* species, an *Escherichia*, an *Enterococcus*, a *Bacillus* and a *Saccharomyces* species.

8. The formulation of claim 3, wherein the additional enzyme is selected from the group consisting of a phytase, an amylase, a bromelain, a cellulase, a chymopapain, a diastase, a glucoamylase, a hemicellulase, a hyaluronidase, an invertase, a lactase, a lipase, a maltase, a pancreatin, a papain, a pectinase, a pepsin, a plasmin, a protease, a rennin and any combination thereof.

9. The formulation of claim 3, wherein the vitamin is selected from the group consisting of vitamin B, Thiamine (Vitamin B1), Riboflavin (Vitamin B2), Nicotinic acid (Niacin, Vitamin B3), Pantothenic acid (Vitamin B5), Pyridoxine (Vitamin B6), B7, Folic acid (Vitamin B9), Cyanocobalamin (Vitamin B 12), vitamin C, a vitamin D, vitamin D1, vitamin D2, vitamin D3, vitamin E, a vitamin K, vitamin K1, vitamin K2, vitamin G, vitamin H, vitamin P and any combination thereof.

10. The formulation of claim 3, wherein the amino acid or amino acid derivative is selected from the group consisting of Isoleucine, Leucine, Lysine, Phenylalanine, Threonine, Tryptophan, Valine, Methionine, Cysteine, Alanine, Arginine, Aspartic Acid, Glutamic Acid, Glycine, Histidine, Proline, Serine, Asparagine, Glutamine, Tyrosine, taurine, glucosamine and any combination thereof.

11. The formulation of claim 1, comprising vitamin D3 or calcium or both.

12. The formulation of claim 1, further comprising potassium, glucose, $CaCl_2$ or a combination thereof.

13. The formulation of claim 1, further comprising at least one enzyme selected from the group consisting of an α-galactosidase, a β-galactosidase, a lactase, a phytase, a β-glucanase, an endo-β-1,4-glucanase, an endo-β-1,3(4)-glucanase, a cellulase, a xylosidase, a galactanase, an arabinogalactan endo-1,4-β-galactosidase, an arabinogalactan endo-1,3-β-galactosidase, an endoglucanase, an endo-1,2-β-glucanase, an endo-1,3-α-glucanase, an endo-1,3-β-glucanase, a pectin degrading enzyme, a pectinase, a pectinesterase, a pectin lyase, a polygalacturonase, an arabinanase, a rhamnogalacturonase, a rhamnogalacturonan acetyl esterase, a rhamnogalacturonan-α-rhamnosidase, a pectate lyase, an α-galacturonisidase, a mannanase, a β-mannosidase, a mannan acetyl esterase, a xylan acetyl esterase, a protease, a xylanase, an arabinoxylanase, a lipase, a phospholipase, and a cutinase.

14. The formulation of claim 1, wherein the formulation is in the form of a powder, a tablet, a concentrate, a gel tab, a capsule, a spray, an aerosol, a lotion, an adhesive patch or a drink.

15. A pharmaceutical composition comprising a pharmaceutically acceptable excipient and the formulation of claim 1.

16. The pharmaceutical composition of claim 15 formulated for oral delivery.

17. The pharmaceutical composition of claim 15 formulated as a pill, a tablet, a capsule, a spray, an aerosol or a powder.

18. A kit comprising the formulation of claim 1, or the pharmaceutical composition of claim 15, and instructions on using the formulation or the pharmaceutical composition.

19. An immobilized phytase comprising:
(A) a polypeptide encoded by a nucleic acid comprising a variant of the nucleic acid of SEQ ID NO:7, wherein said variant has a nucleotide sequence which differs from SEQ ID NO:7 solely by:
(i) substituting nucleotide 389 with G, substituting nucleotide 390 with A, substituting nucleotide 437 with T, substituting nucleotide 438 with G, substituting nucleotide 439 with G, substituting nucleotide 470 with C, substituting nucleotide 472 with T, substituting nucleotide 476 with T, substituting nucleotide 477 with G, substituting nucleotide 478 with T, substituting nucleotide 689 with G, substituting nucleotide 690 with A, substituting nucleotide 691 with G, substituting nucleotide 728 with T, substituting nucleotide 729 with A, substituting nucleotide 730 with T, substituting nucleotide 863 with T, substituting 864 with G, substituting nucleotide 1016 with G, or any combination thereo: or
(ii) substituting nucleotide 389 with G, substituting nucleotide 390 with A, substituting nucleotide 437 with T, substituting nucleotide 438 with G, substituting nucleotide 439 with G, substituting nucleotide 470 with C, substituting nucleotide 472 with T, substituting nucleotide 476 with T, substituting nucleotide 477 with G, substituting nucleotide 478 with T, substituting nucleotide 689 with G, substituting nucleotide 690 with A, substituting nucleotide 691 with G, substituting nucleotide 728 with T, substituting nucleotide 729 with A, substituting nucleotide 730 with T, substituting nucleotide 863 with T, substituting 864 with G, and substituting nucleotide 1016 with G;

(B) a polypeptide which comprises an amino acid sequence which is a variant of SEQ ID NO:8, wherein said variant differs from SEQ ID NO:8 solely by:
  (i) substituting amino acid 68 with E, substituting amino acid 84 with W, substituting amino acid 95 with P, substituting amino acid 97 with C, substituting amino acid 168 with E, substituting amino acid 181 with Y, substituting amino acid 226 with C, substituting amino acid 277 with D, or any combination thereof; or
  (ii) substituting amino acid 68 with E, substituting amino acid 84 with W, substituting amino acid 95 with P, substituting amino acid 97 with C, substituting amino acid 168 with E, substituting amino acid 181 with Y, substituting amino acid 226 with C, and substituting amino acid 277 with D;

(C) the polypeptide of (A) or (B) wherein the polypeptide lacks a leader sequence;

(D) the polypeptide of (A), (B) or (C) wherein the polypeptide further comprises a heterologous sequence;

(E) the polypeptide of (D) wherein the heterologous sequence encodes a leader or signal peptide, or an N-terminal identification peptide which provides stabilization or allows for simplified purification; or (F) the polypeptide of (A), (B), (C), (D) or (E) wherein the polypeptide is glycosylated.

20. The immobilized phytase of claim 19, wherein the polypeptide is immobilized to a bead.

21. The immobilized phytase of claim 20, wherein the polypeptide is immobilized to a polysorb bead or a polystyrene bead.

22. A dietary supplement comprising the immobilized phytase of claim 19.

23. A pharmaceutical composition comprising the immobilized phytase of claim 19.

24. A fertilizer or soil additive comprising the immobilized phytase of claim 19.

25. A fertilizer or soil additive comprising the formulation of claim 1.

26. A liquid supplement comprising: the formulation of claim 1, or the pharmaceutical composition of claim 15.

27. The liquid supplement of claim 26, further comprising glucose, potassium, sodium, or calcium.

28. A hydrating agent comprising a formulation of claim 1.

29. The hydrating agent of claim 28, further comprising glucose, potassium, sodium or calcium.

30. A tissue culture, cell culture media, or a cell culture media additive, comprising the formulation of claim 1.

31. A plant food additive comprising the formulation of claim 1.

* * * * *

UNITED STATES PATENT AND TRADEMARK OFFICE
CERTIFICATE OF CORRECTION

PATENT NO.         : 7,432,097 B2
APPLICATION NO.    : 10/933115
DATED              : October 7, 2008
INVENTOR(S)        : Jay M. Short et al.

It is certified that error appears in the above-identified patent and that said Letters Patent is hereby corrected as shown below:

In column 122, Line 38 in Claim 1, delete "phrase" and insert --phytase--, therefor.
In column 123, Line 29 in Claim 5, delete "coenzyine" and insert --coenzyme--, therefor.
In column 124, Line 64 in Claim 19, delete "thereo:" and insert --thereof;--, therefor.
In column 126, Line 24 in Claim 28, delete "a" and insert --the--, therefor.
In column 126, Line 27 in Claim 30, after "media, or" delete "a".

Signed and Sealed this

Twentieth Day of January, 2009

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 1323
<212> TYPE: DNA
<213> ORGANISM: Escherichia coli
<220> FEATURE:
<221> NAME/KEY: CDS
<222> LOCATION: (1)...(1320)
<220> FEATURE:
<221> NAME/KEY: misc_feature
<222> LOCATION: 216
<223> OTHER INFORMATION: n = A,T,C or G

<400> SEQUENCE: 1 atg aaa gcg atc tta atc cca ttt tta tct ctt ctg att ccg tta acc     48
Met Lys Ala Ile Leu Ile Pro Phe Leu Ser Leu Leu Ile Pro Leu Thr
```

-continued

| | | |
|---|---|---|
| ccg caa tct gca ttc gct cag agt gag ccg gag ctg aag ctg gaa agt<br>Pro Gln Ser Ala Phe Ala Gln Ser Glu Pro Glu Leu Lys Leu Glu Ser<br>　　　　　　20　　　　　　　　25　　　　　　　　30 | 96 |
| gtg gtg att gtc agt cgt cat ggt gtg cgt gct cca acc aag gcc acg<br>Val Val Ile Val Ser Arg His Gly Val Arg Ala Pro Thr Lys Ala Thr<br>　　　　　35　　　　　　　　40　　　　　　　　45 | 144 |
| caa ctg atg cag gat gtc acc cca gac gca tgg cca acc tgg ccg gta<br>Gln Leu Met Gln Asp Val Thr Pro Asp Ala Trp Pro Thr Trp Pro Val<br>　50　　　　　　　　55　　　　　　　　60 | 192 |
| aaa ctg ggt tgg ctg aca ccg cgn ggt ggt gag cta atc gcc tat ctc<br>Lys Leu Gly Trp Leu Thr Pro Arg Gly Gly Glu Leu Ile Ala Tyr Leu<br>　65　　　　　　　　70　　　　　　　　75　　　　　　　　80 | 240 |
| gga cat tac caa cgc cag cgt ctg gta gcc gac gga ttg ctg gcg aaa<br>Gly His Tyr Gln Arg Gln Arg Leu Val Ala Asp Gly Leu Leu Ala Lys<br>　　　　　　　　85　　　　　　　　90　　　　　　　　95 | 288 |
| aag ggc tgc ccg cag tct ggt cag gtc gcg att att gct gat gtc gac<br>Lys Gly Cys Pro Gln Ser Gly Gln Val Ala Ile Ile Ala Asp Val Asp<br>　　　　　100　　　　　　　　105　　　　　　　　110 | 336 |
| gag cgt acc cgt aaa aca ggc gaa gcc ttc gcc gcc ggg ctg gca cct<br>Glu Arg Thr Arg Lys Thr Gly Glu Ala Phe Ala Ala Gly Leu Ala Pro<br>　　　　115　　　　　　　　120　　　　　　　　125 | 384 |
| gac tgt gca ata acc gta cat acc cag gca gat acg tcc agt ccc gat<br>Asp Cys Ala Ile Thr Val His Thr Gln Ala Asp Thr Ser Ser Pro Asp<br>130　　　　　　　　135　　　　　　　　140 | 432 |
| ccg tta ttt aat cct cta aaa act ggc gtt tgc caa ctg gat aac gcg<br>Pro Leu Phe Asn Pro Leu Lys Thr Gly Val Cys Gln Leu Asp Asn Ala<br>145　　　　　　　　150　　　　　　　　155　　　　　　　　160 | 480 |
| aac gtg act gac gcg atc ctc agc agg gca gga ggg tca att gct gac<br>Asn Val Thr Asp Ala Ile Leu Ser Arg Ala Gly Gly Ser Ile Ala Asp<br>　　　　　　　　165　　　　　　　　170　　　　　　　　175 | 528 |
| ttt acc ggg cat cgg caa acg gcg ttt cgc gaa ctg gaa cgg gtg ctt<br>Phe Thr Gly His Arg Gln Thr Ala Phe Arg Glu Leu Glu Arg Val Leu<br>　　　　180　　　　　　　　185　　　　　　　　190 | 576 |
| aat ttt ccg caa tca aac ttg tgc ctt aaa cgt gag aaa cag gac gaa<br>Asn Phe Pro Gln Ser Asn Leu Cys Leu Lys Arg Glu Lys Gln Asp Glu<br>　　　195　　　　　　　　200　　　　　　　　205 | 624 |
| agc tgt tca tta acg cag gca tta cca tcg gaa ctc aag gtg agc gcc<br>Ser Cys Ser Leu Thr Gln Ala Leu Pro Ser Glu Leu Lys Val Ser Ala<br>210　　　　　　　　215　　　　　　　　220 | 672 |
| gac aat gtc tca tta acc ggt gcg gta agc ctc gca tca atg ctg acg<br>Asp Asn Val Ser Leu Thr Gly Ala Val Ser Leu Ala Ser Met Leu Thr<br>225　　　　　　　　230　　　　　　　　235　　　　　　　　240 | 720 |
| gag ata ttt ctc ctg caa caa gca cag gga atg ccg gag ccg ggg tgg<br>Glu Ile Phe Leu Leu Gln Gln Ala Gln Gly Met Pro Glu Pro Gly Trp<br>　　　　　　　　245　　　　　　　　250　　　　　　　　255 | 768 |
| gga agg atc acc gat tca cac cag tgg aac acc ttg cta agt ttg cat<br>Gly Arg Ile Thr Asp Ser His Gln Trp Asn Thr Leu Leu Ser Leu His<br>　　　　260　　　　　　　　265　　　　　　　　270 | 816 |
| aac gcg caa ttt tat ttg cta caa cgc acg cca gag gtt gcc cgc agc<br>Asn Ala Gln Phe Tyr Leu Leu Gln Arg Thr Pro Glu Val Ala Arg Ser<br>　　　275　　　　　　　　280　　　　　　　　285 | 864 |
| cgc gcc acc ccg tta ttg gat ttg atc atg gca gcg ttg acg ccc cat<br>Arg Ala Thr Pro Leu Leu Asp Leu Ile Met Ala Ala Leu Thr Pro His<br>290　　　　　　　　295　　　　　　　　300 | 912 |
| cca ccg caa aaa cag gcg tat ggt gtg aca tta ccc act tca gta ctg<br>Pro Pro Gln Lys Gln Ala Tyr Gly Val Thr Leu Pro Thr Ser Val Leu<br>305　　　　　　　　310　　　　　　　　315　　　　　　　　320 | 960 |
| ttt att gcc gga cac gat act aat ctg gca aat ctc ggc ggc gca ctg<br> | 1008 |

```
                Phe Ile Ala Gly His Asp Thr Asn Leu Ala Asn Leu Gly Gly Ala Leu
                            325                 330                 335 gag ctc aac tgg acg ctt ccc ggt cag ccg gat aac acg ccg cca ggt        1056
Glu Leu Asn Trp Thr Leu Pro Gly Gln Pro Asp Asn Thr Pro Pro Gly
            340                 345                 350 ggt gaa ctg gtg ttt gaa cgc tgg cgt cgg cta agc gat aac agc cag        1104
Gly Glu Leu Val Phe Glu Arg Trp Arg Arg Leu Ser Asp Asn Ser Gln
        355                 360                 365 tgg att cag gtt tcg ctg gtc ttc cag act tta cag cag atg cgt gat        1152
Trp Ile Gln Val Ser Leu Val Phe Gln Thr Leu Gln Gln Met Arg Asp
    370                 375                 380 aaa acg ccg ctg tca tta aat acg ccg ccc gga gag gtg aaa ctg acc        1200
Lys Thr Pro Leu Ser Leu Asn Thr Pro Pro Gly Glu Val Lys Leu Thr
385                 390                 395                 400 ctg gca gga tgt gaa gag cga aat gcg cag ggc atg tgt tcg ttg gca        1248
Leu Ala Gly Cys Glu Glu Arg Asn Ala Gln Gly Met Cys Ser Leu Ala
                405                 410                 415 ggt ttt acg caa atc gtg aat gaa gca cgc ata ccg gcg tgc agt ttg        1296
Gly Phe Thr Gln Ile Val Asn Glu Ala Arg Ile Pro Ala Cys Ser Leu
            420                 425                 430 aga tct cat cac cat cac cat cac taa                                    1323
Arg Ser His His His His His His
        435                 440

<210> SEQ ID NO 2
<211> LENGTH: 440
<212> TYPE: PRT
<213> ORGANISM: Escherichia coli

<400> SEQUENCE: 2

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
```

-continued

```
              210                 215                 220
Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Met Ala Ala Leu Thr Pro His
290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

Arg Ser His His His His His His
            435                 440

<210> SEQ ID NO 3
<211> LENGTH: 49
<212> TYPE: DNA
<213> ORGANISM: Artificial Sequence
<220> FEATURE:
<223> OTHER INFORMATION: primer

<400> SEQUENCE: 3
gtttctgaat tcaaggagga atttaaatga aagcgatctt aatcccatt              49

<210> SEQ ID NO 4
<211> LENGTH: 33
<212> TYPE: DNA
<213> ORGANISM: Artificial Sequence
<220> FEATURE:
<223> OTHER INFORMATION: primer

<400> SEQUENCE: 4
gtttctggat ccttacaaac tgcacgccgg tat                               33

<210> SEQ ID NO 5
<211> LENGTH: 1901
<212> TYPE: DNA
<213> ORGANISM: Escherichia coli
<220> FEATURE:
<221> NAME/KEY: misc_feature
<222> LOCATION: 403
<223> OTHER INFORMATION: n = A,T,C or G

<400> SEQUENCE: 5
```

```
taaggagcag aaacaatgtg gtatttactt tggttcgtcg gcattttgtt gatgtgttcg      60
ctctccaccc ttgtgttggt atggctggac ccgcgtctga aaagttaacg aacgtaggcc     120
tgatgcggcg cattagcatc gcatcaggca atcaataatg tcagatatga aaagcggaaa     180
catatcgatg aaagcgatct taatcccatt tttatctctt ctgattccgt taaccccgca     240
atctgcattc gctcagagtg agccggagct gaagctggaa agtgtggtga ttgtcagtcg     300
tcatggtgtg cgtgctccaa ccaaggccac gcaactgatg caggatgtca ccccagacgc     360
atggccaacc tggccggtaa aactgggtga gctgacaccg cgnggtggtg agctaatcgc     420
ctatctcgga cattaccaac gccagcgtct ggtagccgac ggattgctgg cgaaaaaggg     480
ctgcccgcag tctggtcagg tcgcgattat tgctgatgtc gacgagcgta cccgtaaaac     540
aggcgaagcc ttcgccgccg ggctggcacc tgactgtgca ataaccgtac atacccaggc     600
agatacgtcc agtcccgatc cgttatttaa tcctctaaaa actggcgttt gccaactgga     660
taacgcgaac gtgactgacg cgatcctcag cagggcagga gggtcaattg ctgactttac     720
cgggcatcgg caaacggcgt ttcgcgaact ggaacgggtg cttaattttc cgcaatcaaa     780
cttgtgcctt aaacgtgaga aacaggacga aagctgttca ttaacgcagg cattaccatc     840
ggaactcaag gtgagcgccg acaatgtctc attaaccggt gcggtaagcc tcgcatcaat     900
gctgacggag atatttctcc tgcaacaagc acagggaatg ccggagccgg ggtggggaag     960
gatcaccgat tcacaccagt ggaacacctt gctaagtttg cataacgcgc aattttattt    1020
gctacaacgc acgccagagg ttgcccgcag ccgcgccacc ccgttattag atttgatcaa    1080
gacagcgttg acgccccatc caccgcaaaa acaggcgtat ggtgtgacat tacccacttc    1140
agtgctgttt atcgccggac acgatactaa tctggcaaat ctcggcggcg cactggagct    1200
caactggacg cttcccggtc agccggataa cacgccgcca ggtggtgaac tggtgtttga    1260
acgctggcgt cggctaagcg ataacagcca gtggattcag gtttcgctgg tcttccagac    1320
tttacagcag atgcgtgata aaacgccgct gtcattaaat acgccgcccg gagaggtgaa    1380
actgaccctg gcaggatgtg aagagcgaaa tgcgcagggc atgtgttcgt ggcaggttt    1440 tacgcaaatc gtgaatgaag cacgcatacc ggcgtgcagt ttgtaatgca taaaaaagag    1500
cattcagtta cctgaatgct ctgaggctga tgacaaacga agaactgtct aatgcgtaga    1560
ccggaaaagg cgttcacgcc gcatccggcc actttcagtt ttcctctttc tcggagtaac    1620
tataaccgta atagttatag ccgtaactgt aagcggtgct ggcgcgttta atcacaccat    1680
tgaggatagc gcctttaata ttgacgcctg cctgttccag acgctgcatt gacaaactca    1740
cctctttggc ggtgttcaag ccaaaacgcg caaccagcag gctggtgcca acagaacgcc    1800
ccacgaccgc ggcatcactc accgccagca tcggcggcgt atcgacaatc accagatcgt    1860
aatggtcgtt cgcccattcc agtaattgac gcatccgatc g                        1901
```

<210> SEQ ID NO 6
<211> LENGTH: 1901
<212> TYPE: DNA
<213> ORGANISM: Escherichia coli
<220> FEATURE:
<221> NAME/KEY: misc_feature
<222> LOCATION: 403
<223> OTHER INFORMATION: n = A,T,C or G

<400> SEQUENCE: 6

```
taaggagcag aaacaatgtg gtatttactt tggttcgtcg gcattttgtt gatgtgttcg      60
```

```
ctctccaccc ttgtgttggt atggctggac ccgcgtctga aaagttaacg aacgtaggcc      120
tgatgcggcg cattagcatc gcatcaggca atcaataatg tcagatatga aaagcggaaa      180
catatcgatg aaagcgatct taatcccatt tttatctctt ctgattccgt taaccccgca      240
atctgcattc gctcagagtg agccggagct gaagctggaa agtgtggtga ttgtcagtcg      300
tcatggtgtg cgtgctccaa ccaaggccac gcaactgatg caggatgtca ccccagacgc      360
atggccaacc tggccggtaa aactgggttg gctgacaccg cgnggtggtg agctaatcgc      420
ctatctcgga cattacctgg gccagcgtct ggtagccgac ggattgctgg cgaaaaaggg      480
ctgcccgcag tctggtcagg tcgcgattat tgctgatgtc gacgagcgta cccgtaaaac      540
aggcgaagcc ttcgccgccg ggctggcacc tgactgtgca ataaccgtac atacccaggc      600
agatacgtcc agtcccgatc cgttatttaa tcctctaaaa actggcgttt gccaactgga      660
taacgcgaac gtgactgacg cgatcctcag cagggcagga gggtcaattg ctgactttac      720
cgggcatcgg caaacggcgt tcgcgaact  ggaacgggtg cttaattttc cgcaatcaaa      780
cttgtgcctt aaacgtgaga acaggacga  aagctgttca ttaacgcagg cattaccatc      840
ggaactcaag gtgagcgccg acaatgtctc attaaccggt gcggtaagcc tcgcatcaat      900
gctgacggag atatttctcc tgcaacaagc acagggaatg ccggagccgg ggtggggaag      960
gatcaccgat tcacaccagt ggaacaccct tgctaagtttg cataacgcgc aatttttattt     1020 gctacaacgc acgccagagg ttgcccgcag ccgcgccacc ccgttattag atttgatcaa     1080
gacagcgttg acgccccatc caccgcaaaa acaggcgtat ggtgtgacat acccacttc      1140 agtgctgttt atcgccggac acgatactaa tctgcaaat  ctcggcggcg cactggagct     1200
caactggacg cttcccggtc agccggataa cacgccgcca ggtggtgaac tggtgtttga     1260
acgctggcgt cggctaagcg ataacagcca gtggattcag gtttcgctgg tcttccagac     1320
tttacagcag atgcgtgata aaacgccgct gtcattaaat acgccgcccg gagaggtgaa     1380
actgaccctg gcaggatgtg aagagcgaaa tgcgcagggc atgtgttcgt tggcaggttt     1440
tacgcaaatc gtgaatgaag cacgcatacc ggcgtgcagt ttgtaatgca taaaaaagag     1500
cattcagtta cctgaatgct ctgaggctga tgacaaacga agaactgtct aatgcgtaga     1560
ccggaaaagg cgttcacgcc gcatccggcc actttcagtt ttcctctttc tcggagtaac     1620
tataaccgta atagttatag ccgtaactgt aagcggtgct ggcgcgttta atcacaccat     1680
tgaggatagc gcctttaata ttgacgcctg cctgttccag acgctgcatt gacaaactca     1740
cctctttggc ggtgttcaag ccaaaacgcg caaccagcag gctggtgcca acagaacgcc     1800
ccacgaccgc ggcatcactc accgccagca tcggcggcgt atcgacaatc accagatcgt     1860
aatggtcgtt cgcccattcc agtaattgac gcatccgatc g                         1901

<210> SEQ ID NO 7
<211> LENGTH: 1901
<212> TYPE: DNA
<213> ORGANISM: Escherichia coli
<220> FEATURE:
<221> NAME/KEY: CDS
<222> LOCATION: (188)...(1483)
<220> FEATURE:
<221> NAME/KEY: misc_feature
<222> LOCATION: 403
<223> OTHER INFORMATION: n = A,T,C or G

<400> SEQUENCE: 7
taaggagcag aaacaatgtg gtatttactt tggttcgtcg gcattttgtt gatgtgttcg       60
```

-continued

```
ctctccaccc ttgtgttggt atggctggac ccgcgtctga aaagttaacg aacgtaggcc      120
tgatgcggcg cattagcatc gcatcaggca atcaataatg tcagatatga aaagcggaaa      180 catatcg atg aaa gcg atc tta atc cca ttt tta tct ctt ctg att ccg        229
        Met Lys Ala Ile Leu Ile Pro Phe Leu Ser Leu Leu Ile Pro
        1               5                   10 tta acc ccg caa tct gca ttc gct cag agt gag ccg gag ctg aag ctg        277
Leu Thr Pro Gln Ser Ala Phe Ala Gln Ser Glu Pro Glu Leu Lys Leu
15              20                  25                  30 gaa agt gtg gtg att gtc agt cgt cat ggt gtg cgt gct cca acc aag        325
Glu Ser Val Val Ile Val Ser Arg His Gly Val Arg Ala Pro Thr Lys
                35                  40                  45 gcc acg caa ctg atg cag gat gtc acc cca gac gca tgg cca acc tgg        373
Ala Thr Gln Leu Met Gln Asp Val Thr Pro Asp Ala Trp Pro Thr Trp
            50                  55                  60 ccg gta aaa ctg ggt tgg ctg aca ccg cgn ggt ggt gag cta atc gcc        421
Pro Val Lys Leu Gly Trp Leu Thr Pro Arg Gly Gly Glu Leu Ile Ala
        65                  70                  75 tat ctc gga cat tac caa cgc cag cgt ctg gta gcc gac gga ttg ctg        469
Tyr Leu Gly His Tyr Gln Arg Gln Arg Leu Val Ala Asp Gly Leu Leu
    80                  85                  90 gcg aaa aag ggc tgc ccg cag tct ggt cag gtc gcg att att gct gat        517
Ala Lys Lys Gly Cys Pro Gln Ser Gly Gln Val Ala Ile Ile Ala Asp
95                  100                 105                 110 gtc gac gag cgt acc cgt aaa aca ggc gaa gcc ttc gcc gcc ggg ctg        565
Val Asp Glu Arg Thr Arg Lys Thr Gly Glu Ala Phe Ala Ala Gly Leu
                115                 120                 125 gca cct gac tgt gca ata acc gta cat acc cag gca gat acg tcc agt        613
Ala Pro Asp Cys Ala Ile Thr Val His Thr Gln Ala Asp Thr Ser Ser
            130                 135                 140 ccc gat ccg tta ttt aat cct cta aaa act ggc gtt tgc caa ctg gat        661
Pro Asp Pro Leu Phe Asn Pro Leu Lys Thr Gly Val Cys Gln Leu Asp
        145                 150                 155 aac gcg aac gtg act gac gcg atc ctc agc agg gca gga ggg tca att        709
Asn Ala Asn Val Thr Asp Ala Ile Leu Ser Arg Ala Gly Gly Ser Ile
    160                 165                 170 gct gac ttt acc ggg cat cgg caa acg gcg ttt cgc gaa ctg gaa cgg        757
Ala Asp Phe Thr Gly His Arg Gln Thr Ala Phe Arg Glu Leu Glu Arg
175                 180                 185                 190 gtg ctt aat ttt ccg caa tca aac ttg tgc ctt aaa cgt gag aaa cag        805
Val Leu Asn Phe Pro Gln Ser Asn Leu Cys Leu Lys Arg Glu Lys Gln
                195                 200                 205 gac gaa agc tgt tca tta acg cag gca tta cca tcg gaa ctc aag gtg        853
Asp Glu Ser Cys Ser Leu Thr Gln Ala Leu Pro Ser Glu Leu Lys Val
            210                 215                 220 agc gcc gac aat gtc tca tta acc ggt gcg gta agc ctc gca tca atg        901
Ser Ala Asp Asn Val Ser Leu Thr Gly Ala Val Ser Leu Ala Ser Met
        225                 230                 235 ctg acg gag ata ttt ctc ctg caa caa gca cag gga atg ccg gag ccg        949
Leu Thr Glu Ile Phe Leu Leu Gln Gln Ala Gln Gly Met Pro Glu Pro
    240                 245                 250 ggg tgg gga agg atc acc gat tca cac cag tgg aac acc ttg cta agt        997
Gly Trp Gly Arg Ile Thr Asp Ser His Gln Trp Asn Thr Leu Leu Ser
255                 260                 265                 270 ttg cat aac gcg caa ttt tat ttg cta caa cgc acg cca gag gtt gcc       1045
Leu His Asn Ala Gln Phe Tyr Leu Leu Gln Arg Thr Pro Glu Val Ala
                275                 280                 285 cgc agc cgc gcc acc ccg tta tta gat ttg atc aag aca gcg ttg acg       1093
Arg Ser Arg Ala Thr Pro Leu Leu Asp Leu Ile Lys Thr Ala Leu Thr
            290                 295                 300
```

-continued

| | | |
|---|---|---|
| ccc cat cca ccg caa aaa cag gcg tat ggt gtg aca tta ccc act tca<br>Pro His Pro Pro Gln Lys Gln Ala Tyr Gly Val Thr Leu Pro Thr Ser<br>      305                       310                        315 | 1141 |
| gtg ctg ttt atc gcc gga cac gat act aat ctg gca aat ctc ggc ggc<br>Val Leu Phe Ile Ala Gly His Asp Thr Asn Leu Ala Asn Leu Gly Gly<br>320                       325                       330 | 1189 |
| gca ctg gag ctc aac tgg acg ctt ccc ggt cag ccg gat aac acg ccg<br>Ala Leu Glu Leu Asn Trp Thr Leu Pro Gly Gln Pro Asp Asn Thr Pro<br>335                  340                     345                  350 | 1237 |
| cca ggt ggt gaa ctg gtg ttt gaa cgc tgg cgt cgg cta agc gat aac<br>Pro Gly Gly Glu Leu Val Phe Glu Arg Trp Arg Arg Leu Ser Asp Asn<br>               355                     360                   365 | 1285 |
| agc cag tgg att cag gtt tcg ctg gtc ttc cag act tta cag cag atg<br>Ser Gln Trp Ile Gln Val Ser Leu Val Phe Gln Thr Leu Gln Gln Met<br>      370                       375                       380 | 1333 |
| cgt gat aaa acg ccg ctg tca tta aat acg ccg ccc gga gag gtg aaa<br>Arg Asp Lys Thr Pro Leu Ser Leu Asn Thr Pro Pro Gly Glu Val Lys<br>385                       390                      395 | 1381 |
| ctg acc ctg gca gga tgt gaa gag cga aat gcg cag ggc atg tgt tcg<br>Leu Thr Leu Ala Gly Cys Glu Glu Arg Asn Ala Gln Gly Met Cys Ser<br>    400                       405                       410 | 1429 |
| ttg gca ggt ttt acg caa atc gtg aat gaa gca cgc ata ccg gcg tgc<br>Leu Ala Gly Phe Thr Gln Ile Val Asn Glu Ala Arg Ile Pro Ala Cys<br>415                       420                      425                  430 | 1477 |
| agt ttg taatgcataa aaagagcat tcagttacct gaatgctctg aggctgatga<br>Ser Leu | 1533 |
| caaacgaaga actgtctaat gcgtagaccg gaaaaggcgt tcacgccgca tccggccact | 1593 |
| ttcagttttc ctctttctcg gagtaactat aaccgtaata gttatagccg taactgtaag | 1653 |
| cggtgctggc gcgtttaatc acaccattga ggatagcgcc tttaatattg acgcctgcct | 1713 |
| gttccagacg ctgcattgac aaactcacct ctttggcggt gttcaagcca aaacgcgcaa | 1773 |
| ccagcaggct ggtgccaaca gaacgcccca cgaccgcggc atcactcacc gccagcatcg | 1833 |
| gcggcgtatc gacaatcacc agatcgtaat ggtcgttcgc ccattccagt aattgacgca | 1893 |
| tccgatcg | 1901 |

<210> SEQ ID NO 8
<211> LENGTH: 432
<212> TYPE: PRT
<213> ORGANISM: Escherichia coli

<400> SEQUENCE: 8

Met Lys Ala Ile Leu Ile Pro Phe Leu Ser Leu Leu Ile Pro Leu Thr
 1               5                  10                  15

Pro Gln Ser Ala Phe Ala Gln Ser Glu Pro Glu Leu Lys Leu Glu Ser
             20                  25                  30

Val Val Ile Val Ser Arg His Gly Val Arg Ala Pro Thr Lys Ala Thr
         35                  40                  45

Gln Leu Met Gln Asp Val Thr Pro Asp Ala Trp Pro Thr Trp Pro Val
     50                  55                  60

Lys Leu Gly Trp Leu Thr Pro Arg Gly Gly Glu Leu Ile Ala Tyr Leu
 65                  70                  75                  80

Gly His Tyr Gln Arg Gln Arg Leu Val Ala Asp Gly Leu Leu Ala Lys
                 85                  90                  95

Lys Gly Cys Pro Gln Ser Gly Gln Val Ala Ile Ile Ala Asp Val Asp
            100                 105                 110

```
Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
    130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Ser Ile Ala Asp
                165                 170                 175

Phe Thr Gly His Arg Gln Thr Ala Phe Arg Glu Leu Glu Arg Val Leu
                180                 185                 190

Asn Phe Pro Gln Ser Asn Leu Cys Leu Lys Arg Glu Lys Gln Asp Glu
            195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Arg Leu Ser Asp Asn Ser Gln
        355                 360                 365

Trp Ile Gln Val Ser Leu Val Phe Gln Thr Leu Gln Gln Met Arg Asp
    370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 9
<211> LENGTH: 1308
<212> TYPE: DNA
<213> ORGANISM: Artificial Sequence
<220> FEATURE:
<223> OTHER INFORMATION: modified phytase enzyme
<220> FEATURE:
<221> NAME/KEY: CDS
<222> LOCATION: (1)...(1296)

<400> SEQUENCE: 9 atg aaa gcg atc tta atc cca ttt tta tct ctt ctg att ccg tta acc      48
Met Lys Ala Ile Leu Ile Pro Phe Leu Ser Leu Leu Ile Pro Leu Thr
1               5                   10                  15 ccg caa tct gca ttc gct cag agt gag ccg gag ctg aag ctg gaa agt      96
Pro Gln Ser Ala Phe Ala Gln Ser Glu Pro Glu Leu Lys Leu Glu Ser
```

```
                  20                  25                  30 gtg gtg att gtc agt cgt cat ggt gtg cgt gct cca acc aag gcc acg      144
Val Val Ile Val Ser Arg His Gly Val Arg Ala Pro Thr Lys Ala Thr
         35                  40                  45 caa ctg atg cag gat gtc acc cca gac gca tgg cca acc tgg ccg gta      192
Gln Leu Met Gln Asp Val Thr Pro Asp Ala Trp Pro Thr Trp Pro Val
 50                  55                  60 aaa ctg ggt gag ctg aca ccg cgc ggt ggt gag cta atc gcc tat ctc      240
Lys Leu Gly Glu Leu Thr Pro Arg Gly Gly Glu Leu Ile Ala Tyr Leu
 65                  70                  75                  80 gga cat tac tgg cgt cag cgt ctg gta gcc gac gga ttg ctg cct aaa      288
Gly His Tyr Trp Arg Gln Arg Leu Val Ala Asp Gly Leu Leu Pro Lys
                 85                  90                  95 tgt ggc tgc ccg cag tct ggt cag gtc gcg att att gct gat gtc gac      336
Cys Gly Cys Pro Gln Ser Gly Gln Val Ala Ile Ile Ala Asp Val Asp
                100                 105                 110 gag cgt acc cgt aaa aca ggc gaa gcc ttc gcc gcc ggg ctg gca cct      384
Glu Arg Thr Arg Lys Thr Gly Glu Ala Phe Ala Ala Gly Leu Ala Pro
                115                 120                 125 gac tgt gca ata acc gta cat acc cag gca gat acg tcc agt ccc gat      432
Asp Cys Ala Ile Thr Val His Thr Gln Ala Asp Thr Ser Ser Pro Asp
    130                 135                 140 ccg tta ttt aat cct cta aaa act ggc gtt tgc caa ctg gat aac gcg      480
Pro Leu Phe Asn Pro Leu Lys Thr Gly Val Cys Gln Leu Asp Asn Ala
145                 150                 155                 160 aac gtg act gac gcg atc ctc gag agg gca gga ggg tca att gct gac      528
Asn Val Thr Asp Ala Ile Leu Glu Arg Ala Gly Gly Ser Ile Ala Asp
                165                 170                 175 ttt acc ggg cat tat caa acg gcg ttt cgc gaa ctg gaa cgg gtg ctt      576
Phe Thr Gly His Tyr Gln Thr Ala Phe Arg Glu Leu Glu Arg Val Leu
                180                 185                 190 aat ttt ccg caa tca aac ttg tgc ctt aaa cgt gag aaa cag gac gaa      624
Asn Phe Pro Gln Ser Asn Leu Cys Leu Lys Arg Glu Lys Gln Asp Glu
                195                 200                 205 agc tgt tca tta acg cag gca tta cca tcg gaa ctc aag gtg agc gcc      672
Ser Cys Ser Leu Thr Gln Ala Leu Pro Ser Glu Leu Lys Val Ser Ala
    210                 215                 220 gac tgt gtc tca tta acc ggt gcg gta agc ctc gca tca atg ctg acg      720
Asp Cys Val Ser Leu Thr Gly Ala Val Ser Leu Ala Ser Met Leu Thr
225                 230                 235                 240 gag ata ttt ctc ctg caa caa gca cag gga atg ccg gag ccg ggg tgg      768
Glu Ile Phe Leu Leu Gln Gln Ala Gln Gly Met Pro Glu Pro Gly Trp
                245                 250                 255 gga agg atc acc gat tca cac cag tgg aac acc ttg cta agt ttg cat      816
Gly Arg Ile Thr Asp Ser His Gln Trp Asn Thr Leu Leu Ser Leu His
                260                 265                 270 aac gcg caa ttt gat ttg cta caa cgc acg cca gag gtt gcc cgc agc      864
Asn Ala Gln Phe Asp Leu Leu Gln Arg Thr Pro Glu Val Ala Arg Ser
    275                 280                 285 cgc gcc acc ccg tta tta gat ttg atc aag aca gcg ttg acg ccc cat      912
Arg Ala Thr Pro Leu Leu Asp Leu Ile Lys Thr Ala Leu Thr Pro His
    290                 295                 300 cca ccg caa aaa cag gcg tat ggt gtg aca tta ccc act tca gtg ctg      960
Pro Pro Gln Lys Gln Ala Tyr Gly Val Thr Leu Pro Thr Ser Val Leu
305                 310                 315                 320 ttt atc gcc gga cac gat act aat ctg gca aat ctc ggc ggc gca ctg     1008
Phe Ile Ala Gly His Asp Thr Asn Leu Ala Asn Leu Gly Gly Ala Leu
                325                 330                 335 gag ctc aac tgg acg ctt ccc ggt cag ccg gat aac acg ccg cca ggt     1056
```

```
Glu Leu Asn Trp Thr Leu Pro Gly Gln Pro Asp Asn Thr Pro Pro Gly
            340                 345                 350 ggt gaa ctg gtg ttt gaa cgc tgg cgt cgg cta agc gat aac agc cag    1104
Gly Glu Leu Val Phe Glu Arg Trp Arg Arg Leu Ser Asp Asn Ser Gln
            355                 360                 365 tgg att cag gtt tcg ctg gtc ttc cag act tta cag cag atg cgt gat    1152
Trp Ile Gln Val Ser Leu Val Phe Gln Thr Leu Gln Gln Met Arg Asp
        370                 375                 380 aaa acg ccg ctg tca tta aat acg ccg ccc gga gag gtg aaa ctg acc    1200
Lys Thr Pro Leu Ser Leu Asn Thr Pro Pro Gly Glu Val Lys Leu Thr
385                 390                 395                 400 ctg gca gga tgt gaa gag cga aat gcg cag ggc atg tgt tcg ttg gca    1248
Leu Ala Gly Cys Glu Glu Arg Asn Ala Gln Gly Met Cys Ser Leu Ala
                405                 410                 415 ggt ttt acg caa atc gtg aat gaa gca cgc ata ccg gcg tgc agt ttg    1296
Gly Phe Thr Gln Ile Val Asn Glu Ala Arg Ile Pro Ala Cys Ser Leu
            420                 425                 430 agatctcatc ta                                                      1308

<210> SEQ ID NO 10
<211> LENGTH: 432
<212> TYPE: PRT
<213> ORGANISM: Artificial Sequence
<220> FEATURE:
<223> OTHER INFORMATION: modified phytase enzyme

<400> SEQUENCE: 10

Met Lys Ala Ile Leu Ile Pro Phe Leu Ser Leu Leu Ile Pro Leu Thr
  1               5                  10                  15

Pro Gln Ser Ala Phe Ala Gln Ser Glu Pro Glu Leu Lys Leu Glu Ser
             20                  25                  30

Val Val Ile Val Ser Arg His Gly Val Arg Ala Pro Thr Lys Ala Thr
         35                  40                  45

Gln Leu Met Gln Asp Val Thr Pro Asp Ala Trp Pro Thr Trp Pro Val
     50                  55                  60

Lys Leu Gly Glu Leu Thr Pro Arg Gly Gly Glu Leu Ile Ala Tyr Leu
 65                  70                  75                  80

Gly His Tyr Trp Arg Gln Arg Leu Val Ala Asp Gly Leu Leu Pro Lys
                 85                  90                  95

Cys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
        115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Glu Arg Ala Gly Gly Ser Ile Ala Asp
                165                 170                 175

Phe Thr Gly His Tyr Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Cys Val Ser Leu Thr Gly Ala Val Ser Leu Ala Ser Met Leu Thr
225                 230                 235                 240
```

-continued

```
Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Asp Leu Leu Gln Arg Thr Pro Glu Val Ala Arg Ser
            275                 280                 285

Arg Ala Thr Pro Leu Leu Asp Leu Ile Lys Thr Ala Leu Thr Pro His
        290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Arg Leu Ser Asp Asn Ser Gln
            355                 360                 365

Trp Ile Gln Val Ser Leu Val Phe Gln Thr Leu Gln Gln Met Arg Asp
        370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430
```